US005494890A

United States Patent [19]

Cederbaum et al.

[11] Patent Number: 5,494,890

[45] Date of Patent: Feb. 27, 1996

[54] HERBICIDALLY, ACARICIDALLY AND INSECTICIDALLY ACTIVE PYRAZOLIDINE COMPOUNDS

[75] Inventors: Frederik Cederbaum, Oberwil; Hans-Georg Brunner, Lausen, both of Switzerland; Manfred Böger, Weil am Rhein, Germany

[73] Assignee: Ciba-Geigy Corporation, Tarrytown, N.Y.

[21] Appl. No.: 460,486

[22] Filed: Jun. 2, 1995

Related U.S. Application Data

[62] Division of Ser. No. 119,103, filed as PCT/EP92/00452, Mar. 2, 1992.

[30] Foreign Application Priority Data

Mar. 19, 1991 [CH] Switzerland .............................. 826/91

[51] Int. Cl.[6] .......................... A01N 43/56; C07D 487/04

[52] U.S. Cl. .......................... 504/281; 504/253; 514/338; 514/405; 546/271; 548/363.1

[58] Field of Search ......................... 546/271; 548/363.1; 504/281; 514/338

[56] References Cited

U.S. PATENT DOCUMENTS 4,128,425 12/1978 Greenwald .

FOREIGN PATENT DOCUMENTS 0011693 of 1980 European Pat. Off. .
0042100 12/1981 European Pat. Off. .
0094095 11/1983 European Pat. Off. .
0106251 4/1984 European Pat. Off. .
0355599 2/1990 European Pat. Off. .
0377893 7/1990 European Pat. Off. .
0415211 3/1991 European Pat. Off. .
0415185 3/1991 European Pat. Off. .
0442077 8/1991 European Pat. Off. .
0442073 8/1991 European Pat. Off. .

*Primary Examiner*—Robert W. Ramsuer
*Attorney, Agent, or Firm*—William A. Teoli, Jr.; Marla J. Mathias

[57] ABSTRACT

The present invention relates to herbicidally, acaricidally and insecticidally active pyrazolidine-3,5-diones of the formula I

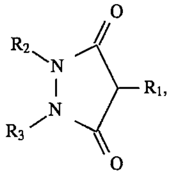

(I)

in which $R_1$ is

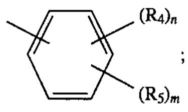

;

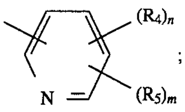

; or

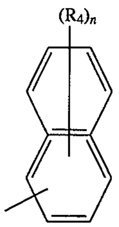

$R_2$ and $R_3$ independently of one another are $C_1$–$C_6$alkyl; $C_3$–$C_6$ alkenyl; or $C_3$–$C_6$alkynyl; or $R_2$ and $R_3$ together are a $-(CH_2)_3-$, $-(CH_2)_4-$, $-CH_2-CH=CH-CH_2-$, $-CH_2-CH=CH-$ or $-(CH_2)_2-CH=CH-$ bridge which is unsubstituted or up to trisubstituted by $C_1$–$C_4$alkyl;

n is 0; 1; 2; 3; or 4;

m is 0; or 1; the total of m and n being less than, or equal to, 4; the $R_4$ radicals independently of one another are halogen; nitro; cyano, $C_1$–$C_4$alkyl; $C_1$–$C_4$haloalkyl; $C_1$–$C_{10}$alkoxy; $C_1$–$C_4$haloalkoxy; $C_3$–$C_6$alkenyloxy; $C_1$–$C_4$alkoxy-$C_2$–$C_4$alkoxy; $C_3$–$C_6$alkynyloxy; $C_1$–$C_4$alkylcarbonyl; $C_1$–$C_4$alkoxycarbonyl; $C_1$–$C_4$alkylthio; $C_1$–$C_4$alkylsulfinyl; $C_1$–$C_4$ alkylsulfonyl; amino; mono-$C_1$–$C_4$alkylamino; di-$C_1$–$C_4$alkylamino;

$R_5$ is

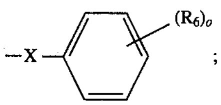

;

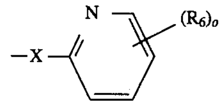

X is oxygen; sulfur; $CH_2$; or $NR_7$;

o is 0; 1; 2; or 3;

$R_6$ radicals independently of one another are $C_1$–$C_4$alkyl; halogen; $C_1$–$C_4$haloalkyl; $C_1$–$C_4$haloalkoxy; $C_1$–$C_4$alkoxy; nitro; cyano; $C_1$–$C_4$alkoxycarbonyl; amino; mono-$C_1$–$C_4$alkylamino; or di-$C_1$–$C_4$alkylamino; and $R_7$ is hydrogen; $C_1$–$C_4$alkyl; formyl; or $C_1$–$C_4$alkylcarbonyl;
the acid addition salts thereof, herbicidally, acaricidally or insecticidally active compositions as well as to methods for controlling weeds, Acarina or insects.

18 Claims, No Drawings

HERBICIDALLY, ACARICIDALLY AND INSECTICIDALLY ACTIVE PYRAZOLIDINE COMPOUNDS

This is a division of Ser. No. 08/119,103, 35 USC 371 date Sep. 17, 1993, which is a national stage of PCT/EP 92/00452, filed Mar. 2, 1992.

The present invention relates to herbicidally, acaricidally and insecticidally active pyrazolidine-3,5-diones of the formula I, to processes for their preparation, and to novel intermediates for these processes. The invention furthermore relates to herbicidally, acaricidally or insecticidally active compositions as well as methods for controlling weeds, Acarina or insects.

The compounds according to the invention are those of the formula I

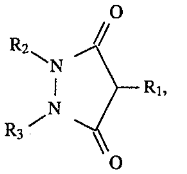

(I)

in which $R_1$ is

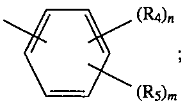

;

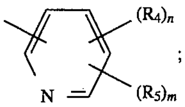

; or

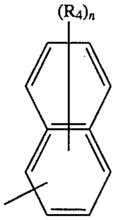

$R_2$ and $R_3$ independently of one another are $C_1$–$C_6$alkyl; $C_3$–$C_6$alkenyl; or $C_3$ -$C_6$alkynyl; or $R_2$ and $R_3$ together are a $-(CH_2)_3-$, $-(CH_2)_4-$, $-CH_2-CH=CH-CH_2-$, $-CH_2-CH=CH-$ or $-(CH_2)_2-CH=CH-$ bridge which is unsubstituted or up to trisubstituted by $C_1$–$C_4$alkyl;

n is 0; 1; 2; 3; or 4;

m is 0; or 1; the total of m and n being less than, or equal to, 4; the $R_4$ radicals independently of one another are halogen; nitro; cyano, $C_1$–$C_4$alkyl; $C_1$–$C_4$haloalkyl; $C_1$–$C_{10}$alkoxy; $C_1$–$C_4$haloalkoxy; $C_3$–$C_6$alkenyloxy; $C_1$–$C_4$alkoxy-$C_2$–$C_4$alkoxy; $C_3$–$C_6$alkynyloxy; $C_1$–$C_4$alkylcarbonyl; $C_1$–$C_4$alkoxycarbonyl; $C_1$–$C_4$alkylthio; $C_1$–$C_4$alkylsulfinyl; $C_1$–$C_4$ alkylsulfonyl; amino; mono-$C_1$–$C_4$alkylamino; di-$C_1$–$C_4$alkylamino;

$R_5$ is

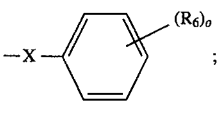

;

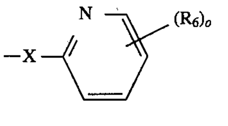

X is oxygen; sulfur; $CH_2$; or $NR_7$;

o is 0; 1; 2; or 3;

$R_6$ radicals independently of one another are $C_1$–$C_4$alkyl; halogen; $C_1$–$C_4$haloalkyl; $C_1$–$C_4$haloalkoxy; $C_1$–$C_4$alkoxy; nitro; cyano; $C_1$–$C_4$alkoxycarbonyl; amino; mono-$C_1$–$C_4$alkylamino; or di-$C_1$–$C_4$alkylamino; and $R_7$ is hydrogen; $C_1$–$C_4$alkyl; formyl; or $C_1$–$C_4$alkylcarbonyl;

or the acid addition salts thereof.

Suitable acids for forming such acid addition salts are both organic and inorganic acids. Examples of such acids are, inter alia, hydrochloric acid, hydrobromic acid, nitric acid, various phosphoric acids, sulfuric acid, acetic acid, propionic acid, butyric acid, valeric acid, oxalic acid, malonic acid, maleic acid, fumaric acid, lactic acid, tartaric acid or salicylic acid.

Because of their chemical constitution, the compounds of the formula I can exist in the tautomeric equilibrium forms I⇆I'⇆I":

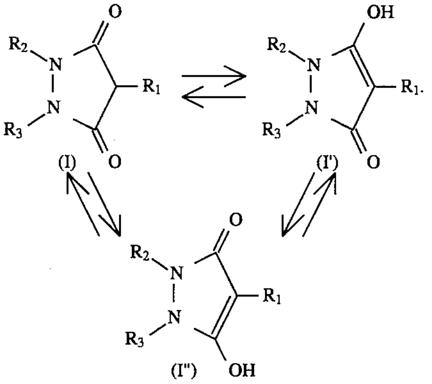

Moreover, certain substituents $R_1$ to $R_7$, on their own or in combination with each other or in combination with the skeleton to which they are bonded, can have centres of chirality.

The invention extends to the racemate as well as to the enriched and optically pure forms of the stereoisomers in question.

In the processes described in the present application, the asymmetrically substituted compounds of the formula I are generally obtained in the form of racemates, unless chiral educts are used. The stereoisomers can then be isolated by methods known per se, such as fractional crystallisation following salt formation with optically pure bases, acids or metal complexes, or, alternatively, by chromatographic methods on the basis of their physicochemical properties.

The compounds of the formula I in which the radicals $R_2$ and $R_3$ are alkyl, alkenyl or alkynyl radicals are derivatives of the pyrazolidine-3,5-dione system. In those cases in which $R_2$ and $R_3$ are a saturated or partially unsaturated $C_4$-carbon bridge, formula I is based on the ring system of the 1H-pyrazolo[1,2-a]pyridazine, and in those cases in which $R_2$ and $R_3$ are a saturated or partially unsaturated $C_3$-carbon bridge, it is based on the ring system of 1H,5H-pyrazolo[1,2-a]pyrazole. The individual ring positions are numbered analogously to Chemical Abstracts:

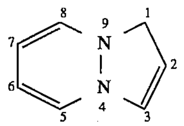

1H-pyrazolo[1,2-a]pyridazine

-continued

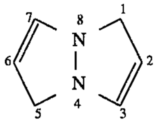

1H,5H-pyrazolo[1,2-a]pyrazole

Halogen in the above definitions is to be understood as meaning fluorine, chlorine, bromine and iodine, preferably fluorine and chlorine.

Monoalkylamino is, in particular, methylamino, ethylamino, n-propylamino, i-propylamino and the isomeric butylamino radicals.

Dialkylamino within the given limits of the definition is the radical which is substituted by identical as well as different alkyl radicals; in particular dimethylamino, methylethylamino, diethylamino, dibutylamino and diisopropylamino.

Alkyl is methyl, ethyl, isopropyl, n-propyl, n-butyl, isobutyl, sec-butyl, tert-butyl, as well as the isomeric pentyl and hexyl radicals.

Examples of haloalkyl are fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably the halogen-substituted methyl radicals such as dichlorochloromethyl, trifluoromethyl, difluoromethyl and dichloroflouromethyl.

Alkoxy is methoxy, ethoxy, propyloxy, i-propyloxy, n-butyloxy, i-butyloxy, s-butyloxy and t-butyloxy; preferably methoxy and ethoxy.

Examples of alkoxyalkoxy are methoxyethoxy, ethoxyethoxy, propoxyethoxy, isopropoxypropoxy or tert-butoxybutoxy.

Examples of haloalkoxy are fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably the halogen-substituted methoxy radicals such as difluoromethoxy and trifluoromethoxy.

Alkylthio is methylthio, ethylthio, propylthio, isopropylthio, n-butylthio, i-butylthio, s-butylthio, t-butylthio; preferably methylthio and ethylthio.

Alkylsulfinyl is methylsulfinyl, ethylsulfinyl, propylsulfinyl, isopropylsulfinyl, n-butylsulfinyl, i-butylsulfinyl, s-butylsulfinyl, t-butylsulfinyl; preferably methylsulfinyl and ethylsulfinyl.

Alkylsulfonyl is methylsulfonyl, ethylsulfonyl, propylsulfonyl, isopropylsulfonyl, n-butylsulfonyl, i-butylsulfonyl, s-butylsulfonyl, t-butylsulfonyl; preferably methylsulfonyl and ethylsulfonyl.

Alkenyl is to be understood as meaning straight-chain or branched alkenyl, such as allyl, methallyl, but-2-en-1-yl, pentenyl or 2-hexenyl. The alkenyl radicals are preferably bonded to the nitrogen hetero atom via a saturated carbon atom.

Alkynyl is to be understood as meaning straight-chain or branched alkynyl, such as propargyl, 1-methylprop-2-ynyl, but-2-yn-1-yl, or the isomeric pentynyl and 2-hexynyl radicals. The alkynyl radicals are preferably bonded to the nitrogen hetero atom via a saturated carbon atom.

Alkylcarbonyl is, in particular, acetyl and propionyl.

Alkoxycarbonyl is methoxycarbonyl, ethoxycarbonyl, propyloxycarbonyl, i-propyloxycarbonyl, n-butyloxycarbonyl, i-butyloxycarbonyl, s-butyloxycarbonyl and t-butyloxycarbonyl; preferably methoxycarbonyl and ethoxycarbonyl.

In those substituents which are composed of a plurality of basic elements the individual elements may be selected freely within the limits of the definition.

Preferred compounds of the formula I

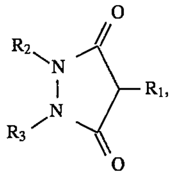

(I)

are those in which $R_1$ is

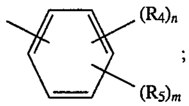

;

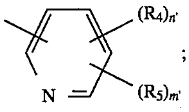

; or

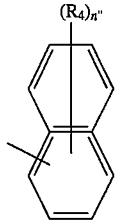

n is 0; 1; 2; 3; or 4;

m is 0; or 1; and the total of m and n is less than, or equal to, 4;

n' is 0; 1; 2; or 3;

n" is 0; 1; or 2;

m' is 0; or 1; and the total of m' and n' is less than, or equal to, 3; and the radicals $R_1$ to $R_5$ are as defined above.

Other preferred compounds are pyrazolidine-3,5-diones of the formula I

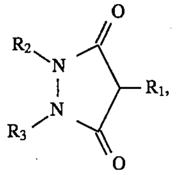

(I)

in which $R_1$ is

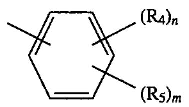

or

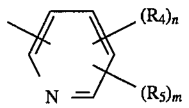

$R_2$ and $R_3$ independently of one another are $C_1$–$C_6$alkyl; $C_3$–$C_6$ alkenyl; or $C_3$–$C_6$alkynyl; or $R_2$ and $R_3$ together are a $—(CH_2)_3—$, $—(CH_2)_4—$, $—CH_2—CH{=}CH—CH_2—$, $—CH_2—CH{=}CH—$ or $—(CH_2)_2—CH{=}CH—$ bridge which is unsubstituted or up to trisubstituted by $C_1$–$C_4$alkyl;

n is 0; 1; 2; 3; or 4;

m is 0; or 1; the total of m and n being less than, or equal to, 4; the $R_4$ radicals independently of one another are halogen; nitro; cyano; $C_1$–$C_4$alkyl; $C_{1-C4}$haloalkyl; $C_1$–$C_{10}$alkoxy; $C_1$–$C_4$haloalkoxy; $C_3$–$C_6$alkenyloxy; $C_3$–$C_6$alkynyloxy; $C_1$–$C_4$alkylcarbonyl; $C_1$–$C_4$alkoxycarbonyl; $C_1$–$C_4$alkylthio; $C_1$–$C_4$alkylsulfinyl; $C_1$–$C_4$alkylsulfonyl; amino; mono-$C_1$–$C_4$alkylamino; di-$C_1$–$C_4$alkylamino;

$R_5$ is

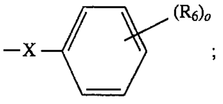

X is oxygen; sulfur; $CH_2$; or $NR_7$;

o is 0; 1; 2; or 3;

$R_6$ radicals independently of one another are $C_1$–$C_4$alkyl; halogen; $C_1$–$C_4$haloalkyl; $C_1$–$C_4$haloalkoxy; $C_1$–$C_4$alkoxy; nitro; cyano; $C_1$–$C_4$alkoxycarbonyl; amino; mono-$C_1$–$C_4$alkylamino; or di-$C_1$–$C_4$alkylamino; and $R_7$ is hydrogen; $C_1$–$C_4$alkyl; formyl; or $C_1$–$C_4$alkylcarbonyl, where a preferred meaning in this group is that of the compounds of the formula I (I)

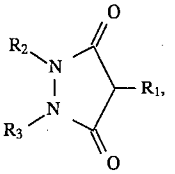

in which $R_1$ is

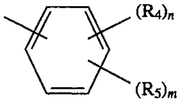

or

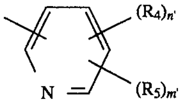

n is 0; 1; 2; or 3;

m is 0; or 1; and the total of m and n is less than, or equal to, 4;

n' is 0; 1; 2; or 3;

m' is 0; or 1; and the total of m' and n' is less than, or equal to, 3;

and the radicals $R_2$ to $R_5$ are as defined above.

In particular, the present invention relates to:

5,6,7,8-tetrahydro-1H-pyrazolo[1,2-a]pyridazine-1,3(2H)-diones of the formula Ia (Ia)

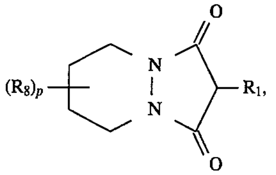

in which $R_1$ is as defined above;

$R_8$ is $C_1$–$C_4$alkyl; and p is 0, 1, 2 or 3, preferably 0;

5,8-dihydro-1H-pyrazolo[1,2-a]pyridazine-1,3(2H)-diones of the formula Ib (Ib)

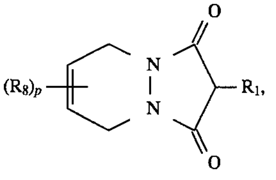

in which $R_1$ is as defined above;

$R_8$ is $C_1$–$C_4$alkyl; and p is 0, 1, or 2, preferably 0;

7,8-dihydro-1H-pyrazolo[1,2-a]pyridazine-1,3(2H)-diones of the formula Ic (Ic)

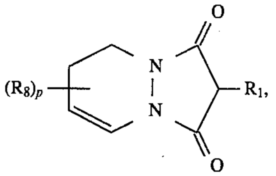

in which $R_1$ is as defined above;

$R_8$ is $C_1$–$C_4$alkyl; and p is 0, 1, 2 or 3, preferably 0;

6,7-dihydro-1H,5H-pyrazolo[1,2-a]pyrazole-1,3(2H)-diones of the formula Id (Id)

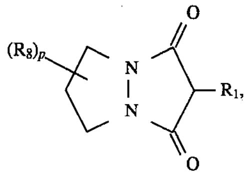

in which $R_1$ is as defined above;

$R_8$ is $C_1$–$C_4$alkyl; and p is 0, 1, 2 or 3, preferably 0;

1H,5H-pyrazolo[1,2-a]pyrazole-1,3(2H)-diones of the formula Ie (Ie)

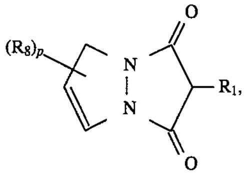

in which $R_1$ is as defined above;

$R_8$ is $C_1$–$C_4$alkyl; and p is 0, 1, 2 or 3, preferably 0;

pyrazolidine-1,3-diones of the formula If (If)

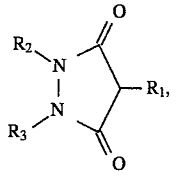

in which $R_1$ is as defined above;

and $R_2$ and $R_3$ independently of one another are $C_1$–$C_6$alkyl; $C_3$–$C_6$alkenyl; or $C_3$–$C_6$alkynyl;

pyrazolidine-1,3-diones of the formula Ig (Ig)

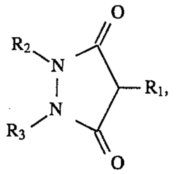

in which $R_1$ is as defined above;

and $R_2$ and $R_3$ independently of one another are $C_1$–$C_6$alkyl; or $C_3$–$C_6$alkenyl; and pyrazolidine-1,3-diones of the formula Ih

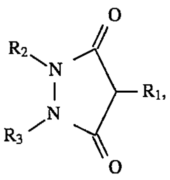

(Ih)

in which $R_1$ is as defined above;

and $R_2$ and $R_3$ are $C_1$–$C_6$alkyl.

Particularly preferred compounds are those of the formula I or of the formulae Ia to Ih in which $R_1$ is

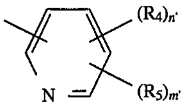

and n' is 0; 1; 2; or 3;

m' is 0; or 1; and the total of m' and n' is less than, or equal to, 3;

$R_4$ is not more than three times halogen; or $C_1$–$C_4$alkyl; not more than twice $C_1$–$C_4$alkoxy; $C_1$–$C_4$haloalkoxy; $C_1$–$C_4$alkylthio; $C_1$–$C_4$alkylsulfinyl; $C_1$–$C_4$alkylsulfonyl; amino; mono-$C_1$–$C_4$alkylamino; di-$C_1$–$C_4$alkylamino; or $C_1$–$C_4$haloalkyl; and not more than once nitro; cyano; $C_1$–$C_4$alkylcarbonyl; $C_1$–$C_4$alkoxycarbonyl;

or $R_1$ is

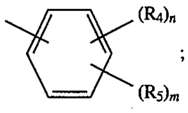

;

n is 0; 1; 2; 3; or 4;

m is 0; or 1; and the total of m and n is less than, or equal to, 4;

$R_4$ is not more than four times halogen; or $C_1$–$C_4$alkyl; not more than three times $C_1$–$C_{10}$alkoxy; $C_1$–$C_4$haloalkoxy; or $C_1$–$C_4$alkylthio; and not more than twice nitro; $C_1$–$C_4$alkylsulfinyl; $C_1$–$C_4$alkylsulfonyl; amino; mono-$C_1$–$C_4$alkylamino; di-$C_1$–$C_4$alkylamino; $C_1$–$C_4$haloalkyl; or cyano; not more than once $C_1$–$C_4$alkylcarbonyl; $C_3$–$C_6$alkenyloxy; $C_3$–$C_6$alkynyloxy; $C_1$–$C_4$alkoxycarbonyl; $C_1$–$C_4$alkoxy-$C_2$–$C_4$alkoxy; and $R_2$, $R_3$ and $R_5$ are as defined above, and the meaning of the substituent $R_4$ can in each case be identical or different.

Compounds of the formula I or of the formulae Ia to Ih which must be emphasised are those in which $R_1$ is

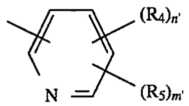

and n' is 0; 1; 2; or 3;

m' is 0;

$R_4$ is not more than three times halogen; or $C_1$–$C_4$alkyl; not more than twice $C_1$–$C_4$alkoxy; $C_1$–$C_4$haloalkyl; $C_1$–$C_4$haloalkoxy; $C_1$–$C_4$alkylthio; $C_1$–$C_4$alkylsulfinyl; $C_1$–$C_4$alkylsulfonyl; amino; mono-$C_1$–$C_4$alkylamino; or di-$C_1$–$C_4$alkylamino; and not more than once nitro; cyano; $C_1$–$C_4$alkylcarbonyl; $C_1$–$C_4$alkoxycarbonyl;

or $R_1$ is

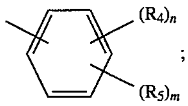

;

n is 0; 1; 2; or 3;

m is 0; or 1; and the total of m and n is less than, or equal to, 3;

$R_4$ is not more than three times fluorine; chlorine; or $C_1$–$C_4$alkyl; not more than twice $C_1$–$C_4$alkoxy; $C_1$–$C_4$haloalkyl; $C_1$–$C_4$haloalkoxy; or $C_1$–$C_4$alkylthio; and not more than once nitro; $C_1$–$C_4$alkylsulfinyl; $C_1$–$C_4$alkylsulfonyl; amino; mono-$C_1$–$C_4$alkylamino; di-$C_1$–$C_4$alkylamino; cyano; $C_1$–$C_4$alkylcarbonyl; $C_3$–$C_6$alkenyloxy; $C_3$–$C_6$alkynyloxy; or $C_1$–$C_4$alkoxycarbonyl; and $R_2$, $R_3$ and $R_5$ are as defined above, and the meaning of the substituent $R_4$ can in each case be identical or different.

Other compounds which must be emphasised are those of the formulae Ia to Ih in which $R_1$ is

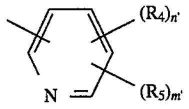

and n' is 0; 1; 2; or 3;

m' is 0;

$R_4$ is not more than three times fluorine; chlorine; or $C_1$–$C_2$alkyl; not more than twice $C_1$–$C_2$alkoxy; $C_1$–$C_2$haloalkyl; $C_1$–$C_2$haloalkoxy; $C_1$–$C_2$alkylthio; $C_1$–$C_2$alkylsulfinyl; $C_1$–$C_2$alkylsulfonyl; amino; mono-$C_1$–$C_2$alkylamino; or di-$C_1$–$C_2$alkylamino; and not more than once nitro; cyano; $C_1$–$C_2$alkylcarbonyl; $C_1$–$C_2$alkoxycarbonyl;

or $R_1$ is

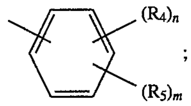

;

n is 0; 1; 2; or 3;

m is 0; or 1; and the total of m and n is less than, or equal to, 3;

$R_4$ is not more than three times fluorine; chlorine; or $C_1$–$C_4$alkyl; not more than twice $C_1$–$C_2$alkoxy; $C_1$–$C_2$haloalkyl; $C_1$–$C_2$haloalkoxy; or $C_1$–$C_2$alkylthio; and not more than once nitro; $C_1$–$C_2$alkylsulfinyl; $C_1$–$C_2$alkylsulfonyl; amino; mono-$C_1$–$C_2$alkylamino; di-$C_1$–$C_2$alkylamino; cyano; $C_1$–$C_2$alkylcarbonyl; $C_1$–$C_2$alkoxycarbonyl; and $R_2$, $R_3$ and $R_5$ are as defined above, and the meaning of the substituent $R_4$ can in each case be identical or different.

Further preferred compounds with regard to the insecticidal and acaricidal action are the following pyrazolidine-3,5-diones of the formula I

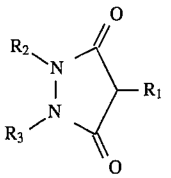

(I)

in which the following groups can be $R_1$

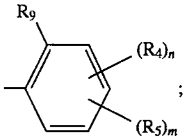

;

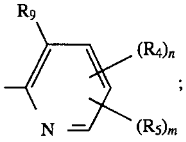

;

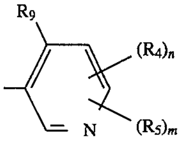

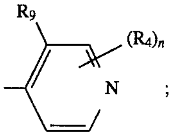

;

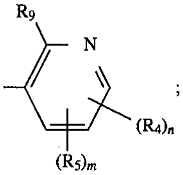

;

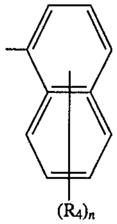

in which $R_2$, $R_3$, $R_4$, $R_5$, m and n have the abovementioned meaning and $R_9$ is halogen, $C_1$–$C_4$alkyl or $C_1$–$C_4$haloalkyl, the total m+n being less than, or equal to, 3.

In this context, pyrazolidine-3,5-diones of the formula I which must be particularly emphasised are those in which $R_2$ is methyl and $R_3$ is methyl or ethyl, or $R_2$ and $R_3$ together are $$-(CH_2)_3-,\quad -(CH_2)_4-\quad \text{or}\quad -CH_2-CH(CH_3)-CH(CH_3)-CH_2.$$

Pyrazolidine-3,5-diones of the formula I which must be particularly emphasised are furthermore those in which $R_1$ can be the following group:

$R_1$ is

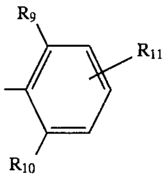

or 2-naphthyl in which $R_9$ is halogen; $C_1$–$C_4$alkyl; $C_1$–$C_4$haloalkyl;

$R_{10}$ is hydrogen; halogen; $C_1$–$C_4$alkyl; $C_1$–$C_4$haloalkyl $R_{11}$ is hydrogen; halogen or $C_1$–$C_4$alkyl.

Particularly important in this sub-group are the pyrazolidine-3,5-diones, in which $R_2$ is methyl, $R_3$ is methyl or ethyl, or $R_2$ and $R_3$ together are $-(CH_2)_3-$, $-(CH_2)_4-$ or $$-(CH_2)_3-,\quad -(CH_2)_4-\quad \text{or}\quad -CH_2-CH(CH_3)-CH(CH_3)-CH_2$$

and $R_1$ is 2-naphthyl or

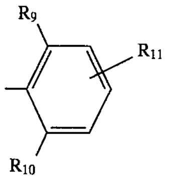

in which, $R_9$ is chlorine; $C_1$–$C_2$alkyl; $C_1$–$C_2$haloalkyl;

$R_{10}$ is hydrogen; chlorine; fluorine; $C_1$–$C_2$alkyl or $C_1$–$C_2$haloalkyl; and $R_{11}$ is hydrogen; fluorine; chlorine or methyl.

Individual compounds which may be mentioned are:

2-(phenyl)-5,6,7,8-tetrahydro-1H-pyrazolo[1,2-a]pyridazine-1,3(2H)-dione (Comp. No. 1.001), 2-(2-methylphenyl)-5,6,7,8-tetrahydro-1H-pyrazolo[1,2-a] pyridazine-1,3(2H)-dione (Comp. No. 1.002), 2-(4-methylphenyl)-5,6,7,8-tetrahydro-1H-pyrazolo[1,2-a] pyridazine-1,3(2H)-dione (Comp. No. 1.003), 2-(2,4,6-trimethylphenyl)-5,6,7,8-tetrahydro-1H-pyrazolo [1,2-a]pyridazine-1,3(2H)-dione (Comp. No. 1.010), 2-(4-chlorophenyl)-5,6,7,8-tetrahydro-1H-pyrazolo[1,2-a] pyridazine-1,3(2H)-dione (Comp. No. 1.013), 2-(2,4-dichlorophenyl)-5,6,7,8-tetrahydro-1H-pyrazolo[1,2-a]pyridazine-1,3(2H)-dione (Comp. No. 1.014) and 2-(2,6-dichlorophenyl)-5,6,7,8-tetrahydro-1H-pyrazolo[1,2-a]pyridazine-1,3(2H)-dione, (Comp. No. 1.015), 2-(2,4-dimethylphenyl)-5,6,7,8-tetrahydro-1H-pyrazolo[1,2-a]pyridazine-1,3(2H)-dione, (Comp. No. 1.004), 2-(2-chlorophenyl)-5,6,7,8-tetrahydro-1H-pyrazolo[1,2-a] pyridazine-1,3(2H)-dione, (Comp. No. 1.012), 2-(2-chloro-6-fluorophenyl)-5,6,7,8-tetrahydro-1H-pyrazolo[1,2-a]pyridazine-1,3(2 H)-dione, (Comp. No. 1.016), 1,2-dimethyl-4-(2,4,6-trimethylphenyl)-3,5-pyrazolidinedione, (Comp. No. 10.010) in particular 2-(2,4,6-Trimethylphenyl)-5,6,7,8-tetrahydro-1H-pyrazolo[1,2-a]-pyridazine-1,3 (2H)-dione (Comp. No. 1.010).

The compounds of the formula I are novel. They can be prepared by a) cyclisation of a hydrazinecarboxylate of the formula II,

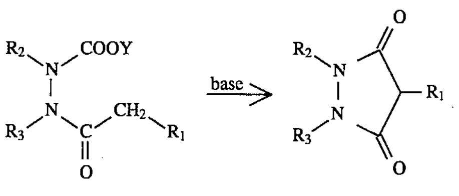

(II) (I)

in which $R_1$, $R_2$ and $R_3$ are as defined above and Y is $C_1$–$C_6$alkyl, phenyl or benzyl;

b) condensation of a malonic acid derivative of the formula III, in which $R_1$ is as defined above, with a hydrazine derivative of the formula IV, in which $R_2$ and $R_3$ are as defined above,

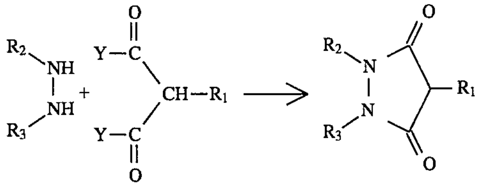

(IV) (III) (I)

and in which Y is OH, halogen or $C_1$–$C_4$alkoxy; or c) the reaction of a pyrazolidine-3,5-dione of the formula XXXIV

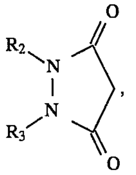

(XXXIV)

in which the radicals $R_2$ and $R_3$ are as defined above, with a compound of the formula XXXV

X—$R_1$ (XXXV), in which X and $R_1$ are as defined above, in the presence of a base or, if desired, in the presence of Cu(I) or of a Pd catalyst.

Reactions a), b), and c) are carried out analogously to processes known from the literature (N. R. El-Rayyes in Synthesis, 1985, 1028 et seq.), preferably in a solvent which is inert during the reaction. U.S. Pat. No. 4,128,425 and J. Chem. Soc. Perkin Trans. I, 1987, 877 refer to processes for the preparation of the starting compounds (XXXIV).

Suitable bases for the cyclocondensation reaction a) are, in particular, sodium hydride, sodium amide, phenyllithium or potassium tert.-butylate.

The compounds of the formulae Ic and Ie,

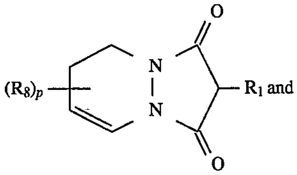

(Ic)

and

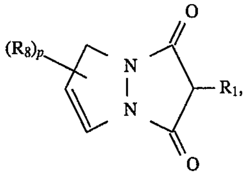

(Ie)

in which $R_1$, $R_8$ and p are as defined above, can be prepared by reacting an alcohol of the formula XIII,

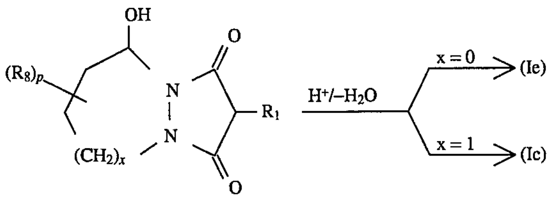

(XIII)

in which x is 0 or 1, in the presence of acid to give Ic or Ie.

A further process allows the pyrazolidine-1,3-diones of the formula If

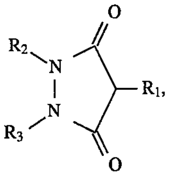

(If)

in which $R_1$ is as defined above and $R_2$ and $R_3$ independently of one another are $C_1$–$C_6$alkyl, $C_3$–$C_6$alkenyl or $C_3$–$C_6$alkynyl, to be obtained by acylating a hydrazone of the formula XIV in which $R_2$ is as defined above and the radical

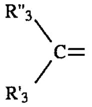

is a $C_1$–$C_6$alkylidene, $C_1$–$C_6$alkenylidene or $C_1$–$C_6$alkynylidene radical, with a chloroformate IX in which Y is $C_1$–$C_4$alkyl, to give the N-acylhydrazone XV,

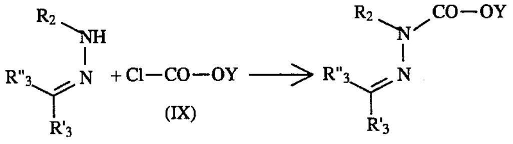

(XIV) (IX) (XV)

and subsequently acylating the N-acylhydrazone with arylacetyl halide of the formula X in which $R_1$ is as defined above and Z is chlorine or bromine, to give a hydrazine of the formula XVI,

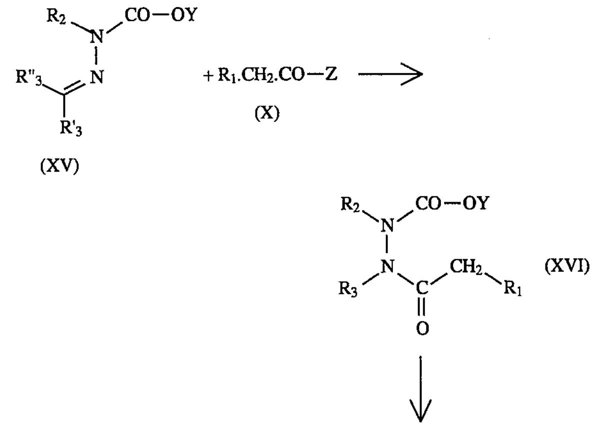

(XV) (X) (XVI) (If)

and subsequently cyclising the hydrazine of the formula XVI in the presence of bases to give the pyrazolidine-1,3-dione of the formula If.

This process can be carried out analogously to the process known from EP-A-0 304 920 and Zh. Org. Khim. 4, (1968) p. 968.

The compounds of the formula II are valuable intermediates for the synthesis of the end products of the formula I according to the invention. The novel compounds of the formula II, processes for their preparation and novel starting compounds which are suitable for these processes are a further subject of the present invention.

The compounds of the formula II can be obtained by N-acylation of the N-acylhydrazines of the formula XVII in which $R_2$ and $R_3$ are as defined above and Y is $C_1$–$C_4$alkyl, with arylacetyl halides of the formula X in which $R_1$ is as defined above and Z is chlorine or bromine,

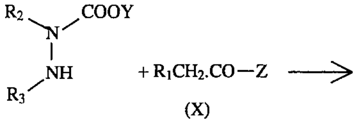

(XVII) (X)

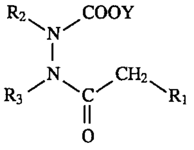

(II)

in analogy to processes known from the literature (Chem. Rev. 52 (1953), 237–416).

The compounds of the formula XVI

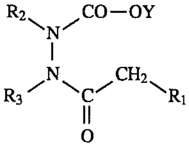

(XVI)

in which $R_1$ is as defined above, Y is $C_1$–$C_4$alkyl and $R_2$ and $R_3$ independently of one another are $C_1$–$C_6$alkyl, $C_3$–$C_6$alkenyl or $C_3$–$C_6$alkynyl, can be prepared by acylating a hydrazone of the formula XIV in which $R_2$ is as defined above and the radical

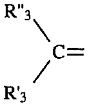

is a $C_1$–$C_6$alkylidene, $C_1$–$C_6$alkenylidene or $C_1$–$C_6$alkynylidene radical, with a chloroformate IX in which Y is $C_1$–$C_4$alkyl, to give the N-acylhydrazone XV,

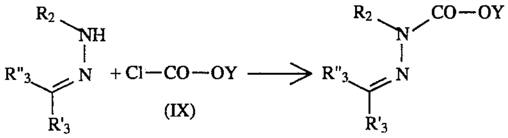

(IX)

(XIV) (XV)

and subsequently acylating the N-acylhydrazone with an arylacetic halide of the formula X in which $R_1$ is as defined above and Z is chlorine or bromine, to give a hydrazine of the formula XVI

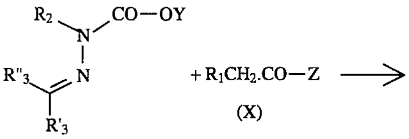

(XV) (X)

-continued

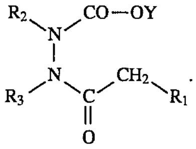

(XVI)

Alcohols of the formula XIII' can be prepared by hydrogenating a dihydropyridazin-(2H)3-one of the formula V, in which $R_8$ and p are as defined above, to give a tetrahydropyridazin-(2H)3-one VI and subsequently acylating the product with a chloroformate (IX), in which Y is $C_1$–$C_4$alkyl, to give a tetrahydropyridazin-(2H)3-one VII

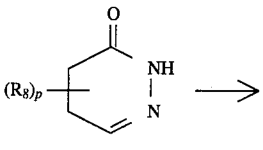

(V)

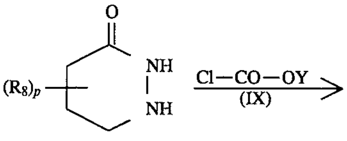

(VI)

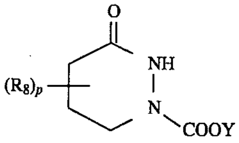

(VII)

and acylating the product obtained in this manner with an arylacetyl halide of the formula X in which $R_1$ is as defined above and Z is chlorine or bromine, to give a tetrahydropyridazin-(2H)3-one of the formula XI,

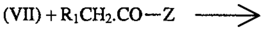

(X)

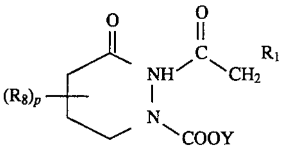

(XI)

then cyclising the tetrahydropyridazin-(2H)3-one XI in the presence of a base to give the pyrazolo[1,2-a]pyridazine XII and reducing this product with a hydrogenating agent, preferably sodium borohydride, to give the alcohol XIII'

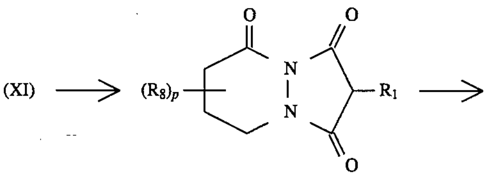

(XII)

-continued

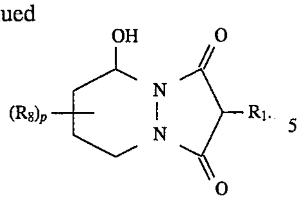

(XIII', x = 1)

-continued

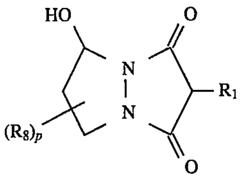

(XIII''/x = 0)

The alcohols XIII'' can be obtained in an analogous manner by acylating a pyrazolidine-3-one (XVIII) in which $R_8$ and p are as defined above, with a chloroformate of the formula (IX) in which Y is $C_1$–$C_4$alkyl, to give the compound (XIX)

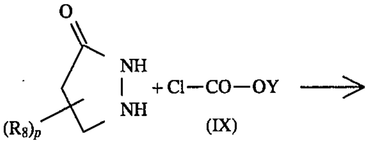

(XVIII) (IX)

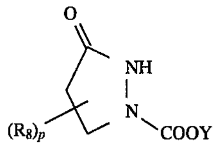

(XIX)

and acylating the product obtained in this manner with an arylacetyl halide of the formula X in which $R_1$ is as defined above and Z is chlorine or bromine, to give a pyrazolidin-3-one of the formula XX, $(XIX) + R_1CH_2.CO-Z \longrightarrow$ (X)

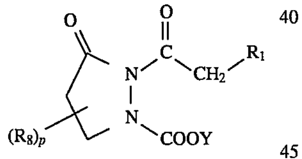

(XX)

then cyclising the diacylated pyrazolidin-3-one XX in the presence of a base to give the pyrazolo[1,2-a]pyrazole XXI and reducing this product with a hydrogenating agent, preferably sodium borohydride, to give the alcohol XIII'',

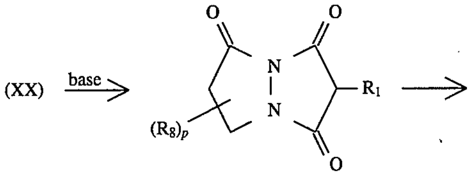

(XXI)

The N-acyl hydrazines of the formula XVII can be obtained by hydrolysis and decarboxylation of the hydrazinedicarboxylate XXII in which $R_2$ and $R_3$ are as defined above and Y is $C_1$–$C_4$alkyl,

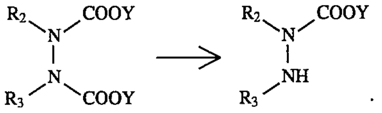

(XXII) (XVII)

The tetrahydropyridazinecarboxylates XXIII,

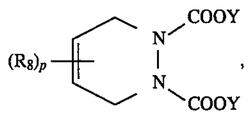

(XXIII)

in which $R_8$ and p are as defined above and Y is $C_1$–$C_4$alkyl can furthermore be prepared by reacting a diene of the formula XXIV, in which $R_8$ and p are as defined above, with an azodicarboxylate of the formula XXV, in which Y is $C_1$–$C_4$alkyl

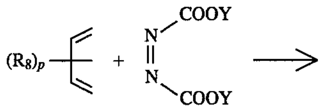

(XXIII).

(XXIV) (XXV)

The compounds of the formula XXIII can subsequently be processed analogously to processes known from the literature (Coll. Czech. Chem. Commun. 33 (1968) 2087; Bull. Soc. Chim. France (1957) 704; EP-A-0 304 920 or Beilsteins Handbuch der Organischen Chemie [Manual of Organic Chemistry], Vol. $23^{III/IV}$, 465) according to equation 1 below by hydrolysis and decarboxylation to give the tetrahydropyridazinecarboxylates XXVI, or by reduction, hydrolysis and decarboxylation via the diesters XXVII to give the hexahydropyridazines XXVIII.

EQUATION 1

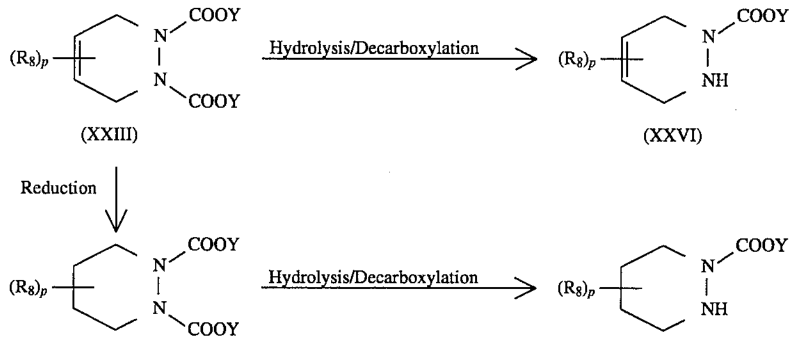

(XXIII) (XXVI) (XXVII) (XXVIII)

A further access route for the pyrazole- or pyridazinecarboxylates of the formula XXIX in which $R_8$ and p are as defined above and Y is $C_1$–$C_4$alkyl and n is 1 or 2, is the reaction of an α,ω-dihalo compound of the formula XXX in which $R_8$ and p are as defined above, Hal is halogen, preferably chlorine or bromine, and n is 1 or 2, with N,N'-hydrazinedicarboxylate XXXI in which Y is $C_1$–$C_4$alkyl, according to reaction equation 2.

EQUATION 2

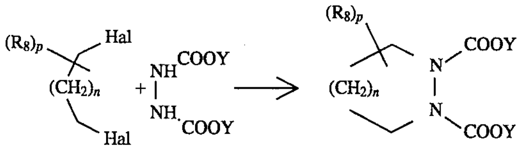

(XXX) (XXXI) (XXIX)

The arylacetyl halides of the formula X are generally known or can be prepared from the corresponding arylacetic acids analogously to processes known from the literature. The following syntheses are particularly suitable for the preparation of the arylacetic acids:

a) reaction of acetylaryl compounds in the sense of a Wilgerodt or Wilgerodt-Kindler reaction to give the corresponding arylacetamides, arylammonium salts or arylthioamides, followed by hydrolysis to give the arylacetic acids (E. V. Brown in Synthesis 1975, 358 et seq.).

b) reaction in the sense of a Darzens reaction of suitably substituted arylaldehydes following Darzens method using using ethyl chloroacetate to give arylacetaldehydes, followed by oxidation to give the corresponding arylacetic acids (Ballester, Chem, Rev. 55 (1955) 283 et seq.).

c) rearrangement of the α-haloalkyl aryl ketones XXXII or α-haloalkyl aryl ketals XXXIII; in which $R_1$ is as defined above and Hal is halogen, using processes known from the literature by zinc bromide catalysis (Synthesis, 1985, 436 or Angew. Chem. 1984, 413) to give the esters $R_1CH_2COO$—R' which can subsequently be hydrolysed to the corresponding arylacetic acids.

$$R_1{-}CO{-}CH_2\text{-}Hal \xrightarrow[R'OH]{ZnBr_2} R_1{-}CH_2{-}CO_2{-}R'$$

(XXXII)

$$R_1{-}C(OR')_2{-}CH_2\text{-}Hal \xrightarrow{\text{cat. } ZnBr_2} R_1{-}CH_2{-}CO_2{-}R'$$

(XXXIII)

d) hydrolysis of arylacetyl cyanides analogously to processes known from the literature (DE-A-3 416 772).

e) reaction of aryl halides with malonic acid derivatives, phenylsulfonylacetonitriles or cyanoacetates analogously to processes known from the literature with Pd catalysis (Synthesis 1993, 67; Synthesis 1985, 506 or Chem. Lett. 1987, 887).

The compounds of the formulae II, XIII, XIV, XV, XVI, VII, XI, XII, XIX, XX, XXI, XIII", XXIII, XXVI, XXVII, XXVIII and XXIX are valuable intermediates for the preparation of the compounds of the formula I according to the invention. The invention also relates to the novel compounds of the formulae II, XIII, XIV, XV, XVI, VII, XI, XII, XIX, XX, XXI, XIII", XXIII, XXVI, XXVII, XXVIII and XXIX, to processes for their preparation, and to their use as intermediates.

The compounds of the formula I are herbicidally active. As herbicides, the active ingredients of the formula I are generally used successfully at rates of application of 0.001 to 5 kg/ha, in particular 0.005 to 3 kg/ha. The dosage rate required for the desired action can be determined by experiments. It depends on the type of action, the development stage of the crop plant and of the weed, as well as on the application (location, time, method) and, due to these parameters, can vary within wide ranges.

When used at low rates of application, the compounds of the formula I are distinguished by growth-inhibiting and selectively herbicidal properties which make them outstandingly suitable for use in crops of useful plants, in particular in cereals, cotton, soybeans, rapeseed oil, maize and rice.

It has now been found that the compounds of the formula I according to the invention are valuable active ingredients in pest control while being well tolerated by warm-blooded species, fish and plants. The application of the active ingredients according to the invention particularly relates to insects and arachnids which can be found in useful plants and ornamentals in agriculture, in particular in cotton, vegetable and fruit crops, in the forest, in the protection of stored goods and materials as well as in the hygiene field, in particular on domestic animals and productive livestock.

They are active against all or individual stages of development of normally sensitive, but also resistant, species. In this context, they may unfold their activity through immediate destruction of the pests or only after some time, for example during moulting, or through reduced oviposition and/or hatching rate. The abovementioned pests include:

from the order Lepidoptera, for example

*Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis, Chilo spp., Choristoneura spp., Clysia ambiguella, Cnaphalocrocis spp., Cnephasia spp., Cochylis spp., Coleophora spp., Crocidolomia binotalis, Cryptophlebia leucotreta, Cydia spp., Diatraea spp., Diparopsis castanea, Earias spp., Ephestia spp., Eucosma spp., Eupoecilia ambiguella, Euproctis spp., Euxoa spp., Grapholita spp., Hedya nubiferana, Heliothis spp., Hellula undalis, Hyphantria cunea, Keiferia lycopersicella, Leucoptera scitella, Lithocollethis spp., Lobesia botrana, Lymantria spp., Lyonetia spp., Malacosoma spp., Mamestra brassicae, Manduca sexta, Operophtera spp., Ostrinia nubilalis, Pammene spp., Pandemis spp., Panolis flammea, Pectinophora gossypiella, Phthorimaea opercullella, Pieris rapae, Pieris spp., Plutella xylostella, Prays spp., Scirpophaga spp., Sesamia spp., Sparganothis spp., Spodoptera spp., Synanthedon spp., Thaumetopoea spp., Tortrix spp., Trichoplusia ni* and *Yponomeuta spp.;* from the order of the Coleoptera, for example

*Agriotes spp., Anthonomus spp., Atomaria linearis, Chaetocnema tibialis, Cosmopolites spp., Curculio spp., Dermestes spp.,Diabrotica spp., Epilachna spp., Eremnus spp., Leptinotarsa decemlineata, Lissorhoptrus spp. Melolontha spp., Orycaephalus spp., Otiorhynchus spp., Phylctinus spp., Popilia spp., Psylliodes spp., Rhizopertha spp.,* Scarabeidae, *Sitophilus spp., Sitotroga spp., Tenebrio spp., Tribolium spp.* and *Trogoderma spp.;* from the order of the Orthoptera, for example

*Blatta spp., Blattella spp., Gryllotalpa spp., Leucophaea maderae, Locusta spp., Periplaneta spp.* and *Schistocerca spp.;* from the order of the Isoptera, for example

*Reticulitermes spp.;* from the order of the Psocoptera, for example

*Liposcelis spp.;* from the order of the Anoplura, for example

*Haematopinus spp., Linognathus spp. Pediculus spp., Pemphigus spp.* and *Phylloxera spp.;* from the order of the Mallophaga, for example

*Damalinea spp.* and *Trichodectes spp.;* from the order of the Thysanoptera, for example

*Frankliniella spp., Hercinothrips spp., Taeniothrips spp., Thrips palmi, Thrips tabaci* and *Scirtothrips aurantii;* from the order of the Heteroptera, for example

*Cimex spp., Distantiella theobroma, Dysdercus spp., Euchistus spp. Eurygaster spp. Leptocorisa spp., Nezara spp., Piesma spp., Rhodnius spp., Sahlbergella singularis, Scotinophara spp.* and *Triatoma spp.;* from the order of the Homoptera, for example

*Aleurothrixus floccosus, Aleyrodes brassicae, Aonidiella spp.,* Aphididae, *Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae* and *Unaspis citri;* from the order of the Hymenoptera, for example

Acromyrmex, *Atta spp., Cephus spp., Diprion spp.,* Diprionidae, *Gilpinia polytoma, Hoplocampa spp., Lasius spp., Monomorium pharaonis, Neodiprion spp., Solenopsis spp.* and *Vespa spp.;* from the order of the Diptera, for example

*Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp. Oscinella frit, Pegomyia hyoscyami, Phorbia spp., Rhagoletis pomonella, Sciara spp., Stomoxys spp., Tabanus spp., Tannia spp.* and *Tipula spp.;* from the order of the Siphonaptera, for example

*Ceratophyllus spp., Xenopsylla cheopis,* from the order of the Acarina, for example

*Acarus siro, Aceria sheldoni, Aculus schlechtendali, Amblyomma spp., Argas spp., Boophilus spp., Brevipalpus spp., Bryobia praetiosa, Calipitrimerus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp.* and *Tetranychus spp.;* and from the order of the Thysanura, for example

*Lepisma saccharina.*

The compounds are particularly suitable for controlling pests in cotton, fruit, rice and vegetable crops. Pests which are controlled are, in particular, those from the order Acarina, for example spider mites such as *Tetranychus urticae* and *Panonychus ulmi,* or ticks such as *Boophilus spp.*

As insecticides and acaricides, the active ingredients of the formula I are generally used at concentrations between 0.1 and 1000 ppm, preferably between 0.1 and 500 ppm. The rates of application per hectare are generally 1 to 2000 g of active ingredient per hectare, preferably 10 to 10000 g/ha, in particular 20 to 600 g/ha. The level of rates and concentrations of application for achieving an insecticidal and acaricidal pest control effect is much lower than is the case when these active ingredients are used as herbicides. This means that damage of the treated useful plants is not possible when the active ingredients of the formula I are used as insecticides/acaricides within the teaching according to the invention.

The good pesticidal activity of the compounds of the formula I according to the invention corresponds to a mortality rate of at least 50–60% of the abovementioned pests.

The effectiveness of the compounds according to the invention and of the compositions containing them can be substantially widened and adapted to the prevailing circumstances by adding other insecticides and/or acaricides. Examples of suitable additional substances are representatives from the following classes of active ingredients: organophosphorus compounds, nitrophenols and derivatives, formamidines, ureas, carbamates, pyrethroids, chlorinated hydrocarbons and *Bacillus thuringiensis* preparations.

The compounds of the formula I are used in unaltered form or, preferably, together with the auxiliaries conventionally used in the art of formulation, and they can therefore be processed in a known manner to give emulsifiable concentrates, directly sprayable or dilutable solutions, dilute emulsions, wettable powders, soluble powders, dusts, granules and also encapsulations in polymeric substances. The methods of application such as spraying, atomising, dusting, scattering or pouring, as well as the compositions, are selected to suit the intended aims and the prevailing circumstances. The compounds of the formula I are furthermore also suitable for use in the treatment of seed. In this context, the seed can be treated or dressed with the active ingredient or with a formulation containing the active ingredient prior to sowing, and the active ingredient can be applied to the furrow during sowing.

i) Seed Dressing a) The seeds are dressed with an active ingredient formulated as a wettable powder by shaking them in a container until the formulation is distributed evenly on the seed surface (dry dressing). Up to 4 g of active ingredient of the formula I are used (in the case of a 50% formulation: up to 8.0 g of wettable powder) per kg of seed.

b) The seeds are dressed with an emulsion concentrate of the active ingredient or with an aqueous solution of the active ingredient of the formula I which has been formulated as a wettable powder, following method a) (wet dressing).

c) The seed is dressed by being immersed for 1 to 72 hours in a liquor containing up to 1000 ppm of active ingredient of the formula I and, if appropriate, the seeds are then dried (seed soaking).

Naturally, seed dressing or treatment of the germinated seedling are preferred methods of application because the treatment with active ingredient is completely directed towards the target crop. As a rule, 4.0 g to 0.001 g of active substance are used per kg of seed, but it is possible to exceed, or remain under, the concentration limits given, depending on the method used, which also allows the addition of other active ingredients or micronutrients (repeated dressing).

ii) Controlled Release of Active Ingredients

A solution of the active ingredient is applied to mineral granule carriers or polymerised granules (urea/formaldehyde) and allowed to dry. If appropriate, a coating can be applied (coated granules) which allows metered release of the active ingredient over a certain period.

The compounds of the formula I are employed in unaltered form or, preferably, as compositions together with the auxiliaries conventionally used in the art of formulation, and they are therefore processed in a known manner to give, for example, emulsion concentrates, directly sprayable or dilutable solutions, dilute emulsions, wettable powders, soluble powders, dusts, granules, and also encapsulations, for example in polymeric substances. The application methods, such as spraying, atomising, dusting, scattering or pouring, as well as the type of composition are selected to suit the intended aims and the prevailing circumstances.

The formulations, i.e., the compositions, preparations or combinations containing the active ingredient of the formula I and, if desired, a solid or liquid additive, are prepared in a known manner, for example by intimately mixing and/or grinding the active ingredients with extenders, for example with solvents, solid carriers and, if desired, surface-active compounds (surfactants).

The following are possible as solvents: aromatic hydrocarbons, preferably the fractions $C_8$–$C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and also epoxidised or unepoxidised vegetable oils, such as epoxidised coconut oil or soya oil, or water.

Solid carriers which are generally used, for example for dusts and dispersible powders, are ground natural minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types, for example pumice, brick grit, sepiolite or bentonite, or non-sorptive carrier materials, such as calcite or sand. Moreover, a large number of pregranulated materials or inorganic or organic nature can be used, such as, in particular, dolomite or comminuted plant residues.

Suitable surface-active compounds are non-ionic, cationic and/or anionic surfactants having good emulsifying, dispersing and wetting properties, depending on the nature of the active ingredient of the formula I to be formulated. Surfactants are also to be understood as meaning mixtures of surfactants.

Anionic surfactants which are suitable can be either so-called water-soluble soaps or water-soluble synthetic surface-active compounds.

Suitable soaps which may be mentioned are the alkali metal salts, alkaline earth metal salts or substituted or unsubstituted ammonium salts of higher fatty acids ($C_{10}$–$C_{22}$), such as the sodium salts or potassium salts of oleic or stearic acid, or of natural mixtures of fatty acids which can be obtained, for example, from coconut or tallow oil. Mention must also be made of the fatty acid methyltaurinates.

However, so-called synthetic surfactants are used more frequently, in particular fatty sulfonates, fatty sulfates, sulfonated benzimidazole derivatives or alkylarylsulfonates.

The fatty sulfates or fatty sulfonates are generally in the form of alkali metal salts, alkaline earth metal salts or substituted or unsubstituted ammonium salts, and generally have an alkyl radical having 8 to 22 C atoms, alkyl also including the alkyl moiety of acyl radicals, for example the sodium or calcium salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and one fatty acid radical having 8 to 22 C atoms. Examples of arylalkylsulfonates are the sodium, calcium or triethanolamine salts of dodecylbenzenesulfonic acid, of dibutylnaphthalenesulfonic acid or of a naphthalenesulfonic acid/formaldehyde condensation product.

Other suitable compounds are the corresponding phosphates, such as the salts of the phosphoric ester of a p-nonylphenol/(4–14)-ethylene oxide adduct or phospholipids.

Suitable non-ionic surfactants are mainly polyglycol ether derivatives of aliphatic or cycloaliphatic alcohols, saturated or unsaturated fatty acids and alkylphenols, which can contain 3 to 10 glycol ether groups and 8 to 20 carbon atoms in the (aliphatic) hydrocarbon radical and 6 to 18 carbon atoms in the alkyl radical of the alkylphenols.

Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which comprise 20 to 250 ethylene glycol ether groups and 10 to 100 propylene glycol ether groups. The abovementioned compounds customarily comprise 1 to 5 ethylene glycol units per propylene glycol unit.

Examples of non-ionic surfactants which may be mentioned are nonylphenolpolyethoxyethanols, castor oil polyethylene glycol ethers, polypropylene/polyethylene oxide adducts, tributylphenoxypolyethoxyethanol, polyethylene glycol and octylphenoxypolyethoxyethanol.

Other suitable substances are fatty acid esters of polyoxyethylenesorbitan, such as polyoxyethylenesorbitan trioleate.

The cationic surfactants are mainly quaternary ammonium salts which contain at least one alkyl radical having 8 to 22 C atoms as N-substituent and which have lower halogenated or free alkyl, benzyl or lower hydroxyalkyl radicals as further substituents. The salts are preferably in the form of halides, methylsulfates or ethylsulfates, for example stearyltrimethylammonium chloride or benzyldi(2-choroethyl)ethylammonium bromide.

The surfactants customary in the art of formulation are described, inter alia, in the following publications:

"McCutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" [Surfactants Guide]", Carl Hanser Veriag, Munich/Vienna 1981.

As a rule, the agrochemical preparations contain 0.1 to 95%, in particular 0.1 to 80%, of the active ingredient of the formula I, 1 to 99.9% of a solid or liquid additive and 0 to 25%, in particular 0.1 to 25%, of a surfactant.

In particular, preferred formulations have the following composition: (%=percent by weight)

| | |
|---|---|
| Emulsifiable concentrates: | |
| Active ingredient: | 1 to 20%, 5 to 10% being preferred |
| Surface-active agent: | 5 to 30%, preferably 10 to 20% |
| Liquid carrier: | 50 to 94%, preferably 70 to 85% |
| Dusts | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surface-active agent: | 1 to 40%, preferably 2 to 30% |
| Wettable powder: | |
| Active ingredient: | 0.5 to 90%, preferably 1 to 80% |
| Surface-active agent: | 0.5 to 20%, preferably 1 to 15% |
| Solid carrier: | 5 to 99%, preferably 15 to 90% |
| Granules: | |
| Active ingredient: | 0.5 to 30%, preferably 3 to 15% |

-continued

| | |
|---|---|
| Solid carrier: | 99.5 to 70%, preferably 97 to 85% |

While concentrated compositions are often preferred as commercially available goods, the end user will normally use dilute compositions. The use forms can be diluted down to 0.001% active ingredient. The rates of application are generally 0.001 to 5 kg of a.i./ha, preferably 0.005 to 3 kg of a.i./ha.

The compositions can also contain further additives, such as stabilisers, defoamers, viscosity regulators, binders, tackifiers and also fertilisers or other active ingredients for achieving specific effects.

The examples which follow illustrate the invention.

PREPARATION EXAMPLES

H.1.2-(2,4,6-trimethylphenylacetyl)-1-ethoxycarbonylhexahydropyridazine

To a solution of 11 g (70 mmol) of ethyl hexahydropyridazine-1-carboxylate and 10.8 ml (70 mmol) of triethylamine in 350 ml of diethyl ether there is added dropwise with stirring at 20°–25° C. a solution of 13.8 g (70 mmol) of mesityleneacetyl chloride in 100 ml of diethyl ether. The mixture is subsequently stirred for a further 3 hours at room temperature. Precipitated triethyleneamine hydrochloride is then filtered off with suction, and the filtrate is concentrated in vacuo and chromatographed with ethyl acetate/hexane (1:1) on silica gel.

20.1 g (90.5%) of the title compound of the formula

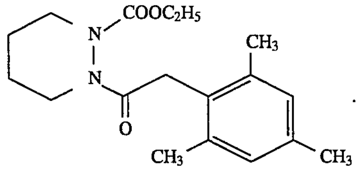

are isolated.

H.2.2-(2,4,6-trimethylphenyl)-5,6,7,8-tetrahydro-1H-pyrazolo[1,2-a]pyridazine-1,3(2H)-dione 3.69 g (88 mmol) of a 60% suspension of sodium hydride in white oil are introduced into 75 ml of toluene. To this mixture there are added dropwise at room temperate 22.3 g (70 mmol) of a solution of 2-(2,4,6-trimethylphenylacetyl)-1-ethoxycarbonylhexahydropyridazine in 75 ml of toluene, and the mixture is heated at the boil for 6 hours. 10 ml of ethanol are then added dropwise with ice-cooling, the reaction mixture is evaporated to dryness in vacuo, and the residue is dissolved in 200 ml of 1N NaOH. The product is precipitated from the resulting solution by adding concentrated hydrochloric acid at 0° C. The crude product is purified by recrystallisation from chloroform/hexane.

8.9g of the title compound (Compound No. 1.010) of the formula

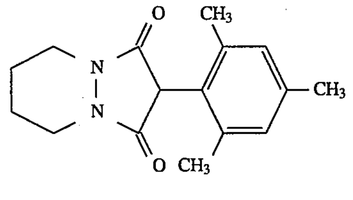

are isolated in the form of crystals of m.p. 244°–246° C.

The compounds of Tables 1 to 14 can be prepared analogously to the above examples and to the preparation processes described:

TABLE 1

Compounds of the formula

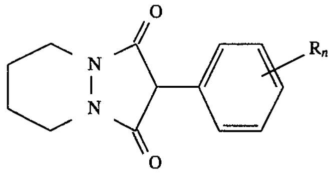

| Comp. Nr. | | $R_n$ | | Phys. data (°C.) |
|---|---|---|---|---|
| 1.001 | | H | | m.p. 184–185 |
| 1.002 | | 2-$CH_3$ | | m.p. 172,5–173,5 |
| 1.003 | | 4-$CH_3$ | | m.p. 186–187 |
| 1.004 | | 2-$CH_3$ | 4-$CH_3$ | m.p. 247–248 |
| 1.005 | | 2-$CH_3$ | 6-$CH_3$ | m.p. 209–210 |
| 1.006 | | 2-$CH_3$ | 5-$CH_3$ | m.p. 136–137 |
| 1.007 | | 3-$CH_3$ | 5-$CH_3$ | |
| 1.008 | | 2-$CH_3$ | 3-$CH_3$ | |
| 1.009 | | 3-$CH_3$ | 4-$CH_3$ | |
| 1.010 | 2-$CH_3$ | 4-$CH_3$ | 6-$CH_3$ | m.p. 244–246 |
| 1.011 | 2-$CH_3$ | 4-$CH_3$ | 5-$CH_3$ | |
| 1.012 | | 2-Cl | | m.p. 178–178,5 |
| 1.013 | | 4-Cl | | m.p. 206–207 |
| 1.014 | | 2-Cl | 4-Cl | m.p. 203–204 |
| 1.015 | | 2-Cl | 6-Cl | m.p. >250 |
| 1.016 | | 2-Cl | 6-F | m.p. 218–219 |
| 1.017 | | 2-$CH_3$ | 4-Cl | |
| 1.018 | | 2-$CH_3$ | 4-F | |
| 1.019 | | 2-Cl | 4-$CH_3$ | |
| 1.020 | | 2-Cl | 6-$CH_3$ | |
| 1.021 | | 2-F | 4-F | |
| 1.022 | | 2-F | 6-F | m.p. 228–229 |
| 1.023 | | 2-$CH_3$ | 4-O–$CH_3$ | |
| 1.024 | | 2-$CH_3$ | 6-O–$CH_3$ | |
| 1.025 | | 2-Cl | 4-O–$CH_3$ | |
| 1.026 | | 2-Cl | 6-O–$CH_3$ | |
| 1.027 | | 3-$OCH_3$ | 4-$OCH_3$ | |
| 1.028 | | 2-$OCH_3$ | 5-$OCH_3$ | |
| 1.029 | | 2-$OCH_3$ | 4-$OCH_3$ | |
| 1.030 | | 2-$OCH_3$ | 6-$OCH_3$ | |
| 1.031 | | 2-$CF_3$ | 6-$CF_3$ | |
| 1.032 | | 2-$CF_3$ | 4-$CF_3$ | |
| 1.033 | | 3-$CF_3$ | 5-$CF_3$ | |
| 1.034 | | 2-Cl | 4-$CF_3$ | m.p. 195–197 |
| 1.035 | | 2-Cl | 6-$CF_3$ | |
| 1.036 | | 2-$NO_2$ | 4-$NO_2$ | |
| 1.037 | | 2-Cl | 4-$NO_2$ | |
| 1.038 | | 2-$CH_3$ | 4-$NO_2$ | |
| 1.039 | | 2-O–$CH_3$ | 4-$NO_2$ | |
| 1.040 | | 2-F | 6-$NO_2$ | |
| 1.041 | | 2-Cl | 6-$NO_2$ | |
| 1.042 | | 2-$CH_3$ | 6-$NO_2$ | |
| 1.043 | | 2-O–$CH_3$ | 6-$NO_2$ | |
| 1.044 | | 2-F | 4-$NO_2$ | |
| 1.045 | | 2-$CH_3$ | 4-N($C_2H_5$)2 | |
| 1.046 | | 2-Cl | 4-$SO_2$–$CH_3$ | |
| 1.047 | | 2-Cl | 4-SO–$CH_3$ | |
| 1.048 | | 2-Cl | 4-S–$CH_3$ | |
| 1.049 | | 2-Cl | 6-$SO_2$–$CH_3$ | |
| 1.050 | | 2-Cl | 6-SO–$CH_3$ | |
| 1.051 | | 2-Cl | 6-S–$CH_3$ | |
| 1.052 | | 2-$CH_3$ | 4-$SO_2$–$CH_3$ | |
| 1.053 | | 2-$CH_3$ | 4-SO–$CH_3$ | |
| 1.054 | | 2-$CH_3$ | 4-S–$CH_3$ | |
| 1.055 | | 2-$CH_3$ | 6-$SO_2$–$CH_3$ | |
| 1.056 | | 2-$CH_3$ | 6-SO–$CH_3$ | |
| 1.057 | | 2-$CH_3$ | 6-S–$CH_3$ | |
| 1.058 | | 2-O–$CH_3$ | 6-$SO_2$–$CH_3$ | |
| 1.059 | | 2-O–$CH_3$ | 6-SO–$CH_3$ | |
| 1.060 | | 2-O–$CH_3$ | 6-S–$CH_3$ | |
| 1.061 | | 2-O–$CH_3$ | 4-$SO_2$–$CH_3$ | |

TABLE 1-continued

Compounds of the formula

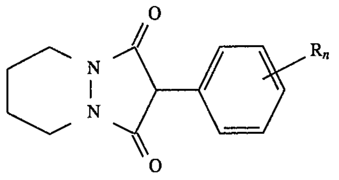

| Comp. Nr. | | $R_n$ | | Phys. data (°C.) |
|---|---|---|---|---|
| 1.062 | | $2-O-CH_3$ | $4-SO-CH_3$ | |
| 1.063 | | $2-O-CH_3$ | $4-S-CH_3$ | |
| 1.064 | | $2-CH_3$ | $6-N(C_2H_5)2$ | |
| 1.065 | | 2-Cl | $6-N(CH_3)_2$ | |
| 1.066 | | 2-Cl | $4-N(CH_3)_2$ | |
| 1.067 | | 2-Cl | $4-CO_2CH_3$ | |
| 1.068 | | $2-CH_3$ | $6-CO_2C_2H_5$ | |
| 1.069 | | $2-CH_3$ | $4-CO_2C_2H_5$ | |
| 1.070 | | $2-CH_3$ | 4-CN | |
| 1.071 | | $2-CH_3$ | 6-CN | |
| 1.072 | | 2-Cl | 4-CN | |
| 1.073 | | 2-Cl | 6-CN | |
| 1.074 | | 2-Cl | $4-CO-CH_3$ | |
| 1.075 | | $2-O-CHF_2$ | $4-O-CHF_2$ | |
| 1.076 | | $2-CH_3$ | $4-O-CHF_2$ | |
| 1.077 | | 2-Cl | $4-O-CF_3$ | |
| 1.078 | | $2-O-CF_3$ | $4-O-CH_3$ | |
| 1.079 | | $2-O-CHF_2$ | 4-Cl | |
| 1.080 | | $2-O-CHF_2$ | $6-CH_3$ | |
| 1.081 | | $2-O-CHF_2$ | 6-Cl | |
| 1.082 | $2-O-CHF_2$ | $4-CH_3$ | $6-CH_3$ | |
| 1.083 | $2-CH_3$ | $4-t-C_4H_9$ | $6-CH_3$ | |
| 1.084 | $2-i-C_3H_7$ | $4-i-C_3H_7$ | $6-i-C_3H_7$ | |
| 1.085 | $2-CH_3$ | $4-O-CH_3$ | $6-CH_3$ | |
| 1.086 | 2-Cl | $4-CF_3$ | 6-Cl | m.p. >260 |
| 1.087 | 2-Cl | $4-CF_3$ | 6-F | |
| 1.088 | 2-Cl | $4-NO_2$ | 6-Cl | |
| 1.089 | 2-Cl | 4-Cl | 6-Cl | |
| 1.090 | 2-F | 4-F | 6-F | |
| 1.091 | $2-CH_3$ | $4-NO_2$ | $6-CH_3$ | |
| 1.092 | 2-Cl | 4-Cl | $6-CH_3$ | |
| 1.093 | 2-Cl | $4-O-CH_3$ | 6-Cl | |
| 1.094 | 2-Cl | 4-Cl | $6-O-CH_3$ | |
| 1.095 | 2-F | $4-O-CH_3$ | 6-F | |
| 1.096 | $2-O-CH_3$ | $4-CH_3$ | $6-O-CH_3$ | |
| 1.097 | $2-O-CH_3$ | $4-O-CH_3$ | $6-CH_3$ | |
| 1.098 | $2-O-CH_3$ | $4-O-CH_3$ | $6-O-CH_3$ | |
| 1.099 | $2-O-CH_3$ | $4-CO-O-CH_3$ | $6-O-CH_3$ | |
| 1.100 | $2-CH_3$ | 4-Cl | $6-CH_3$ | |
| 1.101 | $2-CH_3$ | 4-F | $6-CH_3$ | |
| 1.102 | $2-CH_3$ | $4-CH_3$ | $6-O-CH_3$ | |
| 1.103 | 2-F | 4-Cl | $5-O-i-C_3H_7$ | m.p. 180–181 |
| 1.104 | 2-Cl | 4-Cl | $5-O-CH_3$ | |
| 1.105 | | 4-Cl | $5-O-CH_3$ | |
| 1.106 | 2-F | 4-Cl | $5-CO-O-CH_3$ | |
| 1.107 | 2-F | 4-Cl | $5-CO-O-C_2H_5$ | |
| 1.108 | | 4-Cl | $5-CO-O-CH_3$ | |
| 1.109 | 2-Cl | 4-Cl | $5-CO-O-i-C_3H_7$ | |
| 1.110 | | 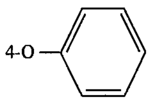 | | |
| 1.111 | | 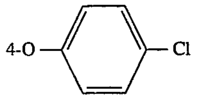 | | |
| 1.112 | | 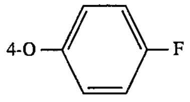 | | |

TABLE 1-continued
Compounds of the formula
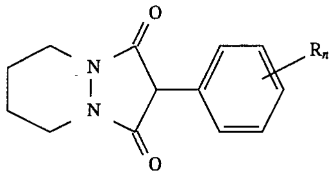
| Comp. Nr. | | $R_n$ | | Phys. data (°C.) |
|---|---|---|---|---|
| 1.113 | | 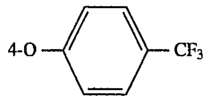 | | m.p. 178–179 |
| 1.114 | 2-$CH_3$ | 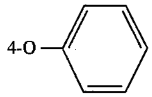 | | |
| 1.115 | | 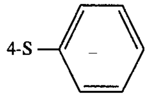 | | |
| 1.116 | | 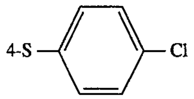 | | m.p. 242–243 |
| 1.117 | | 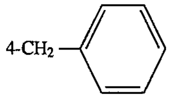 | | |
| 1.118 | | 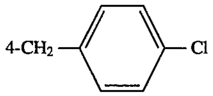 | | |
| 1.119 | | 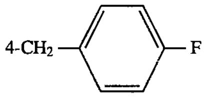 | | |
| 1.120 | | 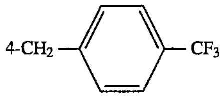 | | |
| 1.121 | | 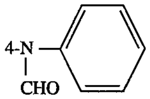 | | |
| 1.122 | 2-F | 4-Cl | 5-O$-CH_2-CH-CH_2$ | |
| 1.123 | 2-F | 4-Cl | 5-O$-CH_2-C\equiv CH$ | |
| 1.124 | 2-Br | | | m.p. 180–182 |
| 1.125 | 2-$CF_3$ | | | m.p. 185–186 |
| 1.126 | 2-$OCH_3$ | | | m.p. 191–194 |
| 1.127 | 2-$CH_3$ | 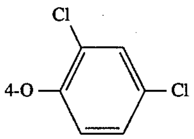 | | |

TABLE 1-continued
Compounds of the formula
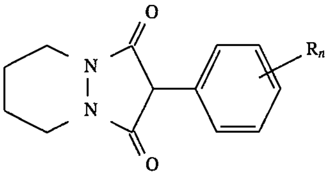
| Comp. Nr. | $R_n$ | | | Phys. data (°C.) |
|---|---|---|---|---|
| 1.128 | 2-$CH_3$ | 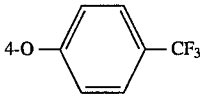 | | |
| 1.129 | 2-$CH_3$ | 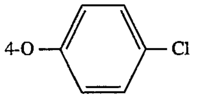 | | |
| 1.130 | 2-$CH_3$ | 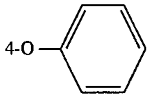 | 6-$CH_3$ | |
| 1.131 | 2-$CH_3$ | 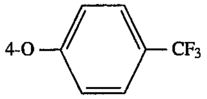 | 6-$CH_3$ | |
| 1.132 | 2-$CH_3$ | 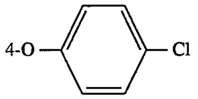 | 6-$CH_3$ | |
| 1.133 | 2-$CH_3$ | 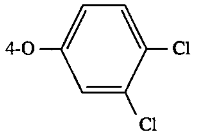 | 6-$CH_3$ | |
| 1.134 | 2-$CH_3$ | 4-Br | 6-$CH_3$ | |
| 1.135 | 2-$CH_3$ | 6-$C_2H_5$ | | |
| 1.136 | 2-$C_2H_5$ | 6-$C_2H_5$ | | |
| 1.137 | 2-$CH_3$ | 4-$OC_2H_5$ | 6-$CH_3$ | |
| 1.138 | 2-$CH_3$ | 4-O-i-$C_3H_7$ | 6-$CH_3$ | |
| 1.139 | 2-$CH_3$ | 4-O-n-$C_3H_7$ | 6-$CH_3$ | |
| 1.140 | 2-$CH_3$ | 4-O-n-$C_{10}H_{21}$ | 6-$CH_3$ | |
| 1.141 | 2-$CH_3$ | 4-O-n-$C_3H_7$ | | |
| 1.142 | 2-$CH_3$ | 4-O—$(CH_2)_2OCH_3$ | | |
| 1.143 | 2-$CH_3$ | 4-O—$(CH_2)_2OCH_3$ | 6-$CH_3$ | |
| 1.144 | 2-$CH_3$ | 4-O—$(CH_2)_2OCH_3$ | | |
| 1.145 | 2-$CH_3$ | 4-O-n-$C_6H_{13}$ | 6-$CH_3$ | |
| 1.146 | 2-$CH_3$ | 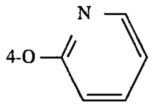 | | |
| 1.147 | 2-$CH_3$ | 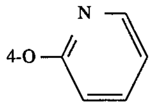 | 6-$CH_3$ | |
| 1.148 | 2-$CH_3$ | 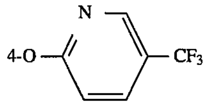 | | |

TABLE 1-continued
Compounds of the formula
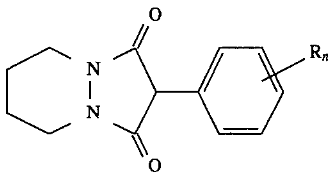
| Comp. Nr. | $R_n$ | | | Phys. data (°C.) |
|---|---|---|---|---|
| 1.149 | 2-$CH_3$ | 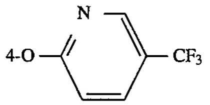 | 6-$CH_3$ | |
| 1.150 | 2-$CH_3$ | 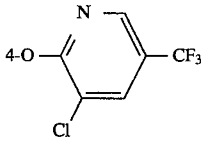 | | |
| 1.151 | 2-$CH_3$ | 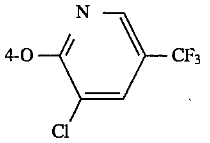 | 6-$CH_3$ | |
| 1.152 | 2-$CH_3$ | 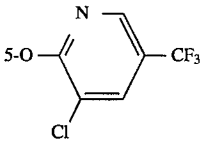 | | |
| 1.153 | 2-$CH_3$ | 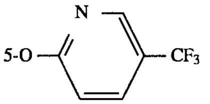 | | |
| 1.154 | 2-$CH_3$ | 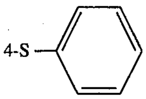 | 6-$CH_3$ | |
| 1.155 | 2-$CH_3$ | 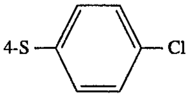 | 6-$CH_3$ | |
| 1.156 | 2-$C_2H_5$ | 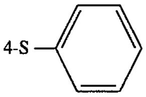 | 6-$CH_3$ | |

TABLE 2

Compounds of the formula

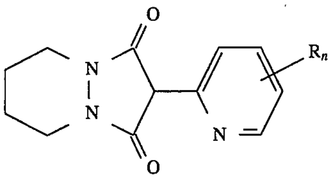

| Com.p. No. | $R_n$ | | Phys. data (°C.) |
|---|---|---|---|
| 2.001 | 3-Cl | | |
| 2.002 | 3-F | | |
| 2.003 | 3-$CH_3$ | | |
| 2.004 | 5-Cl | | |
| 2.005 | 5-$CF_3$ | | |
| 2.006 | 3-Cl | 5-Cl | |
| 2.007 | 3-Cl | 5-F | |
| 2.008 | 3-Cl | 5-$CF_3$ | m.p. 172–174 |
| 2.009 | 3-Cl | 5-$NO_2$ | |
| 2.010 | 3-Cl | 5-$SO_2-CH_3$ | |

TABLE 2-continued

Compounds of the formula

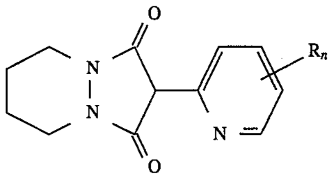

| Com.p. No. | $R_n$ | | Phys. data (°C.) |
|---|---|---|---|
| 2.011 | 3-F | 5-F | |
| 2.012 | 3-F | 5-Cl | |
| 2.013 | 3-F | 5-$CF_3$ | |
| 2.014 | 3-$NO_2$ | 5-$NO_2$ | |
| 2.015 | 3-$NO_2$ | 5-Cl | |
| 2.016 | 3-$NO_2$ | 5-$CF_3$ | |
| 2.017 | 3-$CF_3$ | 5-Cl | |
| 2.018 | 3-$CF_3$ | 5-$CF_3$ | |
| 2.019 | 3-$CH_3$ | 5-$CH_3$ | |

TABLE 3

Compounds of the formula

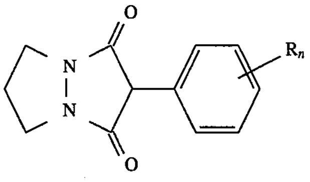

| Comp. No. | | $R_n$ | | Phys. data (°C.) |
|---|---|---|---|---|
| 3.001 | | H | | |
| 3.002 | | 2-$CH_3$ | | |
| 3.003 | | 4-$CH_3$ | | |
| 3.004 | | 2-$CH_3$ | 4-$CH_3$ | |
| 3.005 | | 2-$CH_3$ | 6-$CH_3$ | |
| 3.006 | | 2-$CH_3$ | 5-$CH_3$ | |
| 3.007 | | 3-$CH_3$ | 5-$CH_3$ | |
| 3.008 | | 2-$CH_3$ | 3-$CH_3$ | |
| 3.009 | | 3-$CH_3$ | 4-$CH_3$ | |
| 3.010 | 2-$CH_3$ | 4-$CH_3$ | 6-$CH_3$ | m.p. 191–193 |
| 3.011 | 2-$CH_3$ | 4-$CH_3$ | 5-$CH_3$ | |
| 3.012 | | 2-Cl | | |
| 3.013 | | 4-Cl | | |
| 3.014 | | 2-Cl | 4-Cl | |
| 3.015 | | 2-Cl | 6-Cl | m.p. 213–215 |
| 3.016 | | 2-Cl | 6-F | |
| 3.017 | | 2-$CH_3$ | 4-Cl | |
| 3.018 | | 2-$CH_3$ | 4-F | |
| 3.019 | | 2-Cl | 4-$CH_3$ | |
| 3.020 | | 2-Cl | 6-$CH_3$ | |
| 3.021 | | 2-F | 4-F | |
| 3.022 | | 2-F | 6-F | |
| 3.023 | | 2-$CH_3$ | 4-O$-CH_3$ | |
| 3.024 | | 2-$CH_3$ | 6-O$-CH_3$ | |
| 3.025 | | 2-Cl | 4-O$-CH_3$ | |
| 3.026 | | 2-Cl | 6-O$-CH_3$ | |
| 3.027 | | 3-$OCH_3$ | 4-$OCH_3$ | |
| 3.028 | | 2-$OCH_3$ | 5-$OCH_3$ | |
| 3.029 | | 2-$OCH_3$ | 4-$OCH_3$ | |
| 3.030 | | 2-$OCH_3$ | 6-$OCH_3$ | |
| 3.031 | | 2-$CF_3$ | 6-$CF_3$ | |
| 3.032 | | 2-$CF_3$ | 4-$CF_3$ | |
| 3.033 | | 3-$CF_3$ | 5-$CF_3$ | |
| 3.034 | | 2-Cl | 4-$CF_3$ | |
| 3.035 | | 2-Cl | 6-$CF_3$ | |
| 3.036 | | 2-$NO_2$ | 4-$NO_2$ | |

TABLE 3-continued

Compounds of the formula

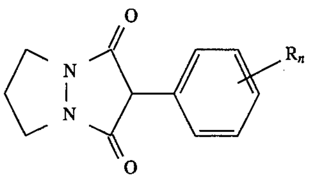

| Comp. No. | $R_n$ | | | Phys. data (°C.) |
|---|---|---|---|---|
| 3.037 | | 2-Cl | $4\text{-}NO_2$ | |
| 3.038 | | $2\text{-}CH_3$ | $4\text{-}NO_2$ | |
| 3.039 | | $2\text{-}O-CH_3$ | $4\text{-}NO_2$ | |
| 3.040 | | 2-F | $6\text{-}NO_2$ | |
| 3.041 | | 2-Cl | $6\text{-}NO_2$ | |
| 3.042 | | $2\text{-}CH_3$ | $6\text{-}NO_2$ | |
| 3.043 | | $2\text{-}O-CH_3$ | $6\text{-}NO_2$ | |
| 3.044 | | 2-F | $4\text{-}NO_2$ | |
| 3.045 | | $2\text{-}CH_3$ | $4\text{-}N(C_2H_5)_2$ | |
| 3.046 | | 2-Cl | $4\text{-}SO_2-CH_3$ | |
| 3.047 | | 2-Cl | $4\text{-}SO-CH_3$ | |
| 3.048 | | 2-Cl | $4\text{-}S\text{-}CH_3$ | |
| 3.049 | | 2-Cl | $6\text{-}SO_2-CH_3$ | |
| 3.050 | | 2-Cl | $6\text{-}SO-CH_3$ | |
| 3.051 | | 2-Cl | $6\text{-}S-CH_3$ | |
| 3.052 | | $2\text{-}CH_3$ | $4\text{-}SO_2-CH_3$ | |
| 3.053 | | $2\text{-}CH_3$ | $4\text{-}SO-CH_3$ | |
| 3.054 | | $2\text{-}CH_3$ | $4\text{-}S-CH_3$ | |
| 3.055 | | $2\text{-}CH_3$ | $6\text{-}SO_2-CH_3$ | |
| 3.056 | | $2\text{-}CH_3$ | $6\text{-}SO-CH_3$ | |
| 3.057 | | $2\text{-}CH_3$ | $6\text{-}S-CH_3$ | |
| 3.058 | | $2\text{-}O-CH_3$ | $6\text{-}SO_2-CH_3$ | |
| 3.059 | | $2\text{-}O-CH_3$ | $6\text{-}SO-CH_3$ | |
| 3.060 | | $2\text{-}O-CH_3$ | $6\text{-}S-CH_3$ | |
| 3.061 | | $2\text{-}O-CH_3$ | $4\text{-}SO_2-CH_3$ | |
| 3.062 | | $2\text{-}O-CH_3$ | $4\text{-}SO-CH_3$ | |
| 3.063 | | $2\text{-}O-CH_3$ | $4\text{-}S-CH_3$ | |
| 3.064 | | $2\text{-}CH_3$ | $6\text{-}N(C_2H_5)_2$ | |
| 3.065 | | 2-Cl | $6\text{-}N(CH_3)_2$ | |
| 3.066 | | 2-Cl | $4\text{-}N(CH_3)_2$ | |
| 3.067 | | 2-Cl | $4\text{-}CO_2CH_3$ | |
| 3.068 | | $2\text{-}CH_3$ | $6\text{-}CO_2C_2H_5$ | |
| 3.069 | | $2\text{-}CH_3$ | $4\text{-}CO_2C_2H_5$ | |
| 3.070 | | $2\text{-}CH_3$ | 4-CN | |
| 3.071 | | $2\text{-}CH_3$ | 6-CN | |
| 3.072 | | 2-Cl | 4-CN | |
| 3.073 | | 2-Cl | 6-CN | |
| 3.074 | | 2-Cl | $4\text{-}CO-CH_3$ | |
| 3.075 | | $2\text{-}O-CHF_2$ | $4\text{-}O-CHF_2$ | |
| 3.076 | | $2\text{-}CH_3$ | $4\text{-}O-CHF_2$ | |
| 3.077 | | 2-Cl | $4\text{-}O-CF_3$ | |
| 3.078 | | $2\text{-}O-CF_3$ | $4\text{-}O-CH_3$ | |
| 3.079 | | $2\text{-}O-CHF_2$ | 4-Cl | |
| 3.080 | | $2\text{-}O-CHF_2$ | $6\text{-}CH_3$ | |
| 3.081 | | $2\text{-}O-CHF_2$ | 6-Cl | |
| 3.082 | $2\text{-}O-CHF_2$ | $4\text{-}CH_3$ | $6\text{-}CH_3$ | |
| 3.083 | $2\text{-}CH_3$ | $4\text{-}t\text{-}C_4H_9$ | $6\text{-}CH_3$ | |
| 3.084 | $2\text{-}i\text{-}C_3H_7$ | $4\text{-}i\text{-}C_3H_7$ | $6\text{-}i\text{-}C_3H_7$ | |
| 3.085 | $2\text{-}CH_3$ | $4\text{-}O-CH_3$ | $6\text{-}CH_3$ | |
| 3.086 | 2-Cl | $4\text{-}CF_3$ | 6-Cl | |
| 3.087 | 2-Cl | $4\text{-}CF_3$ | 6-F | |
| 3.088 | 2-Cl | $4\text{-}NO_2$ | 6-Cl | |
| 3.089 | 2-Cl | 4-Cl | 6-Cl | |
| 3.090 | 2-F | 4-F | 6-F | |
| 3.091 | $2\text{-}CH_3$ | $4\text{-}NO_2$ | $6\text{-}CH_3$ | |
| 3.092 | 2-Cl | 4-Cl | $6\text{-}CH_3$ | |
| 3.093 | 2-Cl | $4\text{-}O-CH_3$ | 6-Cl | |
| 3.094 | 2-Cl | 4-Cl | $6\text{-}O-CH_3$ | |
| 3.095 | 2-F | $4\text{-}O-CH_3$ | 6-F | |
| 3.096 | $2\text{-}O-CH_3$ | $4\text{-}CH_3$ | $6\text{-}O-CH_3$ | |
| 3.097 | $2\text{-}O-CH_3$ | $4\text{-}O-CH_3$ | $6\text{-}CH_3$ | |
| 3.098 | $2\text{-}O-CH_3$ | $4\text{-}O-CH_3$ | $6\text{-}O-CH_3$ | |
| 3.099 | $2\text{-}O-CH_3$ | $4\text{-}CO\text{-}O-CH_3$ | $6\text{-}O-CH_3$ | |
| 3.100 | $2\text{-}CH_3$ | 4-Cl | $6\text{-}CH_3$ | |
| 3.101 | $2\text{-}CH_3$ | 4-F | $6\text{-}CH_3$ | |

TABLE 3-continued
Compounds of the formula
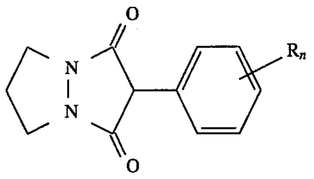
| Comp. No. | | $R_n$ | | Phys. data (°C.) |
|---|---|---|---|---|
| 3.102 | 2-$CH_3$ | 4-$CH_3$ | 6-O—$CH_3$ | |
| 3.103 | 2-F | 4-Cl | 5-O-i-$C_3H_7$ | |
| 3.104 | 2-Cl | 4-Cl | 5-O—$CH_3$ | |
| 3.105 | | 4-Cl | 5-O—$CH_3$ | |
| 3.106 | 2-F | 4-Cl | 5-CO—O—$CH_3$ | |
| 3.107 | 2-F | 4-Cl | 5-CO—O—$C_2H_5$ | |
| 3.108 | | 4-Cl | 5-CO—O—$CH_3$ | |
| 3.109 | 2-Cl | 4-Cl | 5-CO—O-i-$C_3H_7$ | |
| 3.110 | | 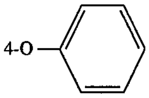 | | |
| 3.111 | | 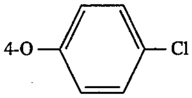 | | |
| 3.112 | | 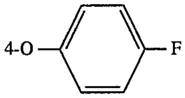 | | |
| 3.113 | | 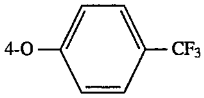 | | |
| 3.114 | 2-$CH_3$ | 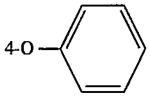 | | |
| 3.115 | | 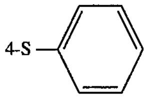 | | |
| 3.116 | | 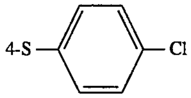 | | |
| 3.117 | | 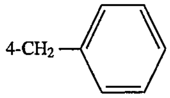 | | |
| 3.118 | | 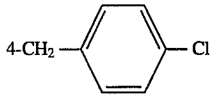 | | |
| 3.119 | | 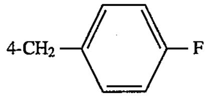 | | |

TABLE 3-continued

Compounds of the formula

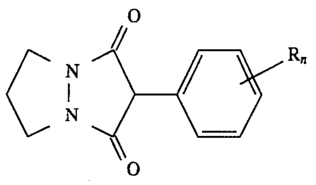

| Comp. No. | $R_n$ | | | Phys. data (°C.) |
|---|---|---|---|---|
| 3.120 | | 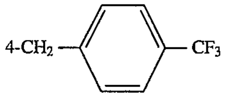 | | |
| 3.121 | | 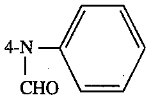 | | |
| 3.122 | 2-F | 4-Cl | $5\text{-}O-CH_2-CH=CH_2$ | |
| 3.123 | 2-F | 4-Cl | $5\text{-}O-CH_2-C\equiv CH$ | |
| 3.124 | 2-Br | | | |
| 3.125 | $2\text{-}CF_3$ | | | |
| 3.126 | $2\text{-}OCH_3$ | | | |
| 3.127 | $2\text{-}CH_3$ | 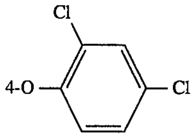 | | |
| 3.128 | $2\text{-}CH_3$ | 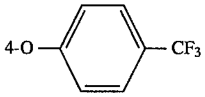 | | |
| 3.129 | $2\text{-}CH_3$ | 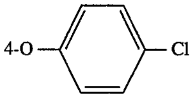 | | |
| 3.130 | $2\text{-}CH_3$ | 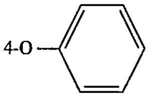 | $6\text{-}CH_3$ | |
| 3.131 | $2\text{-}CH_3$ | 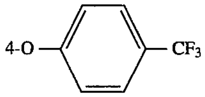 | $6\text{-}CH_3$ | |
| 3.132 | $2\text{-}CH_3$ | 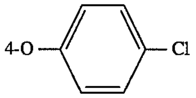 | $6\text{-}CH_3$ | |
| 3.133 | $2\text{-}CH_3$ | 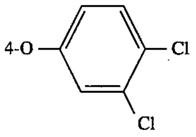 | $6\text{-}CH_3$ | |
| 3.134 | $2\text{-}CH_3$ | 4-Br | $6\text{-}CH_3$ | |
| 3.135 | $2\text{-}CH_3$ | $6\text{-}C_2H_5$ | | |
| 3.136 | $2\text{-}C_2H_5$ | $6\text{-}C_2H_5$ | | |
| 3.137 | $2\text{-}CH_3$ | $4\text{-}OC_2H_5$ | $6\text{-}CH_3$ | |
| 3.138 | $2\text{-}CH_3$ | $4\text{-}O\text{-}i\text{-}C_3H_7$ | $6\text{-}CH_3$ | |

TABLE 3-continued
Compounds of the formula
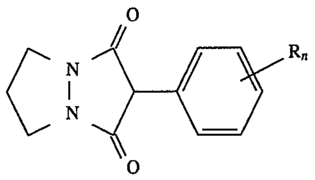
| Comp. No. | | $R_n$ | | Phys. data (°C.) |
|---|---|---|---|---|
| 3.139 | 2-$CH_3$ | 4-O-n-$C_3H_7$ | 6-$CH_3$ | |
| 3.140 | 2-$CH_3$ | 4-O-n-$C_{10}H_{21}$ | 6-$CH_3$ | |
| 3.141 | 2-$CH_3$ | 4-O-n-$C_3H_7$ | | |
| 3.142 | 2-$CH_3$ | 4-O$-(CH_2)_2OCH_3$ | | |
| 3.143 | 2-$CH_3$ | 4-O$-(CH_2)_2OCH_3$ | 6-$CH_3$ | |
| 3.144 | 2-$CH_3$ | 4-O$-(CH_2)_2OCH_3$ | | |
| 3.145 | 2-$CH_3$ | 4-O-n-$C_6H_3$ | 6-$CH_3$ | |
| 3.146 | 2-$CH_3$ | 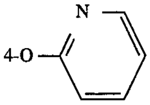 | | |
| 3.147 | 2-$CH_3$ | 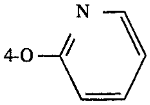 | 6-$CH_3$ | |
| 3.148 | 2-$CH_3$ | 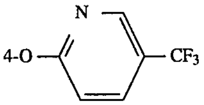 | | |
| 3.149 | 2-$CH_3$ | 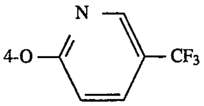 | 6-$CH_3$ | |
| 3.150 | 2-$CH_3$ | 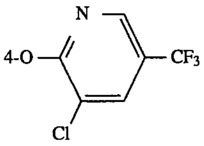 | | |
| 3.151 | 2-$CH_3$ | 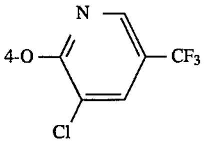 | 6-$CH_3$ | |
| 3.152 | 2-$CH_3$ | 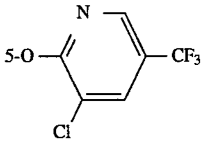 | | |
| 3.153 | 2-$CH_3$ | 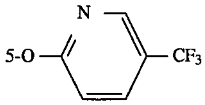 | | |
| 3.154 | 2-$CH_3$ | 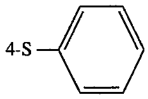 | 6-$CH_3$ | |

TABLE 3-continued

Compounds of the formula

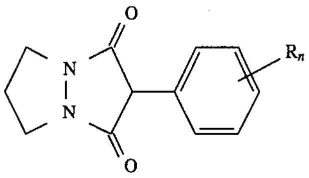

| Comp. No. | | $R_n$ | | Phys. data (°C.) |
|---|---|---|---|---|
| 3.155 | 2-$CH_3$ | 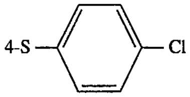 | 6-$CH_3$ | |
| 3.156 | 2-$C_2H_5$ | 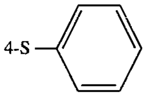 | 6-$CH_3$ | |

TABLE 4

Compounds of the formula

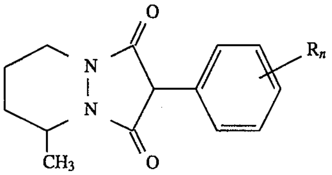

| Comp. No. | | $R_n$ | | Phys. data (°C.) |
|---|---|---|---|---|
| 4.001 | | H | | |
| 4.002 | | 2-$CH_3$ | | |
| 4.003 | | 4-$CH_3$ | | |
| 4.004 | | 2-$CH_3$ | 4-$CH_3$ | |
| 4.005 | | 2-$CH_3$ | 6-$CH_3$ | |
| 4.006 | | 2-$CH_3$ | 5-$CH_3$ | |
| 4.007 | | 3-$CH_3$ | 5-$CH_3$ | |
| 4.008 | | 2-$CH_3$ | 3-$CH_3$ | |
| 4.009 | | 3-$CH_3$ | 4-$CH_3$ | |
| 4.010 | 2-$CH_3$ | 4-$CH_3$ | 6-$CH_3$ | m.p. 206–207 |
| 4.011 | 2-$CH_3$ | 4-$CH_3$ | 5-$CH_3$ | |
| 4.012 | | 2-Cl | | |
| 4.013 | | 4-Cl | | |
| 4.014 | | 2-Cl | 4-Cl | |
| 4.015 | | 2-Cl | 6-Cl | |
| 4.016 | | 2-Cl | 6-F | |
| 4.017 | | 2-$CH_3$ | 4-Cl | |
| 4.018 | | 2-$CH_3$ | 4-F | |
| 4.019 | | 2-Cl | 4-$CH_3$ | |
| 4.020 | | 2-Cl | 6-$CH_3$ | |
| 4.021 | | 2-F | 4-F | |
| 4.022 | | 2-F | 6-F | |
| 4.023 | | 2-$CH_3$ | 4-O—$CH_3$ | |
| 4.024 | | 2-$CH_3$ | 6-O—$CH_3$ | |
| 4.025 | | 2-Cl | 4-O—$CH_3$ | |
| 4.026 | | 2-Cl | 6-O—$CH_3$ | |
| 4.027 | | 3-$OCH_3$ | 4-$OCH_3$ | |
| 4.028 | | 2-$OCH_3$ | 5-$OCH_3$ | |
| 4.029 | | 2-$OCH_3$ | 4-$OCH_3$ | |
| 4.030 | | 2-$OCH_3$ | 6-$OCH_3$ | |
| 4.031 | | 2-$CF_3$ | 6-$CF_3$ | |
| 4.032 | | 2-$CF_3$ | 4-$CF_3$ | |
| 4.033 | | 3-$CF_3$ | 5-$CF_3$ | |
| 4.034 | | 2-Cl | 4-$CF_3$ | |
| 4.035 | | 2-Cl | 6-$CF_3$ | |
| 4.036 | | 2-$NO_2$ | 4-$NO_2$ | |
| 4.037 | | 2-Cl | 4-$NO_2$ | |

TABLE 4-continued

Compounds of the formula

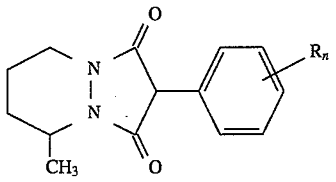

| Comp. No. | $R_n$ | | | Phys. data (°C.) |
|---|---|---|---|---|
| 4.038 | | 2-$CH_3$ | 4-$NO_2$ | |
| 4.039 | | 2-O$-$$CH_3$ | 4-$NO_2$ | |
| 4.040 | | 2-F | 6-$NO_2$ | |
| 4.041 | | 2-Cl | 6-$NO_2$ | |
| 4.042 | | 2-$CH_3$ | 6-$NO_2$ | |
| 4.043 | | 2-O$-$$CH_3$ | 6-$NO_2$ | |
| 4.044 | | 2-F | 4-$NO_2$ | |
| 4.045 | | 2-$CH_3$ | 4-$N(C_2H_5)_2$ | |
| 4.046 | | 2-Cl | 4-$SO_2$$-$$CH_3$ | |
| 4.047 | | 2-Cl | 4-SO$-$$CH_3$ | |
| 4.048 | | 2-Cl | 4-S$-$$CH_3$ | |
| 4.049 | | 2-Cl | 6-$SO_2$$-$$CH_3$ | |
| 4.050 | | 2-Cl | 6-SO$-$$CH_3$ | |
| 4.051 | | 2-Cl | 6-S$-$$CH_3$ | |
| 4.052 | | 2-$CH_3$ | 4-$SO_2$$-$$CH_3$ | |
| 4.053 | | 2-$CH_3$ | 4-SO$-$$CH_3$ | |
| 4.054 | | 2-$CH_3$ | 4-S$-$$CH_3$ | |
| 4.055 | | 2-$CH_3$ | 6-$SO_2$$-$$CH_3$ | |
| 4.056 | | 2-$CH_3$ | 6-SO$-$$CH_3$ | |
| 4.057 | | 2-$CH_3$ | 6-S$-$$CH_3$ | |
| 4.058 | | 2-O$-$$CH_3$ | 6-$SO_2$$-$$CH_3$ | |
| 4.059 | | 2-O$-$$CH_3$ | 6-SO$-$$CH_3$ | |
| 4.060 | | 2-O$-$$CH_3$ | 6-S$-$$CH_3$ | |
| 4.061 | | 2-O$-$$CH_3$ | 4-$SO_2$$-$$CH_3$ | |
| 4.062 | | 2-O$-$$CH_3$ | 4-SO$-$$CH_3$ | |
| 4.063 | | 2-O$-$$CH_3$ | 4-S$-$$CH_3$ | |
| 4.064 | | 2-$CH_3$ | 6-$N(C_2H_5)_2$ | |
| 4.065 | | 2-Cl | 6-$N(CH_3)_2$ | |
| 4.066 | | 2-Cl | 4-$N(CH_3)_2$ | |
| 4.067 | | 2-Cl | 4-$CO_2CH_3$ | |
| 4.068 | | 2-$CH_3$ | 6-$CO_2C_2H_5$ | |
| 4.069 | | 2-$CH_3$ | 4-$CO_2C_2H_5$ | |
| 4.070 | | 2-$CH_3$ | 4-CN | |
| 4.071 | | 2-$CH_3$ | 6-CN | |
| 4.072 | | 2-Cl | 4-CN | |
| 4.073 | | 2-Cl | 6-CN | |
| 4.074 | | 2-Cl | 4-CO$-$$CH_3$ | |
| 4.075 | | 2-O$-$$CHF_2$ | 4-O$-$$CHF_2$ | |
| 4.076 | | 2-$CH_3$ | 4-O$-$$CHF_2$ | |
| 4.077 | | 2-Cl | 4-O$-$$CF_3$ | |
| 4.078 | | 2-O$-$$CF_3$ | 4-O$-$$CH_3$ | |
| 4.079 | | 2-O$-$$CHF_2$ | 4-Cl | |
| 4.080 | | 2-O$-$$CHF_2$ | 6-$CH_3$ | |
| 4.081 | | 2-O$-$$CHF_2$ | 6-Cl | |
| 4.082 | 2-O$-$$CHF_2$ | 4-$CH_3$ | 6-$CH_3$ | |
| 4.083 | 2-$CH_3$ | 4-t-$C_4H_9$ | 6-$CH_3$ | |
| 4.084 | 2-i-$C_3H_7$ | 4-i-$C_3H_7$ | 6-i-$C_3H_7$ | |
| 4.085 | 2-$CH_3$ | 4-O$-$$CH_3$ | 6-$CH_3$ | |
| 4.086 | 2-Cl | 4-$CF_3$ | 6-Cl | |
| 4.087 | 2-Cl | 4-$CF_3$ | 6-F | |
| 4.088 | 2-Cl | 4-$NO_2$ | 6-Cl | |
| 4.089 | 2-Cl | 4-Cl | 6-Cl | |
| 4.090 | 2-F | 4-F | 6-F | |
| 4.091 | 2-$CH_3$ | 4-$NO_2$ | 6-$CH_3$ | |
| 4.092 | 2-Cl | 4-Cl | 6-$CH_3$ | |
| 4.093 | 2-Cl | 4-O$-$$CH_3$ | 6-Cl | |
| 4.094 | 2-Cl | 4-Cl | 6-O$-$$CH_3$ | |
| 4.095 | 2-F | 4-O$-$$CH_3$ | 6-F | |
| 4.096 | 2-O$-$$CH_3$ | 4-$CH_3$ | 6-O$-$$CH_3$ | |
| 4.097 | 2-O$-$$CH_3$ | 4-O$-$$CH_3$ | 6-$CH_3$ | |
| 4.098 | 2-O$-$$CH_3$ | 4-O$-$$CH_3$ | 6-O$-$$CH_3$ | |
| 4.099 | 2-O$-$$CH_3$ | 4-CO$-$O$-$$CH_3$ | 6-O$-$$CH_3$ | |
| 4.100 | 2-$CH_3$ | 4-Cl | 6-$CH_3$ | |
| 4.101 | 2-$CH_3$ | 4-F | 6-$CH_3$ | |
| 4.102 | 2-$CH_3$ | 4-$CH_3$ | 6-O$-$$CH_3$ | |

TABLE 4-continued
Compounds of the formula
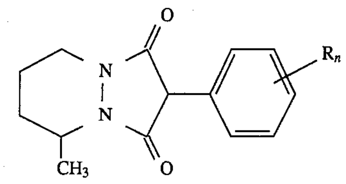
| Comp. No. | | $R_n$ | | Phys. data (°C.) |
|---|---|---|---|---|
| 4.103 | 2-F | 4-Cl | 5-O-i-$C_3H_7$ | |
| 4.104 | 2-Cl | 4-Cl | 5-O—$CH_3$ | |
| 4.105 | | 4-Cl | 5-O—$CH_3$ | |
| 4.106 | 2-F | 4-Cl | 5-CO—O—$CH_3$ | |
| 4.107 | 2-F | 4-Cl | 5-CO—O—$C_2H_5$ | |
| 4.108 | | 4-Cl | 5-CO—O—$CH_3$ | |
| 4.109 | 2-Cl | 4-Cl | 5-CO—O-i-$C_3H_7$ | |
| 4.110 | | 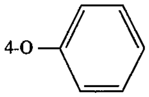 | | |
| 4.111 | | 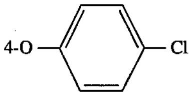 | | |
| 4.112 | | 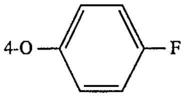 | | |
| 4.113 | | 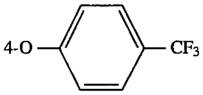 | | |
| 4.114 | 2-$CH_3$ | 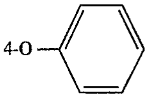 | | |
| 4.115 | | 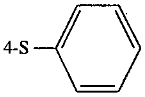 | | |
| 4.116 | | 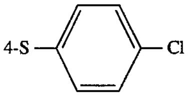 | | |
| 4.117 | | 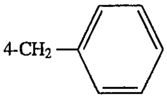 | | |
| 4.118 | | 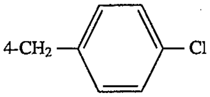 | | |
| 4.119 | | 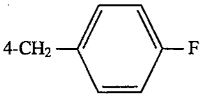 | | |
| 4.120 | | 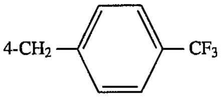 | | |

TABLE 4-continued

Compounds of the formula

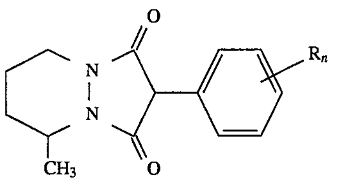

| Comp. No. | | $R_n$ | | Phys. data (°C.) |
|---|---|---|---|---|
| 4.121 | | 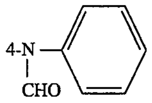 | | |
| 4.122 | 2-F | 4-Cl | $5\text{-}O-CH_2-CH=CH_2$ | |
| 4.123 | 2-F | 4-Cl | $5\text{-}O-CH_2-C\equiv CH$ | |

TABLE 5

Compounds of the formula

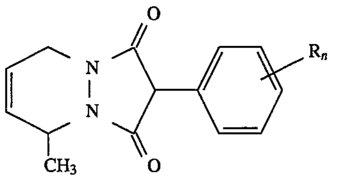

| Comp. No. | | $R_n$ | | Phys. data (°C.) |
|---|---|---|---|---|
| 5.001 | | H | | |
| 5.002 | | $2\text{-}CH_3$ | | |
| 5.003 | | $4\text{-}CH_3$ | | |
| 5.004 | | $2\text{-}CH_3$ | $4\text{-}CH_3$ | |
| 5.005 | | $2\text{-}CH_3$ | $6\text{-}CH_3$ | |
| 5.006 | | $2\text{-}CH_3$ | $5\text{-}CH_3$ | |
| 5.007 | | $3\text{-}CH_3$ | $5\text{-}CH_3$ | |
| 5.008 | | $2\text{-}CH_3$ | $3\text{-}CH_3$ | |
| 5.009 | | $3\text{-}CH_3$ | $4\text{-}CH_3$ | |
| 5.010 | $2\text{-}CH_3$ | $4\text{-}CH_3$ | $6\text{-}CH_3$ | |
| 5.011 | $2\text{-}CH_3$ | $4\text{-}CH_3$ | $5\text{-}CH_3$ | |
| 5.012 | | 2-Cl | | |
| 5.013 | | 4-Cl | | |
| 5.014 | | 2-Cl | 4-Cl | |
| 5.015 | | 2-Cl | 6-Cl | |
| 5.016 | | 2-Cl | 6-F | |
| 5.017 | | $2\text{-}CH_3$ | 4-Cl | |
| 5.018 | | $2\text{-}CH_3$ | 4-F | |
| 5.019 | | 2-Cl | $4\text{-}CH_3$ | |
| 5.020 | | 2-Cl | $6\text{-}CH_3$ | |
| 5.021 | | 2-F | 4-F | |
| 5.022 | | 2-F | 6-F | |
| 5.023 | | $2\text{-}CH_3$ | $4\text{-}O-CH_3$ | |
| 5.024 | | $2\text{-}CH_3$ | $6\text{-}O-CH_3$ | |
| 5.025 | | 2-Cl | $4\text{-}O-CH_3$ | |
| 5.026 | | 2-Cl | $6\text{-}O-CH_3$ | |
| 5.027 | | $3\text{-}OCH_3$ | $4\text{-}OCH_3$ | |
| 5.028 | | $2\text{-}OCH_3$ | $5\text{-}OCH_3$ | |
| 5.029 | | $2\text{-}OCH_3$ | $4\text{-}OCH_3$ | |
| 5.030 | | $2\text{-}OCH_3$ | $6\text{-}OCH_3$ | |
| 5.031 | | $2\text{-}CF_3$ | $6\text{-}CF_3$ | |
| 5.032 | | $2\text{-}CF_3$ | $4\text{-}CF_3$ | |
| 5.033 | | $3\text{-}CF_3$ | $5\text{-}CF_3$ | |
| 5.034 | | 2-Cl | $4\text{-}CF_3$ | |
| 5.035 | | 2-Cl | $6\text{-}CF_3$ | |
| 5.036 | | $2\text{-}NO_2$ | $4\text{-}NO_2$ | |

TABLE 5-continued

Compounds of the formula

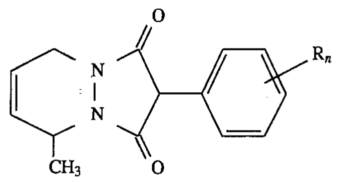

| Comp. No. | | $R_n$ | | Phys. data (°C.) |
|---|---|---|---|---|
| 5.037 | | 2-Cl | 4-$NO_2$ | |
| 5.038 | | 2-$CH_3$ | 4-$NO_2$ | |
| 5.039 | | 2-O$-$$CH_3$ | 4-$NO_2$ | |
| 5.040 | | 2-F | 6-$NO_2$ | |
| 5.041 | | 2-Cl | 6-$NO_2$ | |
| 5.042 | | 2-$CH_3$ | 6-$NO_2$ | |
| 5.043 | | 2-O$-$$CH_3$ | 6-$NO_2$ | |
| 5.044 | | 2-F | 4-$NO_2$ | |
| 5.045 | | 2-$CH_3$ | 4-$N(C_2H_5)_2$ | |
| 5.046 | | 2-Cl | 4-$SO_2-CH_3$ | |
| 5.047 | | 2-Cl | 4-$SO-CH_3$ | |
| 5.048 | | 2-Cl | 4-$S-CH_3$ | |
| 5.049 | | 2-Cl | 6-$SO_2-CH_3$ | |
| 5.050 | | 2-Cl | 6-$SO-CH_3$ | |
| 5.051 | | 2-Cl | 6-$S-CH_3$ | |
| 5.052 | | 2-$CH_3$ | 4-$SO_2-CH_3$ | |
| 5.053 | | 2-$CH_3$ | 4-$SO-CH_3$ | |
| 5.054 | | 2-$CH_3$ | 4-$S-CH_3$ | |
| 5.055 | | 2-$CH_3$ | 6-$SO_2-CH_3$ | |
| 5.056 | | 2-$CH_3$ | 6-$SO-CH_3$ | |
| 5.057 | | 2-$CH_3$ | 6-$S-CH_3$ | |
| 5.058 | | 2-O$-$$CH_3$ | 6-$SO_2-CH_3$ | |
| 5.059 | | 2-O$-$$CH_3$ | 6-$SO-CH_3$ | |
| 5.060 | | 2-O$-$$CH_3$ | 6-$S-CH_3$ | |
| 5.061 | | 2-O$-$$CH_3$ | 4-$SO_2-CH_3$ | |
| 5.062 | | 2-O$-$$CH_3$ | 4-$SO-CH_3$ | |
| 5.063 | | 2-O$-$$CH_3$ | 4-$S-CH_3$ | |
| 5.064 | | 2-$CH_3$ | 6-$N(C_2H_5)_2$ | |
| 5.065 | | 2-Cl | 6-$N(CH_3)_2$ | |
| 5.066 | | 2-Cl | 4-$N(CH_3)_2$ | |
| 5.067 | | 2-Cl | 4-$CO_2CH_3$ | |
| 5.068 | | 2-$CH_3$ | 6-$CO_2C_2H_5$ | |
| 5.069 | | 2-$CH_3$ | 4-$CO_2C_2H_5$ | |
| 5.070 | | 2-$CH_3$ | 4-CN | |
| 5.071 | | 2-$CH_3$ | 6-CN | |
| 5.072 | | 2-Cl | 4-CN | |
| 5.073 | | 2-Cl | 6-CN | |
| 5.074 | | 2-Cl | 4-$CO-CH_3$ | |
| 5.075 | | 2-O$-$$CHF_2$ | 4-O$-$$CHF_2$ | |
| 5.076 | | 2-$CH_3$ | 4-O$-$$CHF_2$ | |
| 5.077 | | 2-Cl | 4-O$-$$CF_3$ | |
| 5.078 | | 2-O$-$$CF_3$ | 4-O$-$$CH_3$ | |
| 5.079 | | 2-O$-$$CHF_2$ | 4-Cl | |
| 5.080 | | 2-O$-$$CHF_2$ | 6-$CH_3$ | |
| 5.081 | | 2-O$-$$CHF_2$ | 6-Cl | |
| 5.082 | 2-O$-$$CHF_2$ | 4-$CH_3$ | 6-$CH_3$ | |
| 5.083 | 2-$CH_3$ | 4-t-$C_4H_9$ | 6-$CH_3$ | |
| 5.084 | 2-i-$C_3H_7$ | 4-i-$C_3H_7$ | 6-i-$C_3H_7$ | |
| 5.085 | 2-$CH_3$ | 4-O$-$$CH_3$ | 6-$CH_3$ | |
| 5.086 | 2-Cl | 4-$CF_3$ | 6-Cl | |
| 5.087 | 2-Cl | 4-$CF_3$ | 6-F | |
| 5.088 | 2-Cl | 4-$NO_2$ | 6-Cl | |
| 5.089 | 2-Cl | 4-Cl | 6-Cl | |
| 5.090 | 2-F | 4-F | 6-F | |
| 5.091 | 2-$CH_3$ | 4-$NO_2$ | 6-$CH_3$ | |
| 5.092 | 2-Cl | 4-Cl | 6-$CH_3$ | |
| 5.093 | 2-Cl | 4-O$-$$CH_3$ | 6-Cl | |
| 5.094 | 2-Cl | 4-Cl | 6-O$-$$CH_3$ | |
| 5.095 | 2-F | 4-O$-$$CH_3$ | 6-F | |
| 5.096 | 2-O$-$$CH_3$ | 4-$CH_3$ | 6-O$-$$CH_3$ | |
| 5.097 | 2-O$-$$CH_3$ | 4-O$-$$CH_3$ | 6-$CH_3$ | |
| 5.098 | 2-O$-$$CH_3$ | 4-O$-$$CH_3$ | 6-O$-$$CH_3$ | |
| 5.099 | 2-O$-$$CH_3$ | 4-CO$-$O$-$$CH_3$ | 6-O$-$$CH_3$ | |
| 5.100 | 2-$CH_3$ | 4-Cl | 6-$CH_3$ | |
| 5.101 | 2-$CH_3$ | 4-F | 6-$CH_3$ | |

TABLE 5-continued
Compounds of the formula
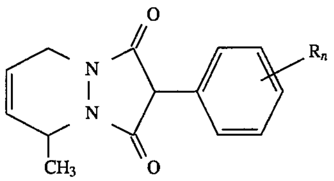
| Comp. No. | | $R_n$ | | Phys. data (°C.) |
|---|---|---|---|---|
| 5.102 | 2-$CH_3$ | 4-$CH_3$ | 6-O—$CH_3$ | |
| 5.103 | 2-F | 4-Cl | 5-O-i-$C_3H_7$ | |
| 5.104 | 2-Cl | 4-Cl | 5-O—$CH_3$ | |
| 5.105 | | 4-Cl | 5-O—$CH_3$ | |
| 5.106 | 2-F | 4-Cl | 5-CO—O—$CH_3$ | |
| 5.107 | 2-F | 4-Cl | 5-CO—O—$C_2H_5$ | |
| 5.108 | | 4-Cl | 5-CO—O—$CH_3$ | |
| 5.109 | 2-Cl | 4-Cl | 5-CO—O-i-$C_3H_7$ | |
| 5.110 | | 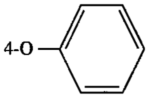 | | |
| 5.111 | | 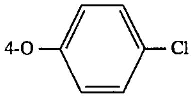 | | |
| 5.112 | | 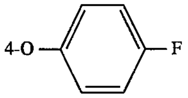 | | |
| 5.113 | | 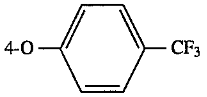 | | |
| 5.114 | 2-$CH_3$ | 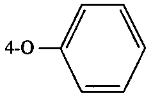 | | |
| 5.115 | | 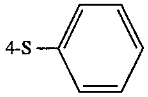 | | |
| 5.116 | | 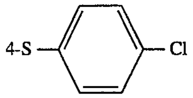 | | |
| 5.117 | | 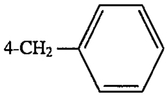 | | |
| 5.118 | | 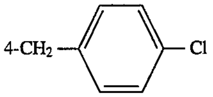 | | |
| 5.119 | | 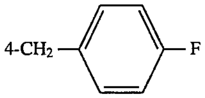 | | |

TABLE 5-continued

Compounds of the formula

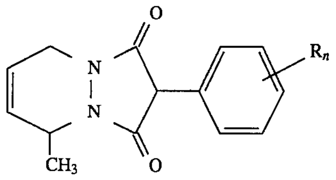

| Comp. No. | | $R_n$ | | Phys. data (°C.) |
|---|---|---|---|---|
| 5.120 | | 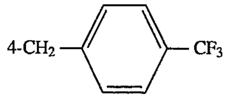 | | |
| 5.121 | | 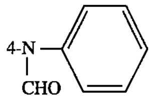 | | |
| 5.122 | 2-F | 4-Cl | $5\text{-}O-CH_2-CH=CH_2$ | |
| 5.123 | 2-F | 4-Cl | $5\text{-}O-CH_2-C\equiv CH$ | |

TABLE 6

Compounds of the formula

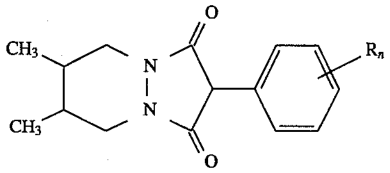

| Comp. No. | | $R_n$ | | Phys. data (°C.) |
|---|---|---|---|---|
| 6.001 | | H | | |
| 6.002 | | $2\text{-}CH_3$ | | |
| 6.003 | | $4\text{-}CH_3$ | | |
| 6.004 | | $2\text{-}CH_3$ | $4\text{-}CH_3$ | |
| 6.005 | | $2\text{-}CH_3$ | $6\text{-}CH_3$ | |
| 6.006 | | $2\text{-}CH_3$ | $5\text{-}CH_3$ | |
| 6.007 | | $3\text{-}CH_3$ | $5\text{-}CH_3$ | |
| 6.008 | | $2\text{-}CH_3$ | $3\text{-}CH_3$ | |
| 6.009 | | $3\text{-}CH_3$ | $4\text{-}CH_3$ | |
| 6.010 | $2\text{-}CH_3$ | $4\text{-}CH_3$ | $6\text{-}CH_3$ | m.p. 224 |
| 6.011 | $2\text{-}CH_3$ | $4\text{-}CH_3$ | $5\text{-}CH_3$ | |
| 6.012 | | 2-Cl | | |
| 6.013 | | 4-Cl | | |
| 6.014 | | 2-Cl | 4-Cl | |
| 6.015 | | 2-Cl | 6-Cl | |
| 6.016 | | 2-Cl | 6-F | |
| 6.017 | | $2\text{-}CH_3$ | 4-Cl | |
| 6.018 | | $2\text{-}CH_3$ | 4-F | |
| 6.019 | | 2-Cl | $4\text{-}CH_3$ | |
| 6.020 | | 2-Cl | $6\text{-}CH_3$ | |
| 6.021 | | 2-F | 4-F | |
| 6.022 | | 2-F | 6-F | |
| 6.023 | | $2\text{-}CH_3$ | $4\text{-}O-CH_3$ | |
| 6.024 | | $2\text{-}CH_3$ | $6\text{-}O-CH_3$ | |
| 6.025 | | 2-Cl | $4\text{-}O-CH_3$ | |
| 6.026 | | 2-Cl | $6\text{-}O-CH_3$ | |
| 6.027 | | $3\text{-}OCH_3$ | $4\text{-}OCH_3$ | |
| 6.028 | | $2\text{-}OCH_3$ | $5\text{-}OCH_3$ | |
| 6.029 | | $2\text{-}OCH_3$ | $4\text{-}OCH_3$ | |
| 6.030 | | $2\text{-}OCH_3$ | $6\text{-}OCH_3$ | |
| 6.031 | | $2\text{-}CF_3$ | $6\text{-}CF_3$ | |
| 6.032 | | $2\text{-}CF_3$ | $4\text{-}CF_3$ | |

TABLE 6-continued

Compounds of the formula

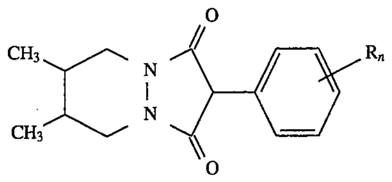

| Comp. No. | | $R_n$ | | Phys. data (°C.) |
|---|---|---|---|---|
| 6.033 | | $3\text{-}CF_3$ | $5\text{-}CF_3$ | |
| 6.034 | | 2-Cl | $4\text{-}CF_3$ | |
| 6.035 | | 2-Cl | $6\text{-}CF_3$ | |
| 6.036 | | $2\text{-}NO_2$ | $4\text{-}NO_2$ | |
| 6.037 | | 2-Cl | $4\text{-}NO_2$ | |
| 6.038 | | $2\text{-}CH_3$ | $4\text{-}NO_2$ | |
| 6.039 | | $2\text{-}O-CH_3$ | $4\text{-}NO_2$ | |
| 6.040 | | 2-F | $6\text{-}NO_2$ | |
| 6.041 | | 2-Cl | $6\text{-}NO_2$ | |
| 6.042 | | $2\text{-}CH_3$ | $6\text{-}NO_2$ | |
| 6.043 | | $2\text{-}O-CH_3$ | $6\text{-}NO_2$ | |
| 6.044 | | 2-F | $4\text{-}NO_2$ | |
| 6.045 | | $2\text{-}CH_3$ | $4\text{-}N(C_2H_5)_2$ | |
| 6.046 | | 2-Cl | $4\text{-}SO_2-CH_3$ | |
| 6.047 | | 2-Cl | $4\text{-}SO-CH_3$ | |
| 6.048 | | 2-Cl | $4\text{-}S-CH_3$ | |
| 6.049 | | 2-Cl | $6\text{-}SO_2-CH_3$ | |
| 6.050 | | 2-Cl | $6\text{-}SO-CH_3$ | |
| 6.051 | | 2-Cl | $6\text{-}S-CH_3$ | |
| 6.052 | | $2\text{-}CH_3$ | $4\text{-}SO_2-CH_3$ | |
| 6.053 | | $2\text{-}CH_3$ | $4\text{-}SO-CH_3$ | |
| 6.054 | | $2\text{-}CH_3$ | $4\text{-}S-CH_3$ | |
| 6.055 | | $2\text{-}CH_3$ | $6\text{-}SO_2-CH_3$ | |
| 6.056 | | $2\text{-}CH_3$ | $6\text{-}SO-CH_3$ | |
| 6.057 | | $2\text{-}CH_3$ | $6\text{-}S-CH_3$ | |
| 6.058 | | $2\text{-}O-CH_3$ | $6\text{-}SO_2-CH_3$ | |
| 6.059 | | $2\text{-}O-CH_3$ | $6\text{-}SO-CH_3$ | |
| 6.060 | | $2\text{-}O-CH_3$ | $6\text{-}S-CH_3$ | |
| 6.061 | | $2\text{-}O-CH_3$ | $4\text{-}SO_2-CH_3$ | |
| 6.062 | | $2\text{-}O-CH_3$ | $4\text{-}SO-CH_3$ | |
| 6.063 | | $2\text{-}O-CH_3$ | $4\text{-}S-CH_3$ | |
| 6.064 | | $2\text{-}CH_3$ | $6\text{-}N(C_2H_5)_2$ | |
| 6.065 | | 2-Cl | $6\text{-}N(CH_3)_2$ | |
| 6.066 | | 2-Cl | $4\text{-}N(CH_3)_2$ | |
| 6.067 | | 2-Cl | $4\text{-}CO_2CH_3$ | |
| 6.068 | | $2\text{-}CH_3$ | $6\text{-}CO_2C_2H_5$ | |
| 6.069 | | $2\text{-}CH_3$ | $4\text{-}CO_2C_2H_5$ | |
| 6.070 | | $2\text{-}CH_3$ | 4-CN | |
| 6.071 | | $2\text{-}CH_3$ | 6-CN | |
| 6.072 | | 2-Cl | 4-CN | |
| 6.073 | | 2-Cl | 6-CN | |
| 6.074 | | 2-Cl | $4\text{-}CO-CH_3$ | |
| 6.075 | | $2\text{-}O-CHF_2$ | $4\text{-}O-CHF_2$ | |
| 6.076 | | $2\text{-}CH_3$ | $4\text{-}O-CHF_2$ | |
| 6.077 | | 2-Cl | $4\text{-}O-CF_3$ | |
| 6.078 | | $2\text{-}O-CF_3$ | $4\text{-}O-CH_3$ | |
| 6.079 | | $2\text{-}O-CHF_2$ | 4-Cl | |
| 6.080 | | $2\text{-}O-CHF_2$ | $6\text{-}CH_3$ | |
| 6.081 | | $2\text{-}O-CHF_2$ | 6-Cl | |
| 6.082 | $2\text{-}O-CHF_2$ | $4\text{-}CH_3$ | $6\text{-}CH_3$ | |
| 6.083 | $2\text{-}CH_3$ | $4\text{-}t\text{-}C_4H_9$ | $6\text{-}CH_3$ | |
| 6.084 | $2\text{-}i\text{-}C_3H_7$ | $4\text{-}i\text{-}C_3H_7$ | $6\text{-}i\text{-}C_3H_7$ | |
| 6.085 | $2\text{-}CH_3$ | $4\text{-}O\text{-}CH_3$ | $6\text{-}CH_3$ | |
| 6.086 | 2-Cl | $4\text{-}CF_3$ | 6-Cl | |
| 6.087 | 2-Cl | $4\text{-}CF_3$ | 6-F | |
| 6.088 | 2-Cl | $4\text{-}NO_2$ | 6-Cl | |
| 6.089 | 2-Cl | 4-Cl | 6-Cl | |
| 6.090 | 2-F | 4-F | 6-F | |
| 6.091 | $2\text{-}CH_3$ | $4\text{-}NO_2$ | $6\text{-}CH_3$ | |
| 6.092 | 2-Cl | 4-Cl | $6\text{-}CH_3$ | |
| 6.093 | 2-Cl | $4\text{-}O-CH_3$ | 6-Cl | |
| 6.094 | 2-Cl | 4-Cl | $6\text{-}O-CH_3$ | |
| 6.095 | 2-F | $4\text{-}O-CH_3$ | 6-F | |
| 6.096 | $2\text{-}O-CH_3$ | $4\text{-}CH_3$ | $6\text{-}O-CH_3$ | |
| 6.097 | $2\text{-}O-CH_3$ | $4\text{-}O-CH_3$ | $6\text{-}CH_3$ | |

TABLE 6-continued
Compounds of the formula
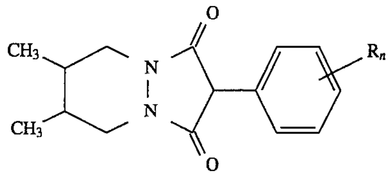
| Comp. No. | $R_n$ | | | Phys. data (°C.) |
|---|---|---|---|---|
| 6.098 | 2-O—$CH_3$ | 4-O—$CH_3$ | 6-O—$CH_3$ | |
| 6.099 | 2-O—$CH_3$ | 4-CO—O—$CH_3$ | 6-O—$CH_3$ | |
| 6.100 | 2-$CH_3$ | 4-Cl | 6-$CH_3$ | |
| 6.101 | 2-$CH_3$ | 4-F | 6-$CH_3$ | |
| 6.102 | 2-$CH_3$ | 4-$CH_3$ | 6-O—$CH_3$ | |
| 6.103 | 2-F | 4-Cl | 5-O-i-$C_3H_7$ | |
| 6.104 | 2-Cl | 4-Cl | 5-O—$CH_3$ | |
| 6.105 | | 4-Cl | 5-O—$CH_3$ | |
| 6.106 | 2-F | 4-Cl | 5-CO—O—$CH_3$ | |
| 6.107 | 2-F | 4-Cl | 5-CO—O—$C_2H_5$ | |
| 6.108 | | 4-Cl | 5-CO—O—$CH_3$ | |
| 6.109 | 2-Cl | 4-Cl | 5-CO—O-i-$C_3H_7$ | |
| 6.110 | | 4-O 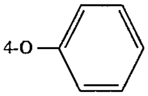 | | |
| 6.111 | | 4-O 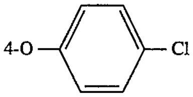 | | |
| 6.112 | | 4-O 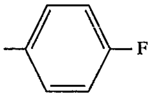 | | |
| 6.113 | | 4-O 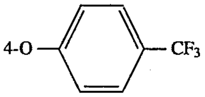 | | |
| 6.114 | 2-$CH_3$ | 4-O 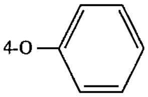 | | |
| 6.115 | | 4-S 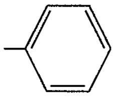 | | |
| 6.116 | | 4-S 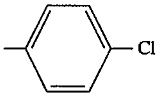 | | |
| 6.117 | | 4-$CH_2$ 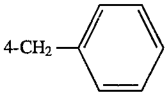 | | |
| 6.118 | | 4-$CH_2$ 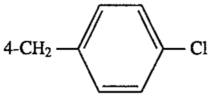 | | |
| 6.119 | | 4-$CH_2$ 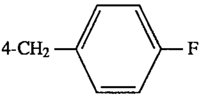 | | |

TABLE 6-continued
Compounds of the formula
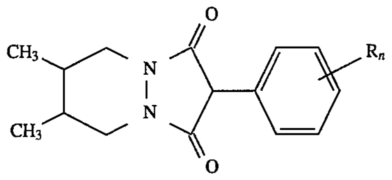
| Comp. No. | | $R_n$ | | Phys. data (°C.) |
|---|---|---|---|---|
| 6.120 | | 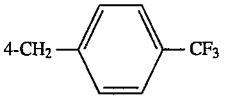 | | |
| 6.121 | | 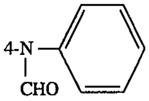 | | |
| 6.122 | 2-F | 4-Cl | 5-O$-CH_2-CH=CH_2$ | |
| 6.123 | 2-F | 4-Cl | 5-O$-CH_2-C\equiv CH$ | |
| 6.124 | 2-Br | | | |
| 6.125 | 2-$CF_3$ | | | |
| 6.126 | 2-$OCH_3$ | | | |
| 6.127 | 2-$CH_3$ | 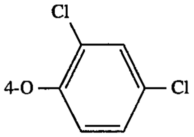 | | |
| 6.128 | 2-$CH_3$ | 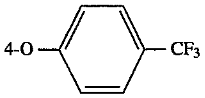 | | |
| 6.129 | 2-$CH_3$ | 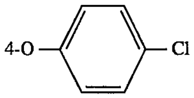 | | |
| 6.130 | 2-$CH_3$ | 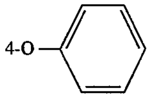 | 6-$CH_3$ | |
| 6.131 | 2-$CH_3$ | 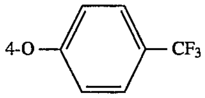 | 6-$CH_3$ | |
| 6.132 | 2-$CH_3$ | 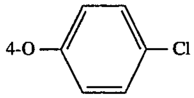 | 6-$CH_3$ | |
| 6.133 | 2-$CH_3$ | 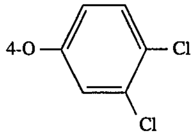 | 6-$CH_3$ | |
| 6.134 | 2-$CH_3$ | 4-Br | 6-$CH_3$ | |
| 6.135 | 2-$CH_3$ | 6-$C_2H_5$ | | |
| 6.136 | 2-$C_2H_5$ | 6-$C_2H_5$ | | |
| 6.137 | 2-$CH_3$ | 4-$OC_2H_5$ | 6-$CH_3$ | |
| 6.138 | 2-$CH_3$ | 4-O-i-$C_3H_7$ | 6-$CH_3$ | |

TABLE 6-continued
Compounds of the formula
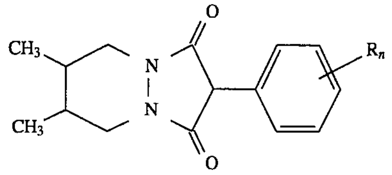
| Comp. No. | | $R_n$ | | Phys. data (°C.) |
|---|---|---|---|---|
| 6.139 | 2-$CH_3$ | 4-O-n-$C_3H_7$ | 6-$CH_3$ | |
| 6.140 | 2-$CH_3$ | 4-O-n-$C_{10}H_{21}$ | 6-$CH_3$ | |
| 6.141 | 2-$CH_3$ | 4-O-n-$C_3H_7$ | | |
| 6.142 | 2-$CH_3$ | 4-O$-(CH_2)_2OCH_3$ | | |
| 6.143 | 2-$CH_3$ | 4-O$-(CH_2)_2OCH_3$ | 6-$CH_3$ | |
| 6.144 | 2-$CH_3$ | 4-O$-(CH_2)_2OCH_3$ | | |
| 6.145 | 2-$CH_3$ | 4-O-n-$C_6H_{13}$ | 6-$CH_3$ | |
| 6.146 | 2-$CH_3$ | 4-$CH_2$ 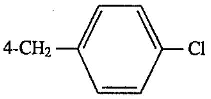 | | |
| 6.147 | 2-$CH_3$ | 4-O 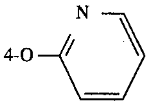 | 6-$CH_3$ | |
| 6.148 | 2-$CH_3$ | 4-O 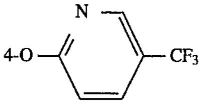 | | |
| 6.149 | 2-$CH_3$ | 4-O 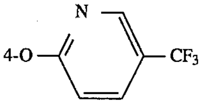 | 6-$CH_3$ | |
| 6.150 | 2-$CH_3$ | 4-O 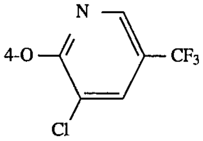 | | |
| 6.151 | 2-$CH_3$ | 4-O 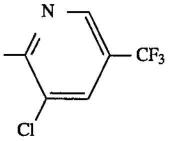 | 6-$CH_3$ | |
| 6.152 | 2-$CH_3$ | 5-O 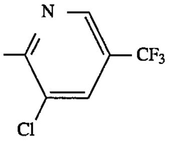 | | |
| 6.153 | 2-$CH_3$ | 5-O 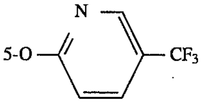 | | |
| 6.154 | 2-$CH_3$ | 4-S 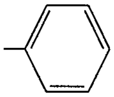 | 6-$CH_3$ | |

TABLE 6-continued

Compounds of the formula

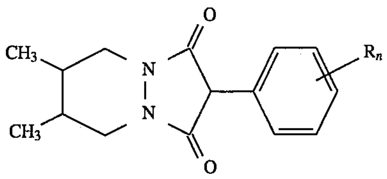

| Comp. No. | | $R_n$ | | Phys. data (°C.) |
|---|---|---|---|---|
| 6.155 | 2-$CH_3$ | 4-S 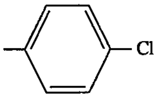 | 6-$CH_3$ | |
| 6.156 | 2-$C_2H_5$ | 4-S 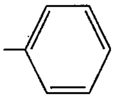 | 6-$CH_3$ | |

TABLE 7

Compounds of the formula

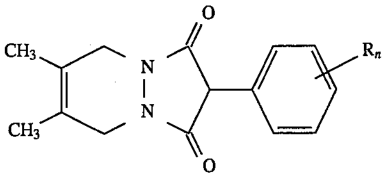

| Comp. No. | | $R_n$ | | Phys. data (°C.) |
|---|---|---|---|---|
| 7.001 | | H | | |
| 7.002 | | 2-$CH_3$ | | |
| 7.003 | | 4-$CH_3$ | | |
| 7.004 | | 2-$CH_3$ | 4-$CH_3$ | |
| 7.005 | | 2-$CH_3$ | 6-$CH_3$ | |
| 7.006 | | 2-$CH_3$ | 5-$CH_3$ | |
| 7.007 | | 3-$CH_3$ | 5-$CH_3$ | |
| 7.008 | | 2-$CH_3$ | 3-$CH_3$ | |
| 7.009 | | 3-$CH_3$ | 4-$CH_3$ | |
| 7.010 | 2-$CH_3$ | 4-$CH_3$ | 6-$CH_3$ | |
| 7.011 | 2-$CH_3$ | 4-$CH_3$ | 5-$CH_3$ | |
| 7.012 | | 2-Cl | | |
| 7.013 | | 4-Cl | | |
| 7.014 | | 2-Cl | 4-Cl | |
| 7.015 | | 2-Cl | 6-Cl | |
| 7.016 | | 2-Cl | 6-F | |
| 7.017 | | 2-$CH_3$ | 4-Cl | |
| 7.018 | | 2-$CH_3$ | 4-F | |
| 7.019 | | 2-Cl | 4-$CH_3$ | |
| 7.020 | | 2-Cl | 6-$CH_3$ | |
| 7.021 | | 2-F | 4-F | |
| 7.022 | | 2-F | 6-F | |
| 7.023 | | 2-$CH_3$ | 4-O—$CH_3$ | |
| 7.024 | | 2-$CH_3$ | 6-O—$CH_3$ | |
| 7.025 | | 2-Cl | 4-O—$CH_3$ | |
| 7.026 | | 2-Cl | 6-O—$CH_3$ | |
| 7.027 | | 3-$OCH_3$ | 4-$OCH_3$ | |
| 7.028 | | 2-$OCH_3$ | 5-$OCH_3$ | |
| 7.029 | | 2-$OCH_3$ | 4-$OCH_3$ | |
| 7.030 | | 2-$OCH_3$ | 6-$OCH_3$ | |
| 7.031 | | 2-$CF_3$ | 6-$CF_3$ | |
| 7.032 | | 2-$CF_3$ | 4-$CF_3$ | |
| 7.033 | | 3-$CF_3$ | 5-$CF_3$ | |
| 7.034 | | 2-Cl | 4-$CF_3$ | |
| 7.035 | | 2-Cl | 6-$CF_3$ | |
| 7.036 | | 2-$NO_2$ | 4-$NO_2$ | |
| 7.037 | | 2-Cl | 4-$NO_2$ | |

TABLE 7-continued

Compounds of the formula

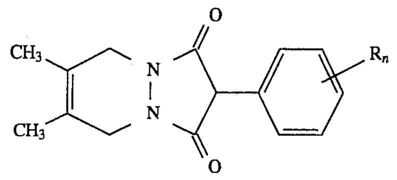

| Comp. No. | | $R_n$ | | Phys. data (°C.) |
|---|---|---|---|---|
| 7.038 | | 2-$CH_3$ | 4-$NO_2$ | |
| 7.039 | | 2-O$-$$CH_3$ | 4-$NO_2$ | |
| 7.040 | | 2-F | 6-$NO_2$ | |
| 7.041 | | 2-Cl | 6-$NO_2$ | |
| 7.042 | | 2-$CH_3$ | 6-$NO_2$ | |
| 7.043 | | 2-O$-$$CH_3$ | 6-$NO_2$ | |
| 7.044 | | 2-F | 4-$NO_2$ | |
| 7.045 | | 2-$CH_3$ | 4-$N(C_2H_5)_2$ | |
| 7.046 | | 2-Cl | 4-$SO_2$$-$$CH_3$ | |
| 7.047 | | 2-Cl | 4-SO$-$$CH_3$ | |
| 7.048 | | 2-Cl | 4-S$-$$CH_3$ | |
| 7.049 | | 2-Cl | 6-$SO_2$$-$$CH_3$ | |
| 7.050 | | 2-Cl | 6-SO$-$$CH_3$ | |
| 7.051 | | 2-Cl | 6-S$-$$CH_3$ | |
| 7.052 | | 2-$CH_3$ | 4-$SO_2$$-$$CH_3$ | |
| 7.053 | | 2-$CH_3$ | 4-SO$-$$CH_3$ | |
| 7.054 | | 2-$CH_3$ | 4-S$-$$CH_3$ | |
| 7.055 | | 2-$CH_3$ | 6-$SO_2$$-$$CH_3$ | |
| 7.056 | | 2-$CH_3$ | 6-SO$-$$CH_3$ | |
| 7.057 | | 2-$CH_3$ | 6-S$-$$CH_3$ | |
| 7.058 | | 2-O$-$$CH_3$ | 6-$SO_2$$-$$CH_3$ | |
| 7.059 | | 2-O$-$$CH_3$ | 6-SO$-$$CH_3$ | |
| 7.060 | | 2-O$-$$CH_3$ | 6-S$-$$CH_3$ | |
| 7.061 | | 2-O$-$$CH_3$ | 4-$SO_2$$-$$CH_3$ | |
| 7.062 | | 2-O$-$$CH_3$ | 4-SO$-$$CH_3$ | |
| 7.063 | | 2-O$-$$CH_3$ | 4-S$-$$CH_3$ | |
| 7.064 | | 2-$CH_3$ | 6-$N(C_2H_5)_2$ | |
| 7.065 | | 2-Cl | 6-$N(CH_3)_2$ | |
| 7.066 | | 2-Cl | 4-$N(CH_3)_2$ | |
| 7.067 | | 2-Cl | 4-$CO_2CH_3$ | |
| 7.068 | | 2-$CH_3$ | 6-$CO_2C_2H_5$ | |
| 7.069 | | 2-$CH_3$ | 4-$CO_2C_2H_5$ | |
| 7.070 | | 2-$CH_3$ | 4-CN | |
| 7.071 | | 2-$CH_3$ | 6-CN | |
| 7.072 | | 2-Cl | 4-CN | |
| 7.073 | | 2-Cl | 6-CN | |
| 7.074 | | 2-Cl | 4-CO$-$$CH_3$ | |
| 7.075 | | 2-O$-$$CHF_2$ | 4-O$-$$CHF_2$ | |
| 7.076 | | 2-$CH_3$ | 4-O$-$$CHF_2$ | |
| 7.077 | | 2-Cl | 4-O$-$$CF_3$ | |
| 7.078 | | 2-O$-$$CF_3$ | 4-O$-$$CH_3$ | |
| 7.079 | | 2-O$-$$CHF_2$ | 4-Cl | |
| 7.080 | | 2-O$-$$CHF_2$ | 6-$CH_3$ | |
| 7.081 | | 2-O$-$$CHF_2$ | 6-Cl | |
| 7.082 | 2-O$-$$CHF_2$ | 4-$CH_3$ | 6-$CH_3$ | |
| 7.083 | 2-$CH_3$ | 4-t-$C_4H_9$ | 6-$CH_3$ | |
| 7.084 | 2-i-$C_3H_7$ | 4-i-$C_3H_7$ | 6-i-$C_3H_7$ | |
| 7.085 | 2-$CH_3$ | 4-O$-$$CH_3$ | 6-$CH_3$ | |
| 7.086 | 2-Cl | 4-$CF_3$ | 6-Cl | |
| 7.087 | 2-Cl | 4-$CF_3$ | 6-F | |
| 7.098 | 2-Cl | 4-$NO_2$ | 6-Cl | |
| 7.089 | 2-Cl | 4-Cl | 6-Cl | |
| 7.090 | 2-F | 4-F | 6-F | |
| 7.091 | 2-$CH_3$ | 4-NO | 6-$CH_3$ | |
| 7.092 | 2-Cl | 4-Cl | 6-$CH_3$ | |
| 7.093 | 2-Cl | 4-O$-$$CH_3$ | 6-Cl | |
| 7.094 | 2-Cl | 4-Cl | 6-O$-$$CH_3$ | |
| 7.095 | 2-F | 4-O$-$$CH_3$ | 6-F | |
| 7.096 | 2-O$-$$CH_3$ | 4-$CH_3$ | 6-O$-$$CH_3$ | |
| 7.097 | 2-O$-$$CH_3$ | 4-O$-$$CH_3$ | 6-$CH_3$ | |
| 7.098 | 2-O$-$$CH_3$ | 4-O$-$$CH_3$ | 6-O$-$$CH_3$ | |
| 7.099 | 2-O$-$$CH_3$ | 4-CO$-$O$-$$CH_3$ | 6-O$-$$CH_3$ | |
| 7.100 | 2-$CH_3$ | 4-Cl | 6-$CH_3$ | |
| 7.101 | 2-$CH_3$ | 4-F | 6-$CH_3$ | |
| 7.102 | 2-$CH_3$ | 4-$CH_3$ | 6-O$-$$CH_3$ | |

TABLE 7-continued
Compounds of the formula
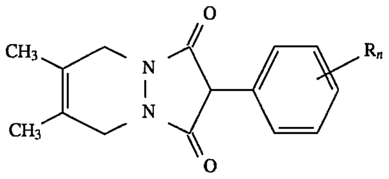
| Comp. No. | | $R_n$ | | Phys. data (°C.) |
|---|---|---|---|---|
| 7.103 | 2-F | 4-Cl | 5-O-i-$C_3H_7$ | |
| 7.104 | 2-Cl | 4-Cl | 5-O$-CH_3$ | |
| 7.105 | | 4-Cl | 5-O$-CH_3$ | |
| 7.106 | 2-F | 4-Cl | 5-CO$-$O$-CH_3$ | |
| 7.107 | 2-F | 4-Cl | 5-CO$-$O$-C_2H_5$ | |
| 7.108 | | 4-Cl | 5-CO$-$O$-CH_3$ | |
| 7.109 | 2-Cl | 4-Cl | 5-CO$-$O-i-$C_3H_7$ | |
| 7.110 | | 4-O 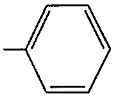 | | |
| 7.111 | | 4-O 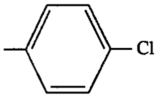 | | |
| 7.112 | | 4-O 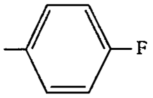 | | |
| 7.113 | | 4-O 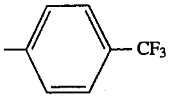 | | |
| 7.114 | 2-$CH_3$ | 4-O 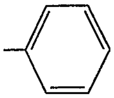 | | |
| 7.115 | | 4-S 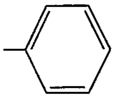 | | |
| 7.116 | | 4-S 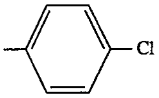 | | |
| 7.117 | | 4-$CH_2$ 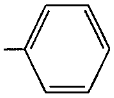 | | |
| 7.118 | | 4-$CH_2$ 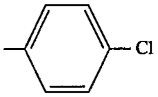 | | |
| 7.119 | | 4-$CH_2$ 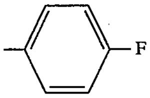 | | |
| 7.120 | | 4-$CH_2$ 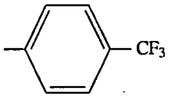 | | |

TABLE 7-continued

Compounds of the formula

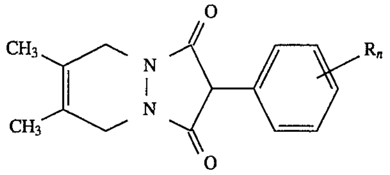

| Comp. No. | | $R_n$ | | Phys. data (°C.) |
|---|---|---|---|---|
| 7.121 | | 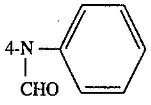 | | |
| 7.122 | 2-F | 4-Cl | 5-O$-CH_2-CH=CH_2$ | |
| 7.123 | 2-F | 4-Cl | 5-O$-CH_2-C\equiv CH$ | |

TABLE 8

Compounds of the formula

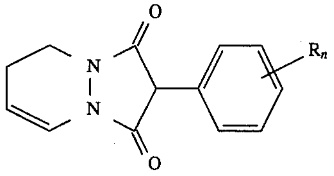

| Comp. No. | | $R_n$ | | Phys. data (°C.) |
|---|---|---|---|---|
| 8.001 | | H | | |
| 8.002 | | 2-$CH_3$ | | |
| 8.003 | | 4-$CH_3$ | | |
| 8.004 | | 2-$CH_3$ | 4-$CH_3$ | |
| 8.005 | | 2-$CH_3$ | 6-$CH_3$ | |
| 8.006 | | 2-$CH_3$ | 5-$CH_3$ | |
| 8.007 | | 3-$CH_3$ | 5-$CH_3$ | |
| 8.008 | | 2-$CH_3$ | 3-$CH_3$ | |
| 8.009 | | 3-$CH_3$ | 4-$CH_3$ | |
| 8.010 | 2-$CH_3$ | 4-$CH_3$ | 6-$CH_3$ | |
| 8.011 | 2-$CH_3$ | 4-$CH_3$ | 5-$CH_3$ | |
| 8.012 | | 2-Cl | | |
| 8.013 | | 4-Cl | | |
| 8.014 | | 2-Cl | 4-Cl | |
| 8.015 | | 2-Cl | 6-Cl | |
| 8.016 | | 2-Cl | 6-F | |
| 8.017 | | 2-$CH_3$ | 4-Cl | |
| 8.018 | | 2-$CH_3$ | 4-F | |
| 8.019 | | 2-Cl | 4-$CH_3$ | |
| 8.020 | | 2-Cl | 6-$CH_3$ | |
| 8.021 | | 2-F | 4-F | |
| 8.022 | | 2-F | 6-F | |
| 8.023 | | 2-$CH_3$ | 4-O$-CH_3$ | |
| 8.024 | | 2-$CH_3$ | 6-O$-CH_3$ | |
| 8.025 | | 2-Cl | 4-O$-CH_3$ | |
| 8.026 | | 2-Cl | 6-O$-CH_3$ | |
| 8.027 | | 3-$OCH_3$ | 4-$OCH_3$ | |
| 8.028 | | 2-$OCH_3$ | 5-$OCH_3$ | |
| 8.029 | | 2-$OCH_3$ | 4-$OCH_3$ | |
| 8.030 | | 2-$OCH_3$ | 6-$OCH_3$ | |
| 8.031 | | 2-$CF_3$ | 6-$CF_3$ | |
| 8.032 | | 2-$CF_3$ | 4-$CF_3$ | |
| 8.033 | | 3-$CF_3$ | 5-$CF_3$ | |
| 8.034 | | 2-Cl | 4-$CF_3$ | |
| 8.035 | | 2-Cl | 6-$CF_3$ | |
| 8.036 | | 2-$NO_2$ | 4-$NO_2$ | |

TABLE 8-continued

Compounds of the formula

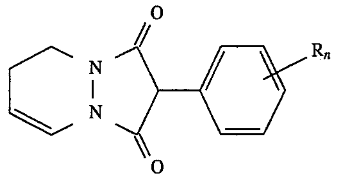

| Comp. No. | | $R_n$ | | Phys. data (°C.) |
|---|---|---|---|---|
| 8.037 | | 2-Cl | $4-NO_2$ | |
| 8.038 | | $2-CH_3$ | $4-NO_2$ | |
| 8.039 | | $2-O-CH_3$ | $4-NO_2$ | |
| 8.040 | | 2-F | $6-NO_2$ | |
| 8.041 | | 2-Cl | $6-NO_2$ | |
| 8.042 | | $2-CH_3$ | $6-NO_2$ | |
| 8.043 | | $2-O-CH_3$ | $6-NO_2$ | |
| 8.044 | | 2-F | $4-NO_2$ | |
| 8.045 | | $2-CH_3$ | $4-N(C_2H_5)_2$ | |
| 8.046 | | 2-Cl | $4-SO_2-CH_3$ | |
| 8.047 | | 2-Cl | $4-SO-CH_3$ | |
| 8.048 | | 2-Cl | $4-S-CH_3$ | |
| 8.049 | | 2-Cl | $6-SO_2-CH_3$ | |
| 8.050 | | 2-Cl | $6-SO-CH_3$ | |
| 8.051 | | 2-Cl | $6-S-CH_3$ | |
| 8.052 | | $2-CH_3$ | $4-SO_2-CH_3$ | |
| 8.053 | | $2-CH_3$ | $4-SO-CH_3$ | |
| 8.054 | | $2-CH_3$ | $4-S-CH_3$ | |
| 8.055 | | $2-CH_3$ | $6-SO_2-CH_3$ | |
| 8.056 | | $2-CH_3$ | $6-SO-CH_3$ | |
| 8.057 | | $2-CH_3$ | $6-S-CH_3$ | |
| 8.058 | | $2-O-CH_3$ | $6-SO_2-CH_3$ | |
| 8.059 | | $2-O-CH_3$ | $6-SO-CH_3$ | |
| 8.060 | | $2-O-CH_3$ | $6-S-CH_3$ | |
| 8.061 | | $2-O-CH_3$ | $4-SO_2-CH_3$ | |
| 8.062 | | $2-O-CH_3$ | $4-SO-CH_3$ | |
| 8.063 | | $2-O-CH_3$ | $4-S-CH_3$ | |
| 8.064 | | $2-CH_3$ | $6-N(C_2H_5)_2$ | |
| 8.065 | | 2-Cl | $6-N(CH_3)_2$ | |
| 8.066 | | 2-Cl | $4-N(CH_3)_2$ | |
| 8.067 | | 2-Cl | $4-CO_2CH_3$ | |
| 8.068 | | $2-CH_3$ | $6-CO_2C_2H_5$ | |
| 8.069 | | $2-CH_3$ | $4-CO_2C_2H_5$ | |
| 8.070 | | $2-CH_3$ | 4-CN | |
| 8.071 | | $2-CH_3$ | 6-CN | |
| 8.072 | | 2-Cl | 4-CN | |
| 8.073 | | 2-Cl | 6-CN | |
| 8.074 | | 2-Cl | $4-CO-CH_3$ | |
| 8.075 | | $2-O-CHF_2$ | $4-O-CHF_2$ | |
| 8.076 | | $2-CH_3$ | $4-O-CHF_2$ | |
| 8.077 | | 2-Cl | $4-O-CF_3$ | |
| 8.078 | | $2-O-CF_3$ | $4-O-CH_3$ | |
| 8.079 | | $2-O-CHF_2$ | 4-Cl | |
| 8.080 | | $2-O-CHF_2$ | $6-CH_3$ | |
| 8.081 | | $2-O-CHF_2$ | 6-Cl | |
| 8.082 | $2-O-CHF_2$ | $4-CH_3$ | $6-CH_3$ | |
| 8.083 | $2-CH_3$ | $4-t-C_4H_9$ | $6-CH_3$ | |
| 8.084 | $2-i-C_3H_7$ | $4-i-C_3H_7$ | $6-i-C_3H_7$ | |
| 8.085 | $2-CH_3$ | $4-O-CH_3$ | $6-CH_3$ | |
| 8.086 | 2-Cl | $4-CF_3$ | 6-Cl | |
| 8.087 | 2-Cl | $4-CF_3$ | 6-F | |
| 8.088 | 2-Cl | $4-NO_2$ | 6-Cl | |
| 8.089 | 2-Cl | 4-Cl | 6-Cl | |
| 8.090 | 2-F | 4-F | 6-F | |
| 8.091 | $2-CH_3$ | $4-NO_2$ | $6-CH_3$ | |
| 8.092 | 2-Cl | 4-Cl | $6-CH_3$ | |
| 8.093 | 2-Cl | $4-O-CH_3$ | 6-Cl | |
| 8.094 | 2-Cl | 4-Cl | $6-O-CH_3$ | |
| 8.095 | 2-F | $4-O-CH_3$ | 6-F | |
| 8.096 | $2-O-CH_3$ | $4-CH_3$ | $6-O-CH_3$ | |
| 8.097 | $2-O-CH_3$ | $4-O-CH_3$ | $6-CH_3$ | |
| 8.098 | $2-O-CH_3$ | $4-O-CH_3$ | $6-O-CH_3$ | |
| 8.099 | $2-O-CH_3$ | $4-CO-O-CH_3$ | $6-O-CH_3$ | |
| 8.100 | $2-CH_3$ | 4-Cl | $6-CH_3$ | |
| 8.101 | $2-CH_3$ | 4-F | $6-CH_3$ | |

TABLE 8-continued
Compounds of the formula
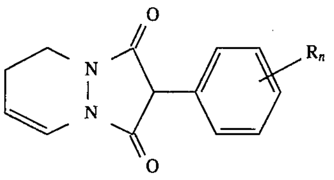
| Comp. No. | | $R_n$ | | Phys. data (°C.) |
|---|---|---|---|---|
| 8.102 | 2-$CH_3$ | 4-$CH_3$ | 6-O−$CH_3$ | |
| 8.103 | 2-F | 4-Cl | 5-O-i-$C_3H_7$ | |
| 8.104 | 2-Cl | 4-Cl | 5-O−$CH_3$ | |
| 8.105 | | 4-Cl | 5-O−$CH_3$ | |
| 8.106 | 2-F | 4-Cl | 5-CO−O−$CH_3$ | |
| 8.107 | 2-F | 4-Cl | 5-CO−O−$C_2H_5$ | |
| 8.108 | | 4-Cl | 5-CO−O−$CH_3$ | |
| 8.109 | 2-Cl | 4-Cl | 5-CO−O-i-$C_3H_7$ | |
| 8.110 | | 4-O 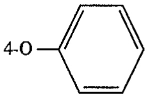 | | |
| 8.111 | | 4-O 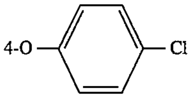 Cl | | |
| 8.112 | | 4-O 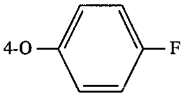 F | | |
| 8.113 | | 4-O 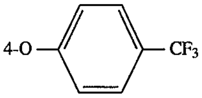 $CF_3$ | | |
| 8.114 | 2-$CH_3$ | 4-O 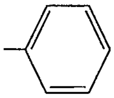 | | |
| 8.115 | | 4-S 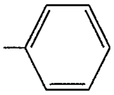 | | |
| 8.116 | | 4-S 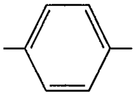 Cl | | |
| 8.117 | | 4-$CH_2$ 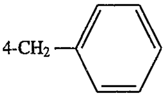 | | |
| 8.118 | | 4-$CH_2$ 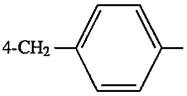 Cl | | |
| 8.119 | | 4-$CH_2$ 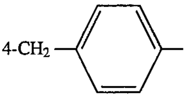 F | | |

TABLE 8-continued

Compounds of the formula

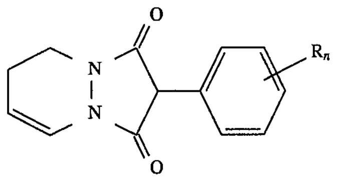

| Comp. No. | | $R_n$ | | Phys. data (°C.) |
|---|---|---|---|---|
| 8.120 | | 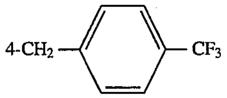 | | |
| 8.121 | | 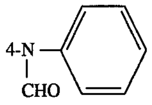 | | |
| 8.122 | 2-F | 4-Cl | 5-O$-CH_2-CH=CH_2$ | |
| 8.123 | 2-F | 4-Cl | 5-O$-CH_2-C\equiv CH$ | |

TABLE 9

Compounds of the formula

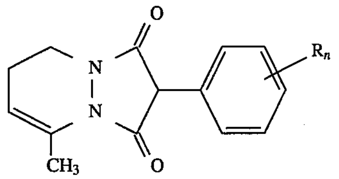

| Comp. No. | | $R_n$ | | Phys. data (°C.) |
|---|---|---|---|---|
| 9.001 | | H | | |
| 9.002 | | 2-$CH_3$ | | |
| 9.003 | | 4-$CH_3$ | | |
| 9.004 | | 2-$CH_3$ | 4-$CH_3$ | |
| 9.005 | | 2-$CH_3$ | 6-$CH_3$ | |
| 9.006 | | 2-$CH_3$ | 5-$CH_3$ | |
| 9.007 | | 3-$CH_3$ | 5-$CH_3$ | |
| 9.008 | | 2-$CH_3$ | 3-$CH_3$ | |
| 9.009 | | 3-$CH_3$ | 4-$CH_3$ | |
| 9.010 | 2-$CH_3$ | 4-$CH_3$ | 6-$CH_3$ | |
| 9.011 | 2-$CH_3$ | 4-$CH_3$ | 5-$CH_3$ | |
| 9.012 | | 2-Cl | | |
| 9.013 | | 4-Cl | | |
| 9.014 | | 2-Cl | 4-Cl | |
| 9.015 | | 2-Cl | 6-Cl | |
| 9.016 | | 2-Cl | 6-F | |
| 9.017 | | 2-$CH_3$ | 4-Cl | |
| 9.018 | | 2-$CH_3$ | 4-F | |
| 9.019 | | 2-Cl | 4-$CH_3$ | |
| 9.020 | | 2-Cl | 6-$CH_3$ | |
| 9.021 | | 2-F | 4-F | |
| 9.022 | | 2-F | 6-F | |
| 9.023 | | 2-$CH_3$ | 4-O$-CH_3$ | |
| 9.024 | | 2-$CH_3$ | 6-O$-CH_3$ | |
| 9.025 | | 2-Cl | 4-O$-CH_3$ | |
| 9.026 | | 2-Cl | 6-O$-CH_3$ | |
| 9.027 | | 3-$OCH_3$ | 4-$OCH_3$ | |
| 9.028 | | 2-$OCH_3$ | 5-$OCH_3$ | |
| 9.029 | | 2-$OCH_3$ | 4-$OCH_3$ | |
| 9.030 | | 2-$OCH_3$ | 6-$OCH_3$ | |
| 9.031 | | 2-$CF_3$ | 6-$CF_3$ | |
| 9.032 | | 2-$CF_3$ | 4-$CF_3$ | |

TABLE 9-continued

Compounds of the formula

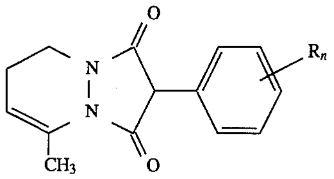

| Comp. No. | $R_n$ | | | Phys. data (°C.) |
|---|---|---|---|---|
| 9.033 | | $3\text{-}CF_3$ | $5\text{-}CF_3$ | |
| 9.034 | | 2-Cl | $4\text{-}CF_3$ | |
| 9.035 | | 2-Cl | $6\text{-}CF_3$ | |
| 9.036 | | $2\text{-}NO_2$ | $4\text{-}NO_2$ | |
| 9.037 | | 2-Cl | $4\text{-}NO_2$ | |
| 9.038 | | $2\text{-}CH_3$ | $4\text{-}NO_2$ | |
| 9.039 | | $2\text{-}O-CH_3$ | $4\text{-}NO_2$ | |
| 9.040 | | 2-F | $6\text{-}NO_2$ | |
| 9.041 | | 2-Cl | $6\text{-}NO_2$ | |
| 9.042 | | $2\text{-}CH_3$ | $6\text{-}NO_2$ | |
| 9.043 | | $2\text{-}O-CH_3$ | $6\text{-}NO_2$ | |
| 9.044 | | 2-F | $4\text{-}NO_2$ | |
| 9.045 | | $2\text{-}CH_3$ | $4\text{-}N(C_2H_5)_2$ | |
| 9.046 | | 2-Cl | $4\text{-}SO_2-CH_3$ | |
| 9.047 | | 2-Cl | $4\text{-}SO-CH_3$ | |
| 9.048 | | 2-Cl | $4\text{-}S-CH_3$ | |
| 9.049 | | 2-Cl | $6\text{-}SO_2-CH_3$ | |
| 9.050 | | 2-Cl | $6\text{-}SO-CH_3$ | |
| 9.051 | | 2-Cl | $6\text{-}S-CH_3$ | |
| 9.052 | | $2\text{-}CH_3$ | $4\text{-}SO_2-CH_3$ | |
| 9.053 | | $2\text{-}CH_3$ | $4\text{-}SO-CH_3$ | |
| 9.054 | | $2\text{-}CH_3$ | $4\text{-}S-CH_3$ | |
| 9.055 | | $2\text{-}CH_3$ | $6\text{-}SO_2-CH_3$ | |
| 9.056 | | $2\text{-}CH_3$ | $6\text{-}SO-CH_3$ | |
| 9.057 | | $2\text{-}CH_3$ | $6\text{-}S-CH_3$ | |
| 9.058 | | $2\text{-}O-CH_3$ | $6\text{-}SO_2-CH_3$ | |
| 9.059 | | $2\text{-}O-CH_3$ | $6\text{-}SO-CH_3$ | |
| 9.060 | | $2\text{-}O-CH_3$ | $6\text{-}S-CH_3$ | |
| 9.061 | | $2\text{-}O-CH_3$ | $4\text{-}SO_2-CH_3$ | |
| 9.062 | | $2\text{-}O-CH_3$ | $4\text{-}SO-CH_3$ | |
| 9.063 | | $2\text{-}O-CH_3$ | $4\text{-}S-CH_3$ | |
| 9.064 | | $2\text{-}CH_3$ | $6\text{-}N(C_2H_5)_2$ | |
| 9.065 | | 2-Cl | $6\text{-}N(CH_3)_2$ | |
| 9.066 | | 2-Cl | $4\text{-}N(CH_3)_2$ | |
| 9.067 | | 2-Cl | $4\text{-}CO_2CH_3$ | |
| 9.068 | | $2\text{-}CH_3$ | $6\text{-}CO_2C_2H_5$ | |
| 9.069 | | $2\text{-}CH_3$ | $4\text{-}CO_2C_2H_5$ | |
| 9.070 | | $2\text{-}CH_3$ | 4-CN | |
| 9.071 | | $2\text{-}CH_3$ | 6-CN | |
| 9.072 | | 2-Cl | 4-CN | |
| 9.073 | | 2-Cl | 6-CN | |
| 9.074 | | 2-Cl | $4\text{-}CO-CH_3$ | |
| 9.075 | | $2\text{-}O-CHF_2$ | $4\text{-}O-CHF_2$ | |
| 9.076 | | $2\text{-}CH_3$ | $4\text{-}O-CHF_2$ | |
| 9.077 | | 2-Cl | $4\text{-}O-CF_3$ | |
| 9.078 | | $2\text{-}O-CF_3$ | $4\text{-}O-CH_3$ | |
| 9.079 | | $2\text{-}O-CHF_2$ | 4-Cl | |
| 9.080 | | $2\text{-}O-CHF_2$ | $6\text{-}CH_3$ | |
| 9.081 | | $2\text{-}O-CHF_2$ | 6-Cl | |
| 9.082 | $2\text{-}O-CHF_2$ | $4\text{-}CH_3$ | $6\text{-}CH_3$ | |
| 9.083 | $2\text{-}CH_3$ | $4\text{-t-}C_4H_9$ | $6\text{-}CH_3$ | |
| 9.084 | $2\text{-i-}C_3H_7$ | $4\text{-i-}C_3H_7$ | $6\text{-i-}C_3H_7$ | |
| 9.085 | $2\text{-}CH_3$ | $4\text{-}O-CH_3$ | $6\text{-}CH_3$ | |
| 9.086 | 2-Cl | $4\text{-}CF_3$ | 6-Cl | |
| 9.087 | 2-Cl | $4\text{-}CF_3$ | 6-F | |
| 9.098 | 2-Cl | $4\text{-}NO_2$ | 6-Cl | |
| 9.089 | 2-Cl | 4-Cl | 6-Cl | |
| 9.090 | 2-F | 4-F | 6-F | |
| 9.091 | $2\text{-}CH_3$ | 4-NO | $6\text{-}CH_3$ | |
| 9.092 | 2-Cl | 4-Cl | $6\text{-}CH_3$ | |
| 9.093 | 2-Cl | $4\text{-}O-CH_3$ | 6-Cl | |
| 9.094 | 2-Cl | 4-Cl | $6\text{-}O-CH_3$ | |
| 9.095 | 2-F | $4\text{-}O-CH_3$ | 6-F | |
| 9.096 | $2\text{-}O-CH_3$ | $4\text{-}CH_3$ | $6\text{-}O-CH_3$ | |
| 9.097 | $2\text{-}O-CH_3$ | $4\text{-}O-CH_3$ | $6\text{-}CH_3$ | |

TABLE 9-continued
Compounds of the formula
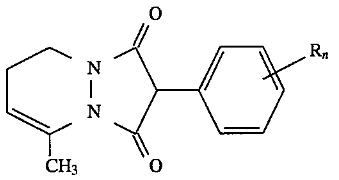
| Comp. No. | | $R_n$ | | Phys. data (°C.) |
|---|---|---|---|---|
| 9.098 | 2-$O-CH_3$ | 4-$O-CH_3$ | 6-$O-CH_3$ | |
| 9.099 | 2-$O-CH_3$ | 4-$CO-O-CH_3$ | 6-$O-CH_3$ | |
| 9.100 | 2-$CH_3$ | 4-Cl | 6-$CH_3$ | |
| 9.101 | 2-$CH_3$ | 4-F | 6-$CH_3$ | |
| 9.102 | 2-$CH_3$ | 4-$CH_3$ | 6-$O-CH_3$ | |
| 9.103 | 2-F | 4-Cl | 5-O-i-$C_3H_7$ | |
| 9.104 | 2-Cl | 4-Cl | 5-$O-CH_3$ | |
| 9.105 | | 4-Cl | 5-$O-CH_3$ | |
| 9.106 | 2-F | 4-Cl | 5-$CO-O-CH_3$ | |
| 9.107 | 2-F | 4-Cl | 5-$CO-O-C_2H_5$ | |
| 9.108 | | 4-Cl | 5-$CO-O-CH_3$ | |
| 9.109 | 2-Cl | 4-Cl | 5-$CO-O$-i-$C_3H_7$ | |
| 9.110 | | 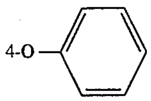 | | |
| 9.111 | | 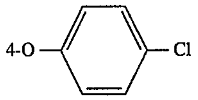 | | |
| 9.112 | | 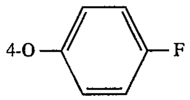 | | |
| 9.113 | | 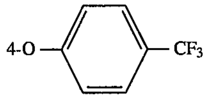 | | |
| 9.114 | 2-$CH_3$ | 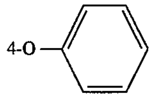 | | |
| 9.115 | | 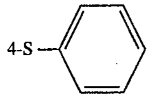 | | |
| 9.116 | | 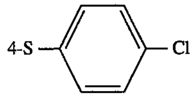 | | |
| 9.117 | | 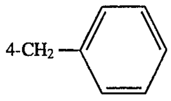 | | |
| 9.118 | | 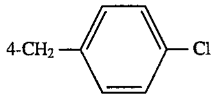 | | |
| 9.119 | | 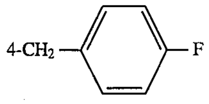 | | |

TABLE 9-continued

Compounds of the formula

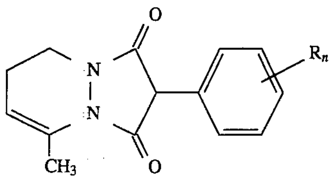

| Comp. No. | | $R_n$ | | Phys. data (°C.) |
|---|---|---|---|---|
| 9.120 | | 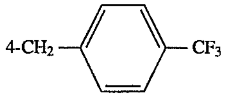 | | |
| 9.121 | | 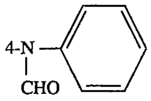 | | |
| 9.122 | 2-F | 4-Cl | $5\text{-}O-CH_2-CH=CH_2$ | |
| 9.123 | 2-F | 4-Cl | $5\text{-}O-CH_2-C\equiv CH$ | |

TABLE 10

Compounds of the formula

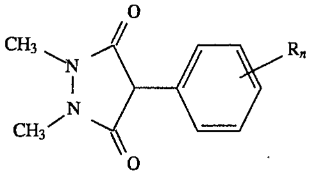

| Comp. No. | | $R_n$ | | Phys. data (°C.) |
|---|---|---|---|---|
| 10.001 | | H | | |
| 10.002 | | $2\text{-}CH_3$ | | |
| 10.003 | | $4\text{-}CH_3$ | | |
| 10.004 | | $2\text{-}CH_3$ | $4\text{-}CH_3$ | |
| 10.005 | | $2\text{-}CH_3$ | $6\text{-}CH_3$ | |
| 10.006 | | $2\text{-}CH_3$ | $5\text{-}CH_3$ | |
| 10.007 | | $3\text{-}CH_3$ | $5\text{-}CH_3$ | |
| 10.008 | | $2\text{-}CH_3$ | $3\text{-}CH_3$ | |
| 10.009 | | $3\text{-}CH_3$ | $4\text{-}CH_3$ | |
| 10.010 | $2\text{-}CH_3$ | $4\text{-}CH_3$ | $6\text{-}CH_3$ | m.p. 205–207 |
| 10.011 | $2\text{-}CH_3$ | $4\text{-}CH_3$ | $5\text{-}CH_3$ | |
| 10.012 | | 2-Cl | | |
| 10.013 | | 4-Cl | | |
| 10.014 | | 2-Cl | 4-Cl | |
| 10.015 | | 2-Cl | 6-Cl | |
| 10.016 | | 2-Cl | 6-F | |
| 10.017 | | $2\text{-}CH_3$ | 4-Cl | |
| 10.018 | | $2\text{-}CH_3$ | 4-F | |
| 10.019 | | 2-Cl | $4\text{-}CH_3$ | |
| 10.020 | | 2-Cl | $6\text{-}CH_3$ | |
| 10.021 | | 2-F | 4-F | |
| 10.022 | | 2-F | 6-F | |
| 10.023 | | $2\text{-}CH_3$ | $4\text{-}O-CH_3$ | |
| 10.024 | | $2\text{-}CH_3$ | $6\text{-}O-CH_3$ | |
| 10.025 | | 2-Cl | $4\text{-}O-CH_3$ | |
| 10.026 | | 2-Cl | $6\text{-}O-CH_3$ | |
| 10.027 | | $3\text{-}OCH_3$ | $4\text{-}OCH_3$ | |
| 10.028 | | $2\text{-}OCH_3$ | $5\text{-}OCH_3$ | |
| 10.029 | | $2\text{-}OCH_3$ | $4\text{-}OCH_3$ | |
| 10.030 | | $2\text{-}OCH_3$ | $6\text{-}OCH_3$ | |
| 10.031 | | $2\text{-}CF_3$ | $6\text{-}CF_3$ | |
| 10.032 | | $2\text{-}CF_3$ | $4\text{-}CF_3$ | |

TABLE 10-continued

Compounds of the formula

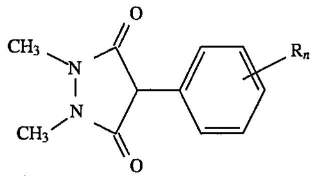

| Comp. No. | | $R_n$ | | Phys. data (°C.) |
|---|---|---|---|---|
| 10.033 | | 3-$CF_3$ | 5-$CF_3$ | |
| 10.034 | | 2-Cl | 4-$CF_3$ | |
| 10.035 | | 2-Cl | 6-$CF_3$ | |
| 10.036 | | 2-$NO_2$ | 4-$NO_2$ | |
| 10.037 | | 2-Cl | 4-$NO_2$ | |
| 10.038 | | 2-$CH_3$ | 4-$NO_2$ | |
| 10.039 | | 2-O—$CH_3$ | 4-$NO_2$ | |
| 10.040 | | 2-F | 6-$NO_2$ | |
| 10.041 | | 2-Cl | 6-$NO_2$ | |
| 10.042 | | 2-$CH_3$ | 6-$NO_2$ | |
| 10.043 | | 2-O—$CH_3$ | 6-$NO_2$ | |
| 10.044 | | 2-F | 4-$NO_2$ | |
| 10.045 | | 2-$CH_3$ | 4-$N(C_2H_5)_2$ | |
| 10.046 | | 2-Cl | 4-$SO_2$—$CH_3$ | |
| 10.047 | | 2-Cl | 4-SO—$CH_3$ | |
| 10.048 | | 2-Cl | 4-S—$CH_3$ | |
| 10.049 | | 2-Cl | 6-$SO_2$—$CH_3$ | |
| 10.050 | | 2-Cl | 6-SO—$CH_3$ | |
| 10.051 | | 2-Cl | 6-S—$CH_3$ | |
| 10.052 | | 2-$CH_3$ | 4-$SO_2$—$CH_3$ | |
| 10.053 | | 2-$CH_3$ | 4-SO—$CH_3$ | |
| 10.054 | | 2-$CH_3$ | 4-S—$CH_3$ | |
| 10.055 | | 2-$CH_3$ | 6-$SO_2$—$CH_3$ | |
| 10.056 | | 2-$CH_3$ | 6-SO—$CH_3$ | |
| 10.057 | | 2-$CH_3$ | 6-S—$CH_3$ | |
| 10.058 | | 2-O—$CH_3$ | 6-$SO_2$—$CH_3$ | |
| 10.059 | | 2-O—$CH_3$ | 6-SO—$CH_3$ | |
| 10.060 | | 2-O—$CH_3$ | 6-S—$CH_3$ | |
| 10.061 | | 2-O—$CH_3$ | 4-$SO_2$—$CH_3$ | |
| 10.062 | | 2-O—$CH_3$ | 4-SO—$CH_3$ | |
| 10.063 | | 2-O—$CH_3$ | 4-S—$CH_3$ | |
| 10.064 | | 2-$CH_3$ | 6-$N(C_2H_5)_2$ | |
| 10.065 | | 2-Cl | 6-$N(CH_3)_2$ | |
| 10.066 | | 2-Cl | 4-$N(CH_3)_2$ | |
| 10.067 | | 2-Cl | 4-$CO_2CH_3$ | |
| 10.068 | | 2-$CH_3$ | 6-$CO_2C_2H_5$ | |
| 10.069 | | 2-$CH_3$ | 4-$CO_2C_2H_5$ | |
| 10.070 | | 2-$CH_3$ | 4-CN | |
| 10.071 | | 2-$CH_3$ | 6-CN | |
| 10.072 | | 2-Cl | 4-CN | |
| 10.073 | | 2-Cl | 6-CN | |
| 10.074 | | 2-Cl | 4-CO—$CH_3$ | |
| 10.075 | | 2-O—$CHF_2$ | 4-O—$CHF_2$ | |
| 10.076 | | 2-$CH_3$ | 4-O—$CHF_2$ | |
| 10.077 | | 2-Cl | 4-O—$CF_3$ | |
| 10.078 | | 2-O—$CF_3$ | 4-O—$CH_3$ | |
| 10.079 | | 2-O—$CHF_2$ | 4-Cl | |
| 10.080 | | 2-O—$CHF_2$ | 6-$CH_3$ | |
| 10.081 | | 2-O—$CHF_2$ | 6-Cl | |
| 10.082 | 2-O—$CHF_2$ | 4-$CH_3$ | 6-$CH_3$ | |
| 10.083 | 2-$CH_3$ | 4-t-$C_4H_9$ | 6-$CH_3$ | |
| 10.084 | 2-i-$C_3H_7$ | 4-i-$C_3H_7$ | 6-i-$C_3H_7$ | |
| 10.085 | 2-$CH_3$ | 4-O—$CH_3$ | 6-$CH_3$ | |
| 10.086 | 2-Cl | 4-$CF_3$ | 6-Cl | |
| 10.087 | 2-Cl | 4-$CF_3$ | 6-F | |
| 10.088 | 2-Cl | 4-$NO_2$ | 6-Cl | |
| 10.089 | 2-Cl | 4-Cl | 6-Cl | |
| 10.090 | 2-F | 4-F | 6-F | |
| 10.091 | 2-$CH_3$ | 4-$NO_2$ | 6-$CH_3$ | |
| 10.092 | 2-Cl | 4-Cl | 6-$CH_3$ | |
| 10.093 | 2-Cl | 4-O—$CH_3$ | 6-Cl | |
| 10.094 | 2-Cl | 4-Cl | 6-O—$CH_3$ | |
| 10.095 | 2-F | 4-O—$CH_3$ | 6-F | |
| 10.096 | 2-O—$CH_3$ | 4-$CH_3$ | 6-O—$CH_3$ | |
| 10.097 | 2-O—$CH_3$ | 4-O—$CH_3$ | 6-$CH_3$ | |

TABLE 10-continued
Compounds of the formula
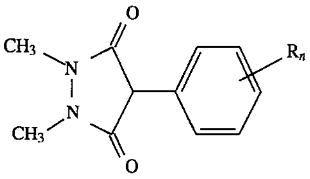
| Comp. No. | $R_n$ | | | Phys. data (°C.) |
|---|---|---|---|---|
| 10.098 | 2-O—$CH_3$ | 4-O—$CH_3$ | 6-O—$CH_3$ | |
| 10.099 | 2-O—$CH_3$ | 4-CO—O—$CH_3$ | 6-O—$CH_3$ | |
| 10.100 | 2-$CH_3$ | 4-Cl | 6-$CH_3$ | |
| 10.101 | 2-$CH_3$ | 4-F | 6-$CH_3$ | |
| 10.102 | 2-$CH_3$ | 4-$CH_3$ | 6-O—$CH_3$ | |
| 10.103 | 2-F | 4-Cl | 5-O-i-$C_3H_7$ | |
| 10.104 | 2-Cl | 4-Cl | 5-O—$CH_3$ | |
| 10.105 | | 4-Cl | 5-O—$CH_3$ | |
| 10.106 | 2-F | 4-Cl | 5-CO—O—$CH_3$ | |
| 10.107 | 2-F | 4-Cl | 5-CO—O—$C_2H_5$ | |
| 10.108 | | 4-Cl | 5-CO—O—$CH_3$ | |
| 10.109 | 2-Cl | 4-Cl | 5-CO—O-i-$C_3H_7$ | |
| 10.110 | | 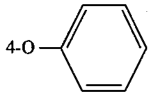 | | |
| 10.111 | | 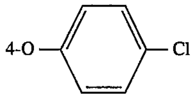 | | |
| 10.112 | | 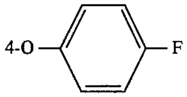 | | |
| 10.113 | | 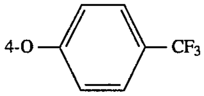 | | |
| 10.114 | 2-$CH_3$ | 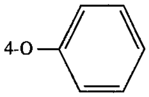 | | |
| 10.115 | | 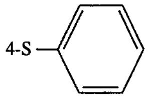 | | |
| 10.116 | | 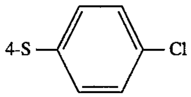 | | |
| 10.117 | | 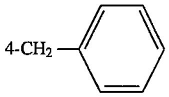 | | |
| 10.118 | | 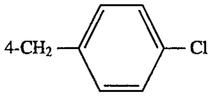 | | |
| 10.119 | | 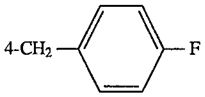 | | |

TABLE 10-continued

Compounds of the formula

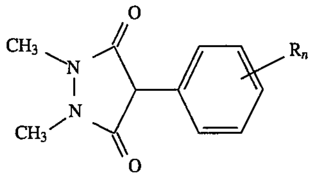

| Comp. No. | | $R_n$ | | Phys. data (°C.) |
|---|---|---|---|---|
| 10.120 | | 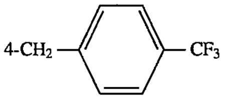 | | |
| 10.121 | | 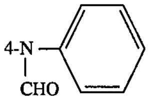 | | |
| 10.122 | 2-F | 4-Cl | $5\text{-}O-CH_2-CH=CH_2$ | |
| 10.123 | 2-F | 4-Cl | $5\text{-}O-CH_2-C\equiv CH$ | |
| 10.124 | 2-Br | | | |
| 10.125 | $2\text{-}CF_3$ | | | |
| 10.126 | $2\text{-}OCH_3$ | | | |
| 10.127 | $2\text{-}CH_3$ | 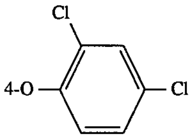 | | |
| 10.128 | $2\text{-}CH_3$ | 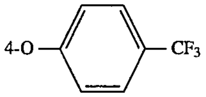 | | |
| 10.129 | $2\text{-}CH_3$ | 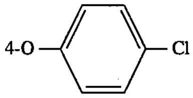 | | |
| 10.130 | $2\text{-}CH_3$ | 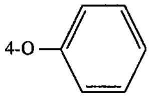 | $6\text{-}CH_3$ | |
| 10.131 | $2\text{-}CH_3$ | 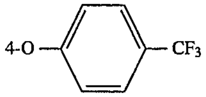 | $6\text{-}CH_3$ | |
| 10.132 | $2\text{-}CH_3$ | 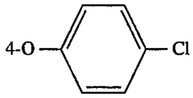 | $6\text{-}CH_3$ | |
| 10.133 | $2\text{-}CH_3$ | 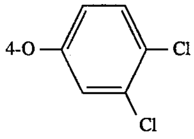 | $6\text{-}CH_3$ | |
| 10.134 | $2\text{-}CH_3$ | 4-Br | $6\text{-}CH_3$ | |
| 10.135 | $2\text{-}CH_3$ | $6\text{-}C_2H_5$ | | |
| 10.136 | $2\text{-}C_2H_5$ | $6\text{-}C_2H_5$ | | |
| 10.137 | $2\text{-}CH_3$ | $4\text{-}OC_2H_5$ | $6\text{-}CH_3$ | |
| 10.138 | $2\text{-}CH_3$ | $4\text{-}O\text{-}i\text{-}C_3H_7$ | $6\text{-}CH_3$ | |

TABLE 10-continued
Compounds of the formula
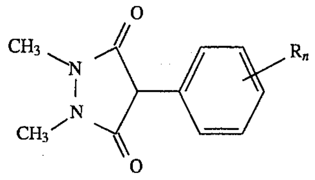
| Comp. No. | | $R_n$ | | Phys. data (°C.) |
|---|---|---|---|---|
| 10.139 | 2-$CH_3$ | 4-O-n-$C_3H_7$ | 6-$CH_3$ | |
| 10.140 | 2-$CH_3$ | 4-O-n-$C_{10}H_{21}$ | 6-$CH_3$ | |
| 10.141 | 2-$CH_3$ | 4-O-n-$C_3H_7$ | | |
| 10.142 | 2-$CH_3$ | 4-O-$(CH_2)_2OCH_3$ | | |
| 10.143 | 2-$CH_3$ | 4-O-$(CH_2)_2OCH_3$ | 6-$CH_3$ | |
| 10.144 | 2-$CH_3$ | 4-O-$(CH_2)_2OCH_3$ | | |
| 10.145 | 2-$CH_3$ | 4-O-n-$C_6H_{13}$ | 6-$CH_3$ | |
| 10.146 | 2-$CH_3$ | 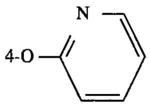 | | |
| 10.147 | 2-$CH_3$ | 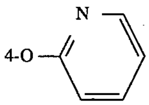 | 6-$CH_3$ | |
| 10.148 | 2-$CH_3$ | 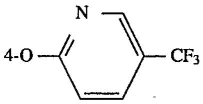 | | |
| 10.149 | 2-$CH_3$ | 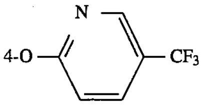 | 6-$CH_3$ | |
| 10.150 | 2-$CH_3$ | 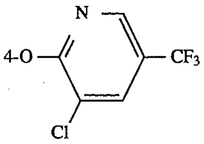 | | |
| 10.151 | 2-$CH_3$ | 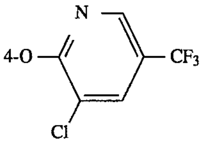 | 6-$CH_3$ | |
| 10.152 | 2-$CH_3$ | 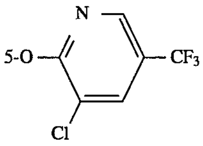 | | |
| 10.153 | 2-$CH_3$ | 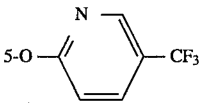 | | |
| 10.154 | 2-$CH_3$ | 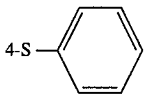 | 6-$CH_3$ | |

TABLE 10-continued

Compounds of the formula

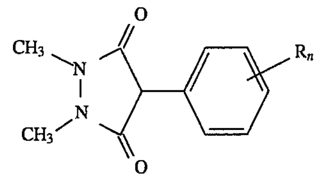

| Comp. No. | | $R_n$ | | Phys. data (°C.) |
|---|---|---|---|---|
| 10.155 | 2-$CH_3$ | 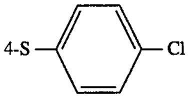 | 6-$CH_3$ | |
| 10.156 | 2-$C_2H_5$ | 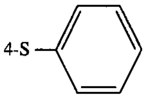 | 6-$CH_3$ | |

TABLE 11

Compounds of the formula

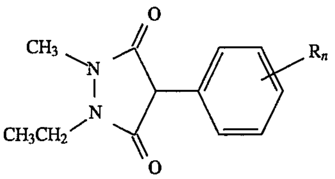

| Comp. No. | | $R_n$ | | Phys. data (°C.) |
|---|---|---|---|---|
| 11.001 | | H | | |
| 11.002 | | 2-$CH_3$ | | |
| 11.003 | | 4-$CH_3$ | | |
| 11.004 | | 2-$CH_3$ | 4-$CH_3$ | |
| 11.005 | | 2-$CH_3$ | 6-$CH_3$ | |
| 11.006 | | 2-$CH_3$ | 5-$CH_3$ | |
| 11.007 | | 3-$CH_3$ | 5-$CH_3$ | |
| 11.008 | | 2-$CH_3$ | 3-$CH_3$ | |
| 11.009 | | 3-$CH_3$ | 4-$CH_3$ | |
| 11.010 | 2-$CH_3$ | 4-$CH_3$ | 6-$CH_3$ | m.p. 195–196 |
| 11.011 | 2-$CH_3$ | 4-$CH_3$ | 5-$CH_3$ | |
| 11.012 | | 2-Cl | | |
| 11.013 | | 4-Cl | | |
| 11.014 | | 2-Cl | 4-Cl | |
| 11.015 | | 2-Cl | 6-Cl | |
| 11.016 | | 2-Cl | 6-F | |
| 11.017 | | 2-$CH_3$ | 4-Cl | |
| 11.018 | | 2-$CH_3$ | 4-F | |
| 11.019 | | 2-Cl | 4-$CH_3$ | |
| 11.020 | | 2-Cl | 6-$CH_3$ | |
| 11.021 | | 2-F | 4-F | |
| 11.022 | | 2-F | 6-F | |
| 11.023 | | 2-$CH_3$ | 4-O$-CH_3$ | |
| 11.024 | | 2-$CH_3$ | 6-O$-CH_3$ | |
| 11.025 | | 2-Cl | 4-O$-CH_3$ | |
| 11.026 | | 2-Cl | 6-O$-CH_3$ | |
| 11.027 | | 3-$OCH_3$ | 4-$OCH_3$ | |
| 11.028 | | 2-$OCH_3$ | 5-$OCH_3$ | |
| 11.029 | | 2-$OCH_3$ | 4-$OCH_3$ | |
| 11.030 | | 2-$OCH_3$ | 6-$OCH_3$ | |
| 11.031 | | 2-$CF_3$ | 6-$CF_3$ | |
| 11.032 | | 2-$CF_3$ | 4-$CF_3$ | |
| 11.033 | | 3-$CF_3$ | 5-$CF_3$ | |
| 11.034 | | 2-Cl | 4-$CF_3$ | |
| 11.035 | | 2-Cl | 6-$CF_3$ | |
| 11.036 | | 2-$NO_2$ | 4-$NO_2$ | |
| 11.037 | | 2-Cl | 4-$NO_2$ | |

TABLE 11-continued

Compounds of the formula

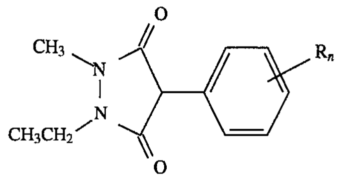

| Comp. No. | | $R_n$ | | Phys. data (°C.) |
|---|---|---|---|---|
| 11.038 | | 2-$CH_3$ | 4-$NO_2$ | |
| 11.039 | | 2-O−$CH_3$ | 4-$NO_2$ | |
| 11.040 | | 2-F | 6-$NO_2$ | |
| 11.041 | | 2-Cl | 6-$NO_2$ | |
| 11.042 | | 2-$CH_3$ | 6-$NO_2$ | |
| 11.043 | | 2-O−$CH_3$ | 6-$NO_2$ | |
| 11.044 | | 2-F | 4-$NO_2$ | |
| 11.045 | | 2-$CH_3$ | 4-$N(C_2H_5)_2$ | |
| 11.046 | | 2-Cl | 4-$SO_2$−$CH_3$ | |
| 11.047 | | 2-Cl | 4-SO−$CH_3$ | |
| 11.048 | | 2-Cl | 4-S−$CH_3$ | |
| 11.049 | | 2-Cl | 6-$SO_2$−$CH_3$ | |
| 11.050 | | 2-Cl | 6-SO−$CH_3$ | |
| 11.051 | | 2-Cl | 6-S−$CH_3$ | |
| 11.052 | | 2-$CH_3$ | 4-$SO_2$−$CH_3$ | |
| 11.053 | | 2-$CH_3$ | 4-SO−$CH_3$ | |
| 11.054 | | 2-$CH_3$ | 4-S−$CH_3$ | |
| 11.055 | | 2-$CH_3$ | 6-$SO_2$−$CH_3$ | |
| 11.056 | | 2-$CH_3$ | 6-SO−$CH_3$ | |
| 11.057 | | 2-$CH_3$ | 6-S−$CH_3$ | |
| 11.058 | | 2-O−$CH_3$ | 6-$SO_2$−$CH_3$ | |
| 11.059 | | 2-O−$CH_3$ | 6-SO−$CH_3$ | |
| 11.060 | | 2-O−$CH_3$ | 6-S−$CH_3$ | |
| 11.061 | | 2-O−$CH_3$ | 4-$SO_2$−$CH_3$ | |
| 11.062 | | 2-O−$CH_3$ | 4-SO−$CH_3$ | |
| 11.063 | | 2-O−$CH_3$ | 4-S−$CH_3$ | |
| 11.064 | | 2-$CH_3$ | 6-$N(C_2H_5)_2$ | |
| 11.065 | | 2-Cl | 6-$N(CH_3)_2$ | |
| 11.066 | | 2-Cl | 4-$N(CH_3)_2$ | |
| 11.067 | | 2-Cl | 4-$CO_2CH_3$ | |
| 11.068 | | 2-$CH_3$ | 6-$CO_2C_2H_5$ | |
| 11.069 | | 2-$CH_3$ | 4-$CO_2C_2H_5$ | |
| 11.070 | | 2-$CH_3$ | 4-CN | |
| 11.071 | | 2-$CH_3$ | 6-CN | |
| 11.072 | | 2-Cl | 4-CN | |
| 11.073 | | 2-Cl | 6-CN | |
| 11.074 | | 2-Cl | 4-CO−$CH_3$ | |
| 11.075 | | 2-O−$CHF_2$ | 4-O−$CHF_2$ | |
| 11.076 | | 2-$CH_3$ | 4-O−$CHF_2$ | |
| 11.077 | | 2-Cl | 4-O−$CF_3$ | |
| 11.078 | | 2-O−$CF_3$ | 4-O−$CH_3$ | |
| 11.079 | | 2-O−$CHF_2$ | 4-Cl | |
| 11.080 | | 2-O−$CHF_2$ | 6-$CH_3$ | |
| 11.081 | | 2-O−$CHF_2$ | 6-Cl | |
| 11.082 | 2-O−$CHF_2$ | 4-$CH_3$ | 6-$CH_3$ | |
| 11.083 | 2-$CH_3$ | 4-t-$C_4H_9$ | 6-$CH_3$ | |
| 11.084 | 2-i-$C_3H_7$ | 4-i-$C_3H_7$ | 6-i-$C_3H_7$ | |
| 11.085 | 2-$CH_3$ | 4-O−$CH_3$ | 6-$CH_3$ | |
| 11.086 | 2-Cl | 4-$CF_3$ | 6-Cl | |
| 11.087 | 2-Cl | 4-$CF_3$ | 6-F | |
| 11.088 | 2-Cl | 4-$NO_2$ | 6-Cl | |
| 11.089 | 2-Cl | 4-Cl | 6-Cl | |
| 11.090 | 2-F | 4-F | 6-F | |
| 11.091 | 2-$CH_3$ | 4-$NO_2$ | 6-$CH_3$ | |
| 11.092 | 2-Cl | 4-Cl | 6-$CH_3$ | |
| 11.093 | 2-Cl | 4-O−$CH_3$ | 6-Cl | |
| 11.094 | 2-Cl | 4-Cl | 6-O−$CH_3$ | |
| 11.095 | 2-F | 4-O−$CH_3$ | 6-F | |
| 11.096 | 2-O−$CH_3$ | 4-$CH_3$ | 6-O−$CH_3$ | |
| 11.097 | 2-O−$CH_3$ | 4-O−$CH_3$ | 6-$CH_3$ | |
| 11.098 | 2-O−$CH_3$ | 4-O−$CH_3$ | 6-O−$CH_3$ | |
| 11.099 | 2-O−$CH_3$ | 4-CO−O−$CH_3$ | 6-O−$CH_3$ | |
| 11.100 | 2-$CH_3$ | 4-Cl | 6-$CH_3$ | |
| 11.101 | 2-$CH_3$ | 4-F | 6-$CH_3$ | |
| 11.102 | 2-$CH_3$ | 4-$CH_3$ | 6-O−$CH_3$ | |

TABLE 11-continued
Compounds of the formula
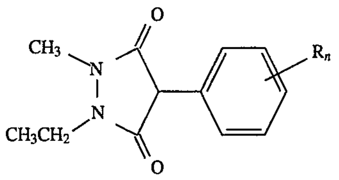
| Comp. No. | | $R_n$ | | Phys. data (°C.) |
|---|---|---|---|---|
| 11.103 | 2-F | 4-Cl | 5-O-i-$C_3H_7$ | |
| 11.104 | 2-Cl | 4-Cl | 5-O—$CH_3$ | |
| 11.105 | | 4-Cl | 5-O—$CH_3$ | |
| 11.106 | 2-F | 4-Cl | 5-CO—O—$CH_3$ | |
| 11.107 | 2-F | 4-Cl | 5-CO—O—$C_2H_5$ | |
| 11.108 | | 4-Cl | 5-CO—O—$CH_3$ | |
| 11.109 | 2-Cl | 4-Cl | 5-CO—O-i-$C_3H_7$ | |
| 11.110 | | 4-O 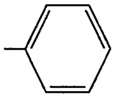 | | |
| 11.111 | | 4-O 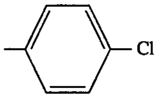 | | |
| 11.112 | | 4-O 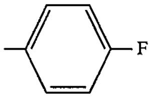 | | |
| 11.113 | | 4-O 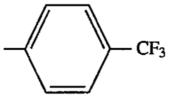 | | |
| 11.114 | 2-$CH_3$ | 4-O 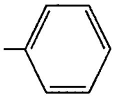 | | |
| 11.115 | | 4-S 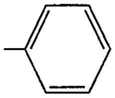 | | |
| 11.116 | | 4-S 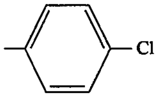 | | |
| 11.117 | | 4-$CH_2$ 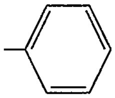 | | |
| 11.118 | | 4-$CH_2$ 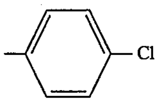 | | |
| 11.119 | | 4-$CH_2$ 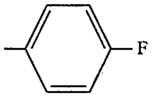 | | |
| 11.120 | | 4-$CH_2$ 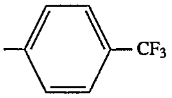 | | |

TABLE 11-continued
Compounds of the formula
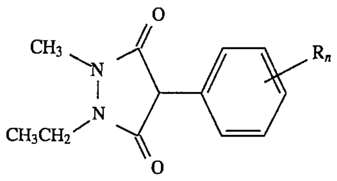
| Comp. No. | $R_n$ | | | Phys. data (°C.) |
|---|---|---|---|---|
| 11.121 | | 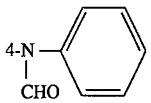 | | |
| 11.122 | 2-F | 4-Cl | 5-O$-CH_2-CH=CH_2$ | |
| 11.123 | 2-F | 4-Cl | 5-O$-CH_2-C\equiv CH$ | |
| 11.124 | 2-Br | | | |
| 11.125 | 2-$CF_3$ | | | |
| 11.126 | 2-$OCH_3$ | | | |
| 11.127 | 2-$CH_3$ | 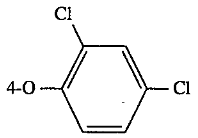 | | |
| 11.128 | 2-$CH_3$ | 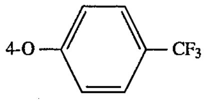 | | |
| 11.129 | 2-$CH_3$ | 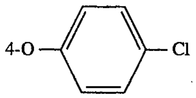 | | |
| 11.130 | 2-$CH_3$ | 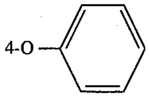 | 6-$CH_3$ | |
| 11.131 | 2-$CH_3$ | 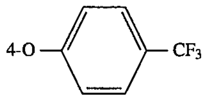 | 6-$CH_3$ | |
| 11.132 | 2-$CH_3$ | 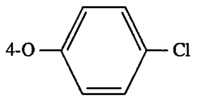 | 6-$CH_3$ | |
| 11.133 | 2-$CH_3$ | 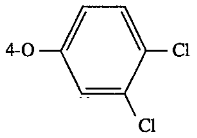 | 6-$CH_3$ | |
| 11.134 | 2-$CH_3$ | 4-Br | 6-$CH_3$ | |
| 11.135 | 2-$CH_3$ | 6-$C_2H_5$ | | |
| 11.136 | 2-$C_2H_5$ | 6-$C_2H_5$ | | |
| 11.137 | 2-$CH_3$ | 4-$OC_2H_5$ | 6-$CH_3$ | |
| 11.138 | 2-$CH_3$ | 4-O-i-$C_3H_7$ | 6-$CH_3$ | |
| 11.139 | 2-$CH_3$ | 4-O-n-$C_3H_7$ | 6-$CH_3$ | |
| 11.140 | 2-$CH_3$ | 4-O-n-$C_{10}H_{21}$ | 6-$CH_3$ | |
| 11.141 | 2-$CH_3$ | 4-O-n-$C_3H_7$ | | |
| 11.142 | 2-$CH_3$ | 4-O$-(CH_2)_2OCH_3$ | | |
| 11.143 | 2-$CH_3$ | 4-O$-(CH_2)_2OCH_3$ | 6-$CH_3$ | |

TABLE 11-continued
Compounds of the formula
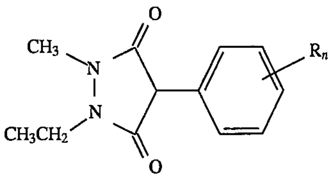
| Comp. No. | | $R_n$ | | Phys. data (°C.) |
|---|---|---|---|---|
| 11.144 | 2-$CH_3$ | 4-O—$(CH_2)_2OCH_3$ | | |
| 11.145 | 2-$CH_3$ | 4-O-n-$C_6H_{13}$ | 6-$CH_3$ | |
| 11.146 | 2-$CH_3$ | 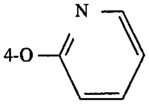 | | |
| 11.147 | 2-$CH_3$ | 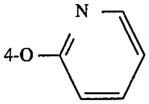 | 6-$CH_3$ | |
| 11.148 | 2-$CH_3$ | 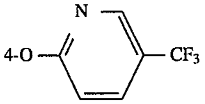 | | |
| 11.149 | 2-$CH_3$ | 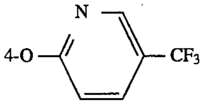 | 6-$CH_3$ | |
| 11.150 | 2-$CH_3$ | 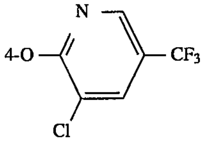 | | |
| 11.151 | 2-$CH_3$ | 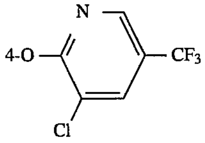 | 6-$CH_3$ | |
| 11.152 | 2-$CH_3$ | 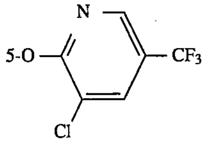 | | |
| 11.153 | 2-$CH_3$ | 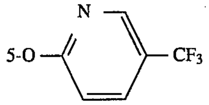 | | |
| 11.154 | 2-$CH_3$ | 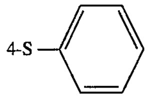 | 6-$CH_3$ | |
| 11.155 | 2-$CH_3$ | 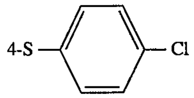 | 6-$CH_3$ | |

TABLE 11-continued

Compounds of the formula

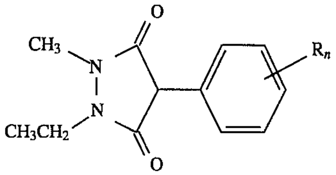

| Comp. No. | $R_n$ | | | Phys. data (°C.) |
|---|---|---|---|---|
| 11.156 | $2\text{-}C_2H_5$ | 4-S 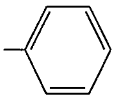 | $6\text{-}CH_3$ | |

TABLE 12

Compounds of the formula

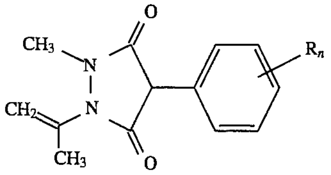

| Comp. No. | $R_n$ | | | Phys. data (°C.) |
|---|---|---|---|---|
| 12.001 | | H | | |
| 12.002 | | $2\text{-}CH_3$ | | |
| 12.003 | | $4\text{-}CH_3$ | | |
| 12.004 | | $2\text{-}CH_3$ | $4\text{-}CH_3$ | |
| 12.005 | | $2\text{-}CH_3$ | $6\text{-}CH_3$ | |
| 12.006 | | $2\text{-}CH_3$ | $5\text{-}CH_3$ | |
| 12.007 | | $3\text{-}CH_3$ | $5\text{-}CH_3$ | |
| 12.008 | | $2\text{-}CH_3$ | $3\text{-}CH_3$ | |
| 12.009 | | $3\text{-}CH_3$ | $4\text{-}CH_3$ | |
| 12.010 | $2\text{-}CH_3$ | $4\text{-}CH_3$ | $6\text{-}CH_3$ | |
| 12.011 | $2\text{-}CH_3$ | $4\text{-}CH_3$ | $5\text{-}CH_3$ | |
| 12.012 | | 2-Cl | | |
| 12.013 | | 4-Cl | | |
| 12.014 | | 2-Cl | 4-Cl | |
| 12.015 | | 2-Cl | 6-Cl | |
| 12.016 | | 2-Cl | 6-F | |
| 12.017 | | $2\text{-}CH_3$ | 4-Cl | |
| 12.018 | | $2\text{-}CH_3$ | 4-F | |
| 12.019 | | 2-Cl | $4\text{-}CH_3$ | |
| 12.020 | | 2-Cl | $6\text{-}CH_3$ | |
| 12.021 | | 2-F | 4-F | |
| 12.022 | | 2-F | 6-F | |
| 12.023 | | $2\text{-}CH_3$ | $4\text{-}O-CH_3$ | |
| 12.024 | | $2\text{-}CH_3$ | $6\text{-}O-CH_3$ | |
| 12.025 | | 2-Cl | $4\text{-}O-CH_3$ | |
| 12.026 | | 2-Cl | $6\text{-}O-CH_3$ | |
| 12.027 | | $3\text{-}OCH_3$ | $4\text{-}OCH_3$ | |
| 12.028 | | $2\text{-}OCH_3$ | $5\text{-}OCH_3$ | |
| 12.029 | | $2\text{-}OCH_3$ | $4\text{-}OCH_3$ | |
| 12.030 | | $2\text{-}OCH_3$ | $6\text{-}OCH_3$ | |
| 12.031 | | $2\text{-}CF_3$ | $6\text{-}CF_3$ | |
| 12.032 | | $2\text{-}CF_3$ | $4\text{-}CF_3$ | |
| 12.033 | | $3\text{-}CF_3$ | $5\text{-}CF_3$ | |
| 12.034 | | 2-Cl | $4\text{-}CF_3$ | |
| 12.035 | | 2-Cl | $6\text{-}CF_3$ | |
| 12.036 | | $2\text{-}NO_2$ | $4\text{-}NO_2$ | |
| 12.037 | | 2-Cl | $4\text{-}NO_2$ | |
| 12.038 | | $2\text{-}CH_3$ | $4\text{-}NO_2$ | |
| 12.039 | | $2\text{-}O-CH_3$ | $4\text{-}NO_2$ | |
| 12.040 | | 2-F | $6\text{-}NO_2$ | |
| 12.041 | | 2-Cl | $6\text{-}NO_2$ | |
| 12.042 | | $2\text{-}CH_3$ | $6\text{-}NO_2$ | |

TABLE 12-continued

Compounds of the formula

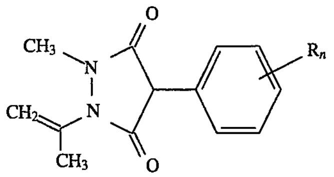

| Comp. No. | | $R_n$ | | Phys. data (°C.) |
|---|---|---|---|---|
| 12.043 | | 2-O$-$$CH_3$ | 6-$NO_2$ | |
| 12.044 | | 2-F | 4-$NO_2$ | |
| 12.045 | | 2-$CH_3$ | 4-$N(C_2H_5)_2$ | |
| 12.046 | | 2-Cl | 4-$SO_2$$-$$CH_3$ | |
| 12.047 | | 2-Cl | 4-SO$-$$CH_3$ | |
| 12.048 | | 2-Cl | 4-S$-$$CH_3$ | |
| 12.049 | | 2-Cl | 6-$SO_2$$-$$CH_3$ | |
| 12.050 | | 2-Cl | 6-SO$-$$CH_3$ | |
| 12.051 | | 2-Cl | 6-S$-$$CH_3$ | |
| 12.052 | | 2-$CH_3$ | 4-$SO_2$$-$$CH_3$ | |
| 12.053 | | 2-$CH_3$ | 4-SO$-$$CH_3$ | |
| 12.054 | | 2-$CH_3$ | 4-S$-$$CH_3$ | |
| 12.055 | | 2-$CH_3$ | 6-$SO_2$$-$$CH_3$ | |
| 12.056 | | 2-$CH_3$ | 6-SO$-$$CH_3$ | |
| 12.057 | | 2-$CH_3$ | 6-S$-$$CH_3$ | |
| 12.058 | | 2-O$-$$CH_3$ | 6-$SO_2$$-$$CH_3$ | |
| 12.059 | | 2-O$-$$CH_3$ | 6-SO$-$$CH_3$ | |
| 12.060 | | 2-O$-$$CH_3$ | 6-S$-$$CH_3$ | |
| 12.061 | | 2-O$-$$CH_3$ | 4-$SO_2$$-$$CH_3$ | |
| 12.062 | | 2-O$-$$CH_3$ | 4-SO$-$$CH_3$ | |
| 12.063 | | 2-O$-$$CH_3$ | 4-S$-$$CH_3$ | |
| 12.064 | | 2-$CH_3$ | 6-$N(C_2H_5)_2$ | |
| 12.065 | | 2-Cl | 6-$N(CH_3)_2$ | |
| 12.066 | | 2-Cl | 4-$N(CH_3)_2$ | |
| 12.067 | | 2-Cl | 4-$CO_2$$-$$CH_3$ | |
| 12.068 | | 2-$CH_3$ | 6-$CO_2C_2H_5$ | |
| 12.069 | | 2-$CH_3$ | 4-$CO_2C_2H_5$ | |
| 12.070 | | 2-$CH_3$ | 4-CN | |
| 12.071 | | 2-$CH_3$ | 6-CN | |
| 12.072 | | 2-Cl | 4-CN | |
| 12.073 | | 2-Cl | 6-CN | |
| 12.074 | | 2-Cl | 4-CO$-$$CH_3$ | |
| 12.075 | | 2-O$-$$CHF_2$ | 4-O$-$$CHF_2$ | |
| 12.076 | | 2-$CH_3$ | 4-O$-$$CHF_2$ | |
| 12.077 | | 2-Cl | 4-O$-$$CF_3$ | |
| 12.078 | | 2-O$-$$CF_3$ | 4-O$-$$CH_3$ | |
| 12.079 | | 2-O$-$$CHF_2$ | 4-Cl | |
| 12.080 | | 2-O$-$$CHF_2$ | 6-$CH_3$ | |
| 12.081 | | 2-O$-$$CHF_2$ | 6-Cl | |
| 12.082 | 2-O$-$$CHF_2$ | 4-$CH_3$ | 6-$CH_3$ | |
| 12.083 | 2-$CH_3$ | 4-t-$C_4H_9$ | 6-$CH_3$ | |
| 12.084 | 2-i-$C_3H_7$ | 4-i-$C_3H_7$ | 6-i-$C_3H_7$ | |
| 12.085 | 2-$CH_3$ | 4-O$-$$CH_3$ | 6-$CH_3$ | |
| 12.086 | 2-Cl | 4-$CF_3$ | 6-Cl | |
| 12.087 | 2-Cl | 4-$CF_3$ | 6-F | |
| 12.088 | 2-Cl | 4-$NO_2$ | 6-Cl | |
| 12.089 | 2-Cl | 4-Cl | 6-Cl | |
| 12.090 | 2-F | 4-F | 6-F | |
| 12.091 | 2-$CH_3$ | 4-NO | 6-$CH_3$ | |
| 12.092 | 2-Cl | 4-Cl | 6-$CH_3$ | |
| 12.093 | 2-Cl | 4-O$-$$CH_3$ | 6-Cl | |
| 12.094 | 2-Cl | 4-Cl | 6-O$-$$CH_3$ | |
| 12.095 | 2-F | 4-O$-$$CH_3$ | 6-F | |
| 12.096 | 2-O$-$$CH_3$ | 4-$CH_3$ | 6-O$-$$CH_3$ | |
| 12.097 | 2-O$-$$CH_3$ | 4-O$-$$CH_3$ | 6-$CH_3$ | |
| 12.098 | 2-O$-$$CH_3$ | 4-O$-$$CH_3$ | 6-O$-$$CH_3$ | |
| 12.099 | 2-O$-$$CH_3$ | 4-CO$-$O$-$$CH_3$ | 6-O$-$$CH_3$ | |
| 12.100 | 2-$CH_3$ | 4-Cl | 6-$CH_3$ | |
| 12.101 | 2-$CH_3$ | 4-F | 6-$CH_3$ | |
| 12.102 | 2-$CH_3$ | 4-$CH_3$ | 6-O$-$$CH_3$ | |
| 12.103 | 2-F | 4-Cl | 5-O-i-$C_3H_7$ | |
| 12.104 | 2-Cl | 4-Cl | 5-O$-$$CH_3$ | |
| 12.105 | | 4-Cl | 5-O$-$$CH_3$ | |
| 12.106 | 2-F | 4-Cl | 5-CO$-$O$-$$CH_3$ | |
| 12.107 | 2-F | 4-Cl | 5-CO$-$O$-$$C_2H_5$ | |

TABLE 12-continued
Compounds of the formula
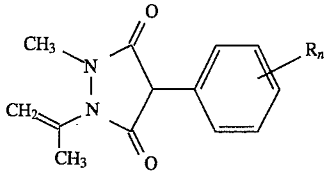
| Comp. No. | | $R_n$ | | Phys. data (°C.) |
|---|---|---|---|---|
| 12.108 | | 4-Cl | 5-CO—O—$CH_3$ | |
| 12.109 | 2-Cl | 4-Cl | 5-CO—O-i-$C_3H_7$ | |
| 12.110 | | 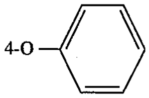 | | |
| 12.111 | | 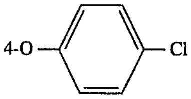 | | |
| 12.112 | | 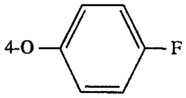 | | |
| 12.113 | | 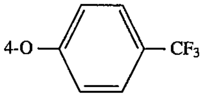 | | |
| 12.114 | 2-$CH_3$ | 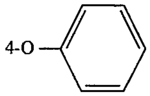 | | |
| 12.115 | | 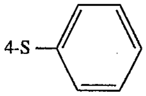 | | |
| 12.116 | | 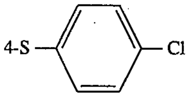 | | |
| 12.117 | | 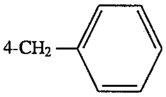 | | |
| 12.118 | | 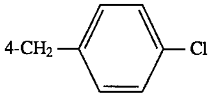 | | |
| 12.119 | | 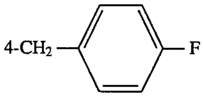 | | |
| 12.120 | | 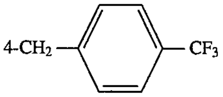 | | |
| 12.121 | | 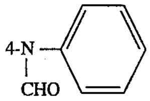 | | |

TABLE 12-continued

Compounds of the formula

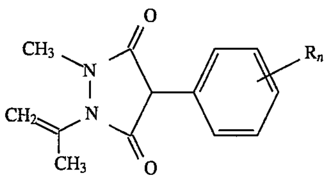

| Comp. No. | | $R_n$ | | Phys. data (°C.) |
|---|---|---|---|---|
| 12.122 | 2-F | 4-Cl | 5-O$-CH_2-CH=CH_2$ | |
| 12.123 | 2-F | 4-Cl | 5-O$-CH_2-C\equiv CH$ | |

TABLE 13

Compounds of the formula

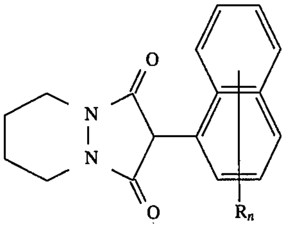

| Comp. No. | $R_n$ | Phys. data (°C.) |
|---|---|---|
| 13.001 | H | m.p. 171–172 |
| 13.002 | 2-$CH_3$ | |
| 13.003 | 2-$OCH_3$ | |
| 13.004 | 4-O | |
| 13.005 | 4-F | |
| 13.006 | 4-$NO_2$ | |
| 13.007 | 6-$NO_2$ | |
| 13.008 | 7-$NO_2$ | |

TABLE 14

Compounds of the formula

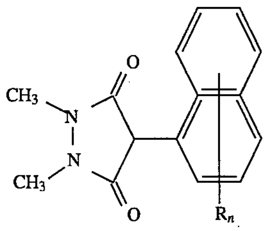

| Comp. No. | $R_n$ | Phys. data (°C.) |
|---|---|---|
| 14.001 | H | |
| 14.002 | 2-$CH_3$ | |
| 14.003 | 2-$OCH_3$ | |
| 14.004 | 4-Cl | |
| 14.005 | 4-F | |
| 14.006 | 4-$NO_2$ | |
| 14.007 | 6-$NO_2$ | |
| 14.008 | 7-$NO_2$ | |

FORMULATION EXAMPLES

Example F1: Formulation examples of active ingredients of the formula I (%=per cent by weight)

| a) Wettable powder | a) | b) | c) |
|---|---|---|---|
| Active ingredient No. 1.010 | 20% | 50% | 0,5% |
| Sodium ligninsulfonate | 5% | 5% | 4% |
| Sodium lauryl sulfate | 3% | —% | —% |
| Sodium diisobutylnaphthalene sulfonate | — | 6% | 6% |
| Octylphenol polyethylene glycol ether (7–8 mol of EO) | — | 2% | 2% |
| Highly-disperse silica | 5% | 27% | 27% |
| Kaolin | 67% | 10% | — |
| Sodium chloride | — | — | 59.5% |

The active ingredient is mixed thoroughly with the additives, and the mixture is ground thoroughly in a suitable mill. This gives wettable powders which can be diluted with water to give suspensions of any desired concentration.

| b) Emulsion concentrate | a) | b) |
|---|---|---|
| Active ingredient No. 1.010 | 10% | 1% |
| Octylphenol polyethylene glycol ether (4–5 mol of EO) | 3% | 3% |
| Calcium dodecylbenzene sulfonate | 3% | 3% |
| Castor oil polyglycol ether (36 mol EO) | 4% | 4% |
| Cyclohexanone | 30% | 10% |
| Xylene mixture | 50% | 79% |

Emulsions of any desired concentration can be prepared from this concentrate by dilution with water.

| c) Dusts | a) | b) |
|---|---|---|
| Active ingredient No. 1.010 | 0.1% | 1% |
| Talc | 99.9% | — |
| Kaolin | — | 99% |

Ready-for-use dusts are obtained by mixing the active ingredient with the carrier and grinding the mixture on a suitable mill.

| d) Extruder granules | a) | b) |
|---|---|---|
| Active ingredient No. 1.010 | 10% | 1% |
| Sodium ligninsulfonate | 2% | 2% |
| Carboxymethylcellulose | 1% | 1% |
| Kaolin | 87% | 96% |

The active ingredient is mixed with the additives, and the mixture is ground and moistened with water. This mixture is extruded and subsequently dried in a stream of air.

| e) Coated granules | |
|---|---|
| Active ingredient No. 1.010 | 3% |
| Polyethylene glycol (MW 200) | 3% |
| Kaolin | 94% |

In a mixer, the kaolin which has been moistened with polyethylene glycol is uniformly coated with the finely-ground active ingredient. In this manner, non-dusty coated granules are obtained.

| f) Suspension concentrate | a) | b) |
|---|---|---|
| Active ingredient No. 1.010 | 40% | 5% |
| Ethylene glycol | 10% | 10% |
| Nonylphenol polyethylene glycol ether (15 mol EO) | 6% | 1% |
| Sodium ligninsulfonate | 10% | 5% |
| Carboxymethylcellulose | 1% | 1% |
| 37% aqeuous formaldehyde solution | 0.2% | 0.2% |
| Silicone oil in the form of a 75% aqueous emulsion | 0.8% | 0.8% |
| Water | 32% | 77% |

The finely-ground active ingredient is mixed intimately with the additives. In this manner, a suspension concentrate is obtained from which suspensions of any desired concentration can be prepared by dilution with water.

| g) Salt solution | |
|---|---|
| Active ingredient No. 1.010 | 5% |
| Isopropylamine | 1% |
| Octylphenol polyethylene glycol ether (78 mol EO) | 3% |
| Water | 91% |

BIOLOGICAL EXAMPLES

Example B1: Pre-emergence herbicidal action

In the greenhouse, the test plants are sown in pots, and the soil surface is then immediately treated with an aqueous dispersion of the active ingredients, obtained from a 25% emulsion concentrate, at a rate of application of 4 kgAS/ha. The pots are kept in the greenhouse at 22°–25° C. and 50–70% relative atmospheric humidity, and the test is evaluated after 3 weeks.

The herbicidal action is evaluated by comparison with the untreated control group, using a 9-step rating key (1=total damage of the test plant, 9=no herbicidal action on the test plant).

Rating figures of 1 to 4 (in particular 1 to 3) suggest a good to very good herbicidal action.

In this test, the compounds of Tables 1 to 14 show good herbicidal action. The results for compound No. 1.010 are compiled in Table 15:

TABLE 15

| Comp. | Pre-emergence herbicidal action | | | |
|---|---|---|---|---|
| | Test plants | | | |
| No. | Avena | Sinapis | Setaria | Stellaria |
| 1.010 | 1 | 1 | 1 | 6 |

EXAMPLE B2: Post-emergence herbicidal action

A number of weeds, both monocotyledon and dicotyledon, are sprayed after emergence (in the 4- to 6-leaf stage) with an aqueous dispersion of the active ingredient at a dosage rate of 4 kgAS/ha, and the plants are maintained at 24° to 26° C. and 40 to 60% relative atmospheric humidity. The test is evaluated 15 days after the treatment.

The herbicidal action is rated analogously to Example B1.

In this test, the compounds of Tables 1 to 14 show good herbicidal action. The results for compound No. 1.010 are compiled in Table 16:

TABLE 16

| | Post-emergence herbicidal action | | | | | | |
|---|---|---|---|---|---|---|---|
| | TEST PLANT | | | | | | |
| | Avena | Setaria | Lolium | Solanum | Sinapis | Stellaria | *Phaseolus vulg.* |
| Comp. No. 1.010 | 1 | 1 | 1 | 2 | 2 | 2 | 2 |

B3 Herbicidal action against weeds in paddy rice

The aquatic weeds are sown in plastic beakers (surface area 60 $cm^2$, volume 500 ml). After sowing, the beakers are filled with water up to the soil surface. 3 days after sowing, the water level is increased to just above the soil surface (3–5 mm). Application is effected 3 days after sowing by spraying the containers with an aqueous dispersion of the test substance. The dosage rate corresponds to rate of application of 4 kgAS/ha (amount of spray mixture: approx. 550 l/ha).

The beakers with the plants are placed in a greenhouse under optimum growth conditions for the rice weeds (at 25°–30° C. and high atmospheric humidity).

Depending on the growth rate and plant species, the tests are evaluated 2–3 weeks after application. Rating is effected analogously to the rating key mentioned in Example 1.

In this test, the compounds of Tables 1 to 14 show good herbicidal action. The results of compound No. 1.010 are compiled in Table 17:

TABLE 17

| Herbicidal action for paddy rice | | |
|---|---|---|
| Comp. | Test plant | |
| No. | Echinochloa | Monochoria |
| 1.010 | 1 | 1 |

B4 Action against *Nilaparvata lugens*

Rice plants are treated with an aqueous emulsion spray mixture containing 400 ppm of the active ingredient. After the spray coating has dried on, the rice plants are populated with cicada larvae of stage 2 and 3. The test is evaluated after 21 days. The percentage reduction of the population (% action) is determined by comparing the number of surviving cicadas on the treated with those on the untreated plants.

In this test, the compounds of Tables 1 to 14 show a good action against *Nilaparvata lugens*. In particular Compounds 1.010 and 1.015 show an action of more than 80%.

B5 Action against *Nephotettix cincticeps*

Rice plants are treated with an aqueous emulsion spray mixture containing 400 ppm of the active ingredient. After the spray coating has dried on, the rice plants are populated with cicada larvae of stage 2 and 3. The test is evaluated after 21 days. The percentage reduction of the population (% action) is determined by comparing the number of surviving cicadas on the treated with those on the untreated plants.

In this test, compounds of Tables 1 to 14 show a good action against *Nephotettix cincticeps*. In particular compound 1.010 shows an action of more than 80%.

B6 Action against *Bemisia tabaci*

Dwarf bean plants are placed in gauze cages and populated with *Bemisia tabaci* adults (whitefly). After oviposition, all adults are removed, and, after 10 days, the plants together with the nymphs are treated with an aqueous emulsion spray mixture of the active ingredients to be tested (concentration 400 ppm). The test is evaluated 14 days after application of the active ingredient by calculating the percentage hatching rate compared with the untreated control batches.

In this test, compounds according to Tables 1 to 14 show a good action against *Bemisia tabaci*. In particular, compounds 1.010, 1.015 and 1.086 show an action of more than 80%.

B7 Action against *Tetranychus urticae*

Young bean plants are populated with a mixed population of *Tetranychus urticae* and, after 1 day, sprayed with an aqueous emulsion spray mixture containing 400 ppm of the active ingredient. The plants are subsequently incubated for 6 days at 25° C. and then evaluated. The percentage reduction of the population (% action) is determined by comparing the number of dead eggs, larvae and adults on the treated plants with those on the untreated plants.

In this test, compounds of Tables 1 to 14 show a good action against *Tetranychus urticae*. In particular, compounds 1.002, 1.003, 1.004, 1.005, 1.006, 1.010, 1.012, 1.014, 1.015, 1.016, 1.086, 1.125, 2.008, 3.010, 3.015, 6.010, 10.010 and 14.001 show an action of more than 80%.

B8 Action against *Tetranychus urticae*

Young bean plants are populated with a number of female *Tetranychus urticae*, which are removed after 24 hours. The plants which are populated with eggs are sprayed with an aqueous emulsion spray mixture containing 400 ppm of the active ingredient. The plants are subsequently incubated for 6 days at 25° C. and then evaluated. The percentage reduction of the population (% action) is determined by comparing the number of dead eggs, larvae and adults on the treated plants with those on the untreated plants.

In this test, compounds of Tables 1 to 14 show a good action against *Tetranychus urticae*. In particular, compounds 1.002, 1.003, 1.004, 1.005, 1.006, 1.010, 1.012, 1.014, 1.015, 1.016, 1.086, 1.125, 2.008, 3.010, 3.015, 6.010, 10.010 and 14.001 show an action of more than 80%.

B9 Action against *Panonychus ulmi* (OP- and carb-resistant)

Apple seedlings are populated with a number of adult female *Panonychus ulmi*. After seven days, the infected plants are sprayed to drip point with an aqueous emulsion spray mixture containing 400 ppm of the test compound and grown in the greenhouse. The test is evaluated 14 days later. The percentage reduction of the population (% action) is determined by comparing the number of dead spider mites on the treated plants with those on the untreated plants.

In the above test, compounds of Tables 1 to 14 show a good action. In particular, compounds 1.002, 1.004, 1.010, 1.012, 1.014, 1.015, 1.016, and 1.086 show an action of above 80%.

What is claimed is:

1. A pyrazolidine-3,5-dione of the formula I

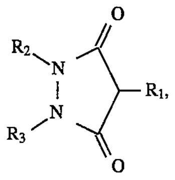

(I)

in which $R_1$ is

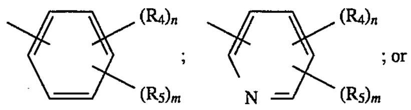

; or

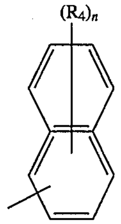

$R_2$ and $R_3$ together are a $-(CH_2)_3-$ or $-CH_2-CH{=}CH-$ bridge which is unsubstituted or up to trisubstituted by $C_1$–$C_4$alkyl;

n is 0; 1; 2; 3; or 4;

m is 0; or 1; the total of m and n being less than, or equal to, 4; the $R_4$ radicals independently of one another are halogen; nitro; cyano, $C_1$–$C_4$alkyl; $C_1$–$C_4$haloalkyl; $C_1$–$C_{10}$alkoxy; $C_1$–$C_4$haloalkoxy; $C_3$–$C_6$alkenyloxy; $C_1$–$C_4$alkoxy-$C_2$–$C_4$alkoxy; $C_3$–$C_6$alkynyloxy; $C_1$–$C_4$alkylcarbonyl; $C_1$–$C_4$alkoxycarbonyl; $C_1$–$C_4$alkylthio; $C_1$–$C_4$alkylsulfinyl; $C_1$–$C_4$alkylsulfonyl; amino; mono-$C_1$–$C_4$alkylamino; di-$C_1$–$C_4$alkylamino;

$R_5$ is

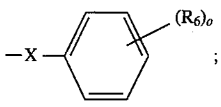 ; 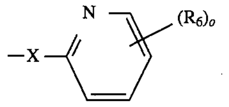

X is oxygen; sulfur; $CH_2$; or $NR_7$;

o is 0; 1; 2; or 3;

$R_6$ radicals independently of one another are $C_1$–$C_4$alkyl; halogen; $C_1$–$C_4$haloalkyl; $C_1$–$C_4$haloalkyloxy; $C_1$–$C_4$alkoxy; nitro; cyano; $C_1$–$C_4$alkoxycarbonyl; amino; mono-$C_1$–$C_4$alkylamino; or di-$C_1$–$C_4$alkylamino; and $R_7$ is hydrogen; $C_1$–$C_4$alkyl; formyl; or $C_1$–$C_4$alkylcarbonyl, or a acid addition salt thereof.

2. A pyrazolidine-3,5-dione according to claim 1, in which

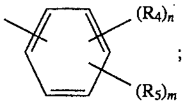 ; 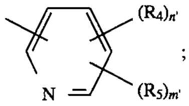 ; or

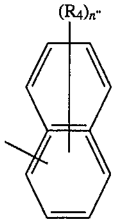

m is 0; or 1; and total of m and n is less than, or equal to, 4;

n' is 0; 1; 2; or 3;

n'' is 0; 1; or 2; and m' is 0; or 1; and the total of m' and n' is less than, or equal to, 3.

3. A pyrazolidine-3,5-dione according to claim 2, in which $R_1$ is

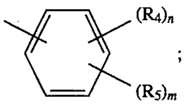 ; or 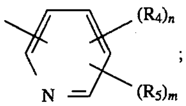 ;

$R_4$ radicals independently of one another are halogen, nitro, cyano; $C_1$–$C_4$alkyl; $C_1$–$C_4$haloalkyl; $C_1$–$C_4$alkoxy; $C_1$–$C_4$haloalkoxy; $C_3$–$C_6$alkenyloxy; $C_3$–$C_6$alkynyloxy; $C_1$–$C_4$alkylcarbonyl; $C_1$–$C_4$alkoxycarbonyl; $C_1$–$C_4$alkylthio; $C_1$–$C_4$alkylsulfinyl; $C_1$–$C_4$alkylsulfonyl; amino; mono-$C_1$–$C_4$alkylamino; di-$C_1$–$C_4$alkylamino; and $R_5$ is

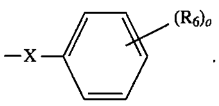 .

4. A pyrazolidine-3,5-dione according to claim 2, in which $R_1$ is

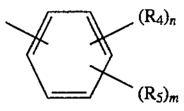 or 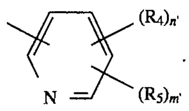 .

5. A 6,7-dihydro-1H,5H-pyrazolo[1,2-a]pyrazole-1,3(2H)-dione, according to claim 1, of the formula Id

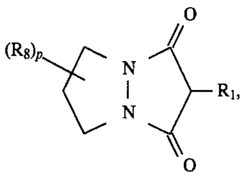 (Id)

in which $R_8$ is $C_1$–$C_4$alkyl; and p is 0, 1, 2 or 3, preferably 0.

6. A 1H,5H-pyrazolo[1,2-a]pyrazole-1,3(2H)-dione, according to claim 1, of the formula Ie

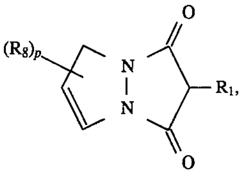 (Ie)

in which $R_8$ is $C_1$–$C_4$alkyl; and p is 0, 1, 2 or 3, preferably 0.

7. A compound according to claim 1, in which $R_1$ is

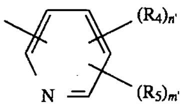

and n' is 0; 1; 2; or 3;

m' is 0; or 1; and the total of m' and n' is less than, or equal to, 3;

$R_4$ is not more than three times halogen; or $C_1$–$C_4$alkyl; not more than twice $C_1$–$C_4$alkoxy; $C_1$–$C_4$haloalkoxy; $C_1$–$C_4$alkylthio; $C_1$–$C_4$alkylsulfinyl; $C_1$–$C_4$alkylsulfonyl; amino; mono-$C_1$–$C_4$alkylamino; di-$C_1$–$C_4$alkylamino; or $C_1$–$C_4$haloalkyl; and not more than once nitro; cyano; $C_1$–$C_4$alkylcarbonyl; $C_1$–$C_4$alkoxycarbonyl; or $R_1$ is

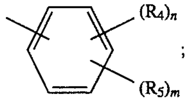 ;

n is 0; 1; 2; 3; or 4;

m is 0; or 1; and the total of m and n is less than, or equal to, 4;

$R_4$ is not more than four times halogen; or $C_1$–$C_4$alkyl; not more than three times $C_1$–$C_4$alkoxy; $C_1$–$C_4$haloalkoxy; or $C_1$–$C_4$alkylthio; and not more than twice nitro; $C_1$–$C_4$alkylsulfinyl; $C_1$–$C_4$alkylsulfonyl; amino; mono-$C_1$–$C_4$alkylamino; di-$C_1$–$C_4$alkylamino; $C_1$–$C_4$haloalkyl; or cyano; not more than once $C_1$–$C_4$alkylcarbonyl; $C_3$–$C_6$alkenyloxy; $C_3$–$C_6$alkynyloxy; $C_1$–$C_4$alkoxycarbonyl; and $R_5$ is defined under claim 1 or 2, and the meaning of the substituent $R_4$ can in each case be identical or different.

8. A compound according to claim 1, in which $R_1$ is

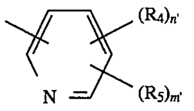

and n' is 0; 1; 2; or 3;

m' is 0;

$R_4$ is not more than three times halogen; or $C_1$–$C_4$alkyl; not more than twice $C_1$–$C_4$alkoxy; $C_1$–$C_4$haloalkyl; $C_1$–$C_4$haloalkoxy; $C_1$–$C_4$alkylthio; $C_1$–$C_4$alkylsulfinyl; $C_1$–$C_4$alkylsulfonyl; amino; mono-$C_1$–$C_4$alkylamino; or di-$C_1$–$C_4$alkylamino; and not more than once nitro; cyano; $C_1$–$C_4$alkylcarbonyl; $C_1$–$C_4$alkoxycarbonyl; or $R_1$ is

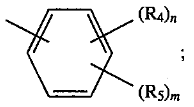

;

n is 0; 1; 2; or 3;

m is 0; or 1; and the total of m and n is less than, or equal to, 3;

$R_4$ is not more than three times fluorine; chlorine; or $C_1$–$C_4$alkyl; not more than twice $C_1$–$C_4$alkoxy; $C_1$–$C_4$haloalkyl, $C_1$–$C_4$haloalkoxy; or $C_1$–$C_4$alkylthio; and not more than once nitro; $C_1$–$C_4$alkylsulfinyl; $C_1$–$C_4$alkylsulfonyl; amino; mono-$C_1$–$C_4$alkylamino; di-$C_1$–$C_4$alkylamino; cyano; $C_1$–$C_4$alkylcarbonyl; $C_3$–$C_6$alkenyloxy; $C_3$–$C_6$alkynyloxy; or $C_1$–$C_4$alkoxycarbonyl; and the meaning of the substituent $R_4$ can in each case be identical or different.

9. A compound according to claim 1, in which $R_1$ is

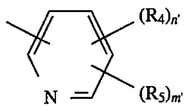

and n' is 0; 1; 2; or 3;

m' is 0;

$R_4$ is not more than three times fluorine; chlorine; or $C_1$–$C_2$alkyl; not more than twice $C_1$–$C_2$alkoxy; $C_1$–$C_2$haloalkyl; $C_1$–$C_2$haloalkoxy; $C_1$–$C_2$alkylthio; $C_1$–$C_2$alkylsulfinyl; $C_1$–$C_2$alkylsulfonyl; amino; mono-$C_1$–$C_2$alkylamino; or di-$C_1$–$C_2$alkylamino; and not more than once nitro; cyano; $C_1$–$C_2$alkylcarbonyl; $C_1$–$C_2$alkoxycarbonyl; or $R_1$ is

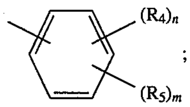

;

n is 0; 1; 2; or 3;

m is 0; or 1; and the total of m and n is less than, or equal to, 3;

$R_4$ is not more than three times fluorine, chlorine; or $C_1$–$C_4$alkyl; not more than twice $C_1$–$C_2$alkoxy; $C_1$–$C_2$haloalkyl; $C_1$–$C_2$haloalkoxy; or $C_1$–$C_2$alkylthio; and not more than once nitro; $C_1$–$C_2$alkylsulfinyl; $C_1$–$C_2$alkylsulfonyl; amino; mono-$C_1$–$C_2$alkylamino; di-$C_1$–$C_2$alkylamino; cyano; $C_1$–$C_2$alkylcarbonyl; $C_1$–$C_2$alkoxycarbonyl; and the meaning of the substituent $R_4$ can in each case be identical or different.

10. A pyrazolidine-3,5-dione according to claim 1, wherein $R_1$ is selected from the group consisting of

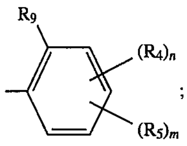

;

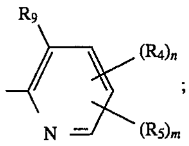

;

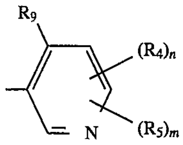

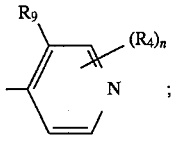

;

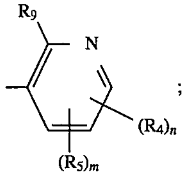

; and

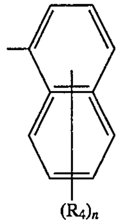

;

$R_9$ is halogen, $C_1$–$C_4$alkyl or $C_1$–$C_4$haloalkyl, the total of m+n being less than, or equal to, 3.

11. A pyrazolidine-3,5-dione according to claim 10, wherein $R_2$and $R_3$ together are $—(CH_2)_3$.

12. A pyrazolidine-3,5-dione according to claim 1, wherein $R_1$ is $R_1$ is

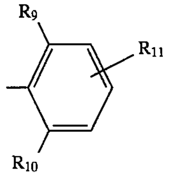

or 2-naphthyl in which $R_9$ is halogen; $C_1$–$C_4$alkyl; $C_1$–$C_4$haloalkyl;

$R_{10}$ is hydrogen; halogen; $C_1$–$C_4$alkyl; $C_1$–$C_4$haloalkyl and $R_{11}$ is hydrogen; halogen or $C_1$–$C_4$alkyl.

13. A pyrazolidine-3,5-dione according to claim 11, in which $R_1$ is 2-naphthyl or

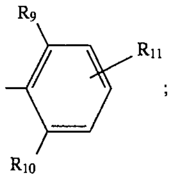

;

$R_9$ is chlorine; $C_1$–$C_2$alkyl; $C_1$–$C_2$haloalkyl;

$R_{10}$ is hydrogen; chlorine; fluorine; $C_1$–$C_2$alkyl or $C_1$–$C_2$haloalkyl; and $R_{11}$ is hydrogen; fluorine; chlorine or methyl.

14. A herbicidal composition, which comprises a herbicidally effective amount of a compound according to claim 1 and a carrier.

15. A method of controlling undesirable vegetation, which comprises applying a herbicidally effective amount of a herbicidal composition according to claim 14 to plants or their environment.

16. A method according to claim 15, wherein the undesirable vegatation are weeds and the herbicidal composition is applied for selective pre- or post-emergence control on crops of useful plants.

17. An insecticidal or arachnicidal composition which comprises an insecticidally or arachnicidally effective amount of a compound according to claim 1 and a carrier.

18. A method of controlling insects or arachnids, wherein a insecticidal or arachnicidal composition of claim 17 is applied to the insect, the arachnid or their environment.

* * * * *